(12) United States Patent
Haaga et al.

(10) Patent No.: US 9,918,950 B2
(45) Date of Patent: *Mar. 20, 2018

(54) TARGETED TREATMENT OF ANEROBIC CANCER

(71) Applicant: University Hospitals Cleveland Medical Center, Cleveland, OH (US)

(72) Inventors: John R. Haaga, Chagrin Falls, OH (US); Rebecca Haaga, Chagrin Falls, OH (US)

(73) Assignee: UNIVERSITY HOSPITALS CLEVELAND MEDICAL CENTER, Cleveland, OH (US)

(*) Notice: Subject to any disclaimer, the term of this patent is extended or adjusted under 35 U.S.C. 154(b) by 0 days.

This patent is subject to a terminal disclaimer.

(21) Appl. No.: 15/229,720

(22) Filed: Aug. 5, 2016

(65) Prior Publication Data

US 2017/0056350 A1 Mar. 2, 2017

Related U.S. Application Data

(63) Continuation of application No. 14/379,206, filed as application No. PCT/US2013/027373 on Feb. 22, 2013, now Pat. No. 9,480,745.

(60) Provisional application No. 61/604,957, filed on Feb. 29, 2012.

(51) Int. Cl.
| | |
|---|---|
| A61K 31/196 | (2006.01) |
| A61K 31/44 | (2006.01) |
| A61K 39/395 | (2006.01) |
| A61K 47/30 | (2006.01) |
| C07K 16/22 | (2006.01) |
| A61K 45/06 | (2006.01) |
| A61K 31/195 | (2006.01) |
| A61K 9/00 | (2006.01) |
| A61K 47/34 | (2017.01) |
| A61B 5/055 | (2006.01) |
| A61K 39/00 | (2006.01) |

(52) U.S. Cl.
CPC .......... *A61K 31/196* (2013.01); *A61K 9/0019* (2013.01); *A61K 31/195* (2013.01); *A61K 31/44* (2013.01); *A61K 39/39558* (2013.01); *A61K 45/06* (2013.01); *A61K 47/34* (2013.01); *C07K 16/22* (2013.01); *A61B 5/055* (2013.01); *A61K 2039/505* (2013.01); *C07K 2317/24* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 4,828,836 A | 5/1989 | Elger et al. | 424/419 |
| 5,095,026 A | 3/1992 | Schoenwald et al. | 514/367 |
| 5,302,397 A | 4/1994 | Amsden et al. | 424/473 |
| 5,384,333 A | 1/1995 | Davis et al. | 514/772.3 |
| 5,626,877 A | 5/1997 | Amsden et al. | 424/489 |
| 6,190,591 B1 | 2/2001 | Van Lengerich | 264/141 |
| 2003/0211075 A1* | 11/2003 | Thorpe | A61K 38/19 424/85.1 |
| 2009/0053236 A1 | 2/2009 | Yamamoto | 546/152 |
| 2010/0080757 A1 | 4/2010 | Haaga et al. | 600/504 |
| 2011/0124599 A1 | 5/2011 | Singh et al. | 514/230.5 |

FOREIGN PATENT DOCUMENTS

WO WO/2011/109691 9/2011

OTHER PUBLICATIONS

Goldenberg et al (Journal of Vascular Interventional Radiology, 2005, vol. 16, pp. 765-778).*
Abo-Auda, W. et al. (2003) "Therapeutic angiogenesis: review of current concepts and future directions," *Journal of Heart and Lung Transplantation* 2(4), 370-382.
Alphonso, A. et al. (2009) "Stromal cells and integrins: Conforming to the needs of the tumor microenvironment," *Neoplasia* 11(12), 1264-1271.
Arbiser, J. L. (2007) "Why targeted therapy hasn't worked in advanced cancer," *Journal of Clinical Investigation* 117(10), 2762-2765.
Assmann, V. et al. (1999) "The intracellular hyaluronan receptor RHAMM/IHABP interacts with microtubules and actin filaments," *Journal of Cell Science* 112(22), 3943-3954.
Baumann, F. et al. (2009) "Lactate promotes glioma migration by TGF-β2-dependent regulation of matrix metalloproteinase-2," *Neuro-oncology* 11(4), 368-380.
Beckert, S. et al. (2006) "Lactate stimulates endothelial cell migration," *Wound Repair and Regeneration* 14(3), 321-324.

(Continued)

*Primary Examiner* — Karen Canella
(74) *Attorney, Agent, or Firm* — Medlen & Carroll, LLP

(57) ABSTRACT

The present invention relates to a pharmaceutical cocktail and methods of treatment involving said cocktail, in particular, a combination of effective amounts of a carbonic anhydrase inhibitor, in combination with effective amounts of an angiogenesis inhibitor, including a vascular endothelial growth factor (VEGF) inhibitor such as bevacizumab for the treatment of cancer. In other embodiments, it relates to compositions and methods of treating cancer involving effective amounts of a carbonic anhydrase inhibitor. Pharmaceutical compositions and methods of treating cancer (eliminating the tumor, shrinking the tumor, prolonging the life of the patient, increasing quality of life by decreasing the grade of adverse events seen with other cancer treatments, and/or preventing/reducing the likelihood of the tumor's metastases) are additional aspects of the present invention. In addition, the present invention may be used to favorably impact the therapeutic result of patients who have not responded to alternative, traditional anti-cancer therapy.

15 Claims, 32 Drawing Sheets

(56) References Cited

OTHER PUBLICATIONS

Bisdas, S. et al. (2007) "Differentiation of benign and malignant parotid tumors using deconvolution-based perfusion CT imaging: Feasibility of the method and initial results," *European Journal of Radiology* 64(2), 258-265.

Boucher, Y. et al. (1992) "Microvascular Pressure is the Principal Driving Force for Interstitial Hypertension in Solid Tumors: Implications for Vascular Collapse," *Cancer Research* 52(18), 5110-5114.

Boucher, Y. et al. (1995) "Lack of General Correlation between Interstitial Fluid Pressure and Oxygen Partial Pressure in Solid Tumors," *Microvascular Research* 50(2), 175-182.

Brackstone, M. et al. (2007) "Tumour dormancy in breast cancer: an update," *Breast Cancer Research* 9(3), 208.

Brown, M. et al. (2008) "NF-κB in carcinoma therapy and prevention," *Expert Opinion on Therapeutic Targets* 12(9), 1109-1122.

Buadu, L. D. et al. (1996) "Breast lesions: correlation of contrast medium enhancement patterns on MR images with histopathologic findings and tumor angiogenesis," *Radiology* 200(3), 639-649.

Buckley, D. et al. (2005) "Microvessel density in invasive breast cancer assessed by dynamic gd-dtpa enhanced MRI," *Journal of Magnetic Resonance Imaging* 7(3), 461-464.

Cao, Y. et al. (2005) "Observation of Incipient Tumor Angiogenesis That is Independent of Hypoxia and Hypoxia Inducible Factor-1 Activation," *Cancer Research* 65(13), 5498-5505.

Caseiras, G. B. et al. (2008) "Inclusion or Exclusion of Intratumoral Vessels in Relative Cerebral Blood Volume Characterization in Low-Grade Gliomas: Does It Make a Difference?," *American Journal of Neuroradiology* 29(6), 1140-1141.

Chang, L. K. et al. (2004) "Dose-dependent response of FGF-2 for lymphangiogenesis," *Proceedings of the National Academy of Sciences* 101(32), 11658-11663.

Chen, H. X. et al. (2001) "Clinical trials referral resource: Current clinical trials of the anti-VEGF monoclonal antibody bevacizumab," *Oncology (Williston Park)* 15(8), 1017, 1020, 1023-1016.

Cheung, O. et al. (2010) "Recent advances in nonalcoholic fatty liver disease," *Current Opinion in Gastroenterology* 26(3), 202-208.

Choi, E.-M. et al. (2005) "COX-2 regulates p53 activity and inhibits DNA damage-induced apoptosis," *Biochemical and Biophysical Research Communications* 328(4), 1107-1112.

Cobleigh, M. A. et al. (2003) "A phase I/II dose-escalation trial of bevacizumab in previously treated metastatic breast cancer," *Seminars in Oncology* 30, 117-124.

Colotta, F. et al. (2009) "Cancer-related inflammation, the seventh hallmark of cancer: links to genetic instability," *Carcinogenesis* 30(7), 1073-1081.

Constant, J. S. et al. (2000) "Lactate elicits vascular endothelial growth factor from macrophages: a possible alternative to hypoxia," *Wound Repair and Regeneration* 8(5), 353-360.

Cruz, H. et al. (2000) "Effects of ammonia and lactate on growth, metabolism, and productivity of BHK cells," *Enzyme and Microbial Technology* 27(1-2), 43-52.

D'Arcangelo, D. et al. (2000) "Acidosis Inhibits Endothelial Cell Apoptosis and Function and Induces Basic Fibroblast Growth Factor and Vascular Endothelial Growth Factor Expression," *Circulation Research* 86(3), 312-318.

Dietl, K. et al. (2010) "Lactic Acid and Acidification Inhibit TNF Secretion and Glycolysis of Human Monocytes," *Journal of Immunology* 184(3), 1200-1209.

Duong, T. Q. et al. (2000) "In vivo MR measurements of regional arterial and venous blood volume fractions in intact rat brain," *Magnetic Resonance in Medicine* 43(3), 393-402.

Dvorak, H. et al. (1988) "Identification and characterization of the blood vessels of solid tumors that are leaky to circulating macromolecules," *American Journal of Pathology* 133, 95-109.

Dvorak, H. et al. (1991) "Distribution of Vascular Permeability Factor (Vascular Endothelial Growth Factor) in Tumors: Concentration in Tumor Blood Vessels," *Journal of Experimental Medicine* 174, 1275-1278.

Eby, P. R. et al. (2008) "Metabolic and Vascular Features of Dynamic Contrast-enhanced Breast Magnetic Resonance Imaging and 15O-Water Positron Emission Tomography Blood Flow in Breast Cancer," *Academic Radiology* 15(10), 1246-1254.

Eichten, A. et al. (2007) "Distinctive Features of Angiogenesis and Lymphangiogenesis Determine Their Functionality during De novo Tumor Development," *Cancer Research* 67(11), 5211-5220.

El Khoury, C. et al. (2005) "MR Quantification of the Washout Changes in Breast Tumors Under Preoperative Chemotherapy: Feasibility and Preliminary Results," *American Journal of Roentgenology* 184(5), 1499-1504.

Engelbrecht, M. R. et al. (2003) "Discrimination of Prostate Cancer from Normal Peripheral Zone and Central Gland Tissue by Using Dynamic Contrast-enhanced MR Imaging," *Radiology* 229(1), 248-254.

Enholm, B. et al. (2001) "Adenoviral Expression of Vascular Endothelial Growth Factor-C Induces Lymphangiogenesis in the Skin," *Circulation Research* 88(6), 623-629.

Erkkilä, K. et al. (2002) "Lactate inhibits germ cell apoptosis in the human testis," *Molecular Human Reproduction* 8(2), 109-117.

Eskey, C. J. et al. (1993) "Role of oxygen vs. glucose in energy metabolism in a mammary carcinoma perfused ex vivo: direct measurement by 31P NMR," *Proceedings of the National Academy of Sciences* 90(7), 2646-2650.

Fan, Z.-H. et al. (2006) "Evaluation of Primary Malignancies of the Liver Using Contrast-Enhanced Sonography: Correlation With Pathology," *American Journal of Roentgenology* 186(6), 1512-1519.

Fantin, V. R. et al. (2006) "Attenuation of LDH-A expression uncovers a link between glycolysis, mitochondrial physiology, and tumor maintenance," *Cancer Cell* 9(6), 425-434.

Feldmeier, J. et al. (2003) "Hyperbaric oxygen: does it promote growth or recurrence of malignancy?," *Undersea & Hyperbaric Medicine* 30(1), 1-18.

Figg, W. D. et al. (2002) "Inhibition of Angiogenesis: Treatment Options for Patients with Metastatic Prostate Cancer," *Investigational New Drugs* 20(2), 183-194.

Fischer, K. et al. (2007) "Inhibitory effect of tumor cell-derived lactic acid on human T cells," *Blood* 109(9), 3812-3819.

Folkman, J. (1990) "What is the Evidence That Tumors are Angiogenesis Dependent?," *Journal of the National Cancer Institute* 82(1), 4-7.

Franiel, T. et al. (2010) "Differentiation of Prostate Cancer From Normal Prostate Tissue: Role of Hotspots in Pharmacokinetic MRI and Histologic Evaluation," *American Journal of Roentgenology* 194(3), 675-681.

Frericks, B. et al. (2009) "Qualitative and quantitative evaluation of hepatocellular carcinoma and cirrhotic liver enhancement using Gd-EOB-DTPA," *American Journal of Roentgenology* 193(4), 1053-1060.

Fukumura, D. et al. (2001) "Hypoxia and Acidosis Independently Up-Regulate Vascular Endothelial Growth Factor Transcription in Brain Tumors in Vivo," *Cancer Research* 61(16), 6020-6024.

Gatenby, R. et al. (2006) "Acid-mediated tumor invasion: a multidisciplinary study," *Cancer Research* 66(10), 5216-5223.

Giavazzi, R. et al. (2001) "Modulation of Tumor Angiogenesis by Conditional Expression of Fibroblast Growth Factor-2 Affects Early but not Established Tumors," *Cancer Research* 61(1), 309-317.

Gillies, R. J. et al. (2007) "Adaptive landscapes and emergent phenotypes: why do cancers have high glycolysis?," *Journal of Bioenergetics and Biomembranes* 39(3), 251-257.

Gimbrone, M. A. et al. (1972) "Tumor Dormancy in Vivo by Prevention of Neovascularization," *Journal of Experimental Medicine* 136(2), 261-276.

Goerges, A. L. et al. (2004) "pH Regulates Vascular Endothelial Growth Factor Binding to Fibronectin: A Mechanism for Control of Extracellular Matrix Storage and Release," *Journal of Biological Chemistry* 279(3), 2307-2315.

Gordon, M. S. et al. (2001) "Phase I Safety and Pharmacokinetic Study of Recombinant Human Anti-Vascular Endothelial Growth Factor in Patients With Advanced Cancer," *Journal of Clinical Oncology* 19(3), 843-850.

(56) References Cited

OTHER PUBLICATIONS

Goshima, S. et al. (2009) "Optimal Acquisition Delay for Dynamic Contrast-Enhanced MRI of Hypervascular Hepatocellular Carcinoma," *American Journal of Roentgenology* 192(3), 686-692.

Graeber, T. G. et al. (1996) "Hypoxia-mediated selection of cells with diminished apoptotic potential in solid tumours," *Nature* 379(6560), 88-91.

Grillon, E. et al. (2011) "The spatial organization of proton and lactate transport in a rat brain tumor," *PLoS ONE* 6(2), e17416.

Gullino, P. M. et al. (1964) "The Interstitial Fluid of Solid Tumors," *Cancer Research* 24(5), 780-797.

Hägg, M. et al. (2005) "Activation of hypoxia-induced transcription in normoxia," *Experimental Cell Research* 306(1), 180-191.

Hajarizadeh, H. et al. (1992) "Effective palliative treatment of metastatic carcinoid tumors with intra-arterial chemotherapy/chemoembolization combined with octreotide acetate," *American Journal of Surgery* 163(5), 479-483.

Hall, C. L. et al. (1995) "Hyaluronan: RHAMM mediated cell locomotion and signaling in tumorigenesis," *Journal of Neuro-Oncology* 26(3), 221-229.

Hamed, E. A. M. (2002) Application and Evaluation of Extended Release Technology to Loop Diuretics, in *Department of Pharmaceutical Sciences of the College of Pharmacy*, p. 208, University of Cincinnati.

Hamilton, S. R. et al. (2007) "The Hyaluronan Receptors CD44 and Rhamm (CD168) Form Complexes with ERK1,2 That Sustain High Basal Motility in Breast Cancer Cells," *Journal of Biological Chemistry* 282(22), 16667-16680.

Harris, A. (2013) "Resistance to anti-angiogenic therapy induced by hypoxia and notch signalling," *European Journal of Cancer* 8(3), 183-184.

Hayashi, S.-i. et al. (2005) "Functional Ephrin-B2 Expression for Promotive Interaction Between Arterial and Venous Vessels in Postnatal Neovascularization," *Circulation* 111(17), 2210-2218.

Heinzman, J. M, et al. (2008) "Comparison of angiogenesis-related factor expression in primary tumor cultures under normal and hypoxic growth conditions," *Cancer Cell International* 8, 11.

Hendriksen, E. M. et al. (2009) "Angiogenesis, hypoxia and VEGF expression during tumour growth in a human xenograft tumour model," *Microvascular Research* 77(2), 96-103.

Holash, J. et al. (1999) "New model of tumor angiogenesis: dynamic balance between vessel regression and growth mediated by angiopoietins and VEGF," *Oncogene* 18(38), 5356-5362.

Hong, C. C. et al. (2006) "Artery/Vein Specification is Governed by Opposing Phosphatidylinositol-3 Kinase and MAP Kinase/ERK Signaling," *Current Biology* 16(13), 1366-1372.

Hong, Y.-K. et al. (2004) "VEGF-A promotes tissue repair-associated lymphatic vessel formation via VEGFR-2 and the $\alpha1\beta1$ and $\alpha2\beta1$ integrins," *FASEB Journal*.

Hong, Y.-K. et al. (2004) "Development of the lymphatic vascular system: A mystery unravels," *Developmental Dynamics* 231(3), 462-473.

Höpfl, G. et al. (2004) "HIFs and tumors—causes and consequences," *American Journal of Physiology—Regulatory, Integrative and Comparative Physiology* 286(4), R608-R623.

Hoshida, T. et al. (2006) "Imaging Steps of Lymphatic Metastasis Reveals That Vascular Endothelial Growth Factor-C Increases Metastasis by Increasing Delivery of Cancer Cells to Lymph Nodes: Therapeutic Implications," *Cancer Research* 66(16), 8065-8075.

Hoyer, R. J. et al. (2007) "Treatment of diuretic refractory pleural effusions with bevacizumab in four patients with primary systemic amyloidosis," *American Journal of Hematology* 82(5), 409-413.

Hu, L. S. et al. (2009) "Relative Cerebral Blood Volume Values to Differentiate High-Grade Glioma Recurrence from Posttreatment Radiation Effect: Direct Correlation between Image-Guided Tissue Histopathology and Localized Dynamic Susceptibility-Weighted Contrast-Enhanced Perfusion MR Imaging Measurements," *American Journal of Neuroradiology* 30(3), 552-558.

Huang, X. et al. (2007) "EphB4 Overexpression in B16 Melanoma Cells Affects Arterial-Venous Patterning in Tumor Angiogenesis," *Cancer Research* 67(20), 9800-9808.

Hunt, T. et al. (2007) "Aerobically derived lactate stimulates revascularization and tissue repair via redox mechanisms," *Antioxidants & Redox Signaling* 9(8), 1115-1124.

Hunt, T. K. et al. (2008) "Lactate, with Oxygen, Incites Angiogenesis," in *Oxygen Transport to Tissue XXXIX* (Kang, K. A., et al., Eds.), pp. 73-80, Springer US.

Hurwitz, H. (2003) Bevacizumab (Avastin, a monoclonal antibody to vascular endothelial growth factor) prolongs survival in first-line colorectal cancer (CRC): results of a phase III trial of bevacizumab in combination with bolus IFL (irinotecan, 5-fluorouracil, leucovorin), in *Presented at the 39th Annual American Society of Clinical Oncology Meeting*, Chicago, IL.

Indraccolo, S. et al. (2006) "Interruption of tumor dormancy by a transient angiogenic burst within the tumor microenvironment," *Proceedings of the National Academy of Sciences of the United States of America* 103(11), 4216-4221.

Itano, N. et al. (2002) "Abnormal accumulation of hyaluronan matrix diminishes contact inhibition of cell growth and promotes cell migration," *Proceedings of the National Academy of Sciences* 99(6), 3609-3614.

Ito, H. et al. (2003) "Visualization of prostate cancer using dynamic contrast-enhanced MRI: comparison with transrectal power Doppler ultrasound," *British Journal of Radiology* 76(909), 617-624.

Ito, K. et al. (2004) "Multiarterial Phase Dynamic MRI of Small Early Enhancing Hepatic Lesions in Cirrhosis or Chronic Hepatitis: Differentiating Between Hypervascular Hepatocellular Carcinomas and Pseudolesions," *American Journal of Roentgenology* 183(3), 699-705.

Jackson, a. S. N. et al. (2009) "Dynamic contrast-enhanced MRI for prostate cancer localization," *British Journal of Radiology* 82(974), 148-156.

Jain, R. et al. (2008) "Quantitative estimation of permeability surface-area product in astroglial brain tumors using perfusion CT and correlation with histopathologic grade," *AJNR: American Journal of Neuroradiology* 29(4), 694-700.

Jain, R. K. (2001) "Normalizing tumor vasculature with anti-angiogenic therapy: A new paradigm for combination therapy," *Natural Medicines* 7(9), 987-989.

Jain, R. K. et al. (2006) "Lessons from phase III clinical trials on anti-VEGF therapy for cancer," *Nature Clinical Practice Oncology* 3(1), 24-40.

Jain, R. K. et al. (2007) "Effect of Vascular Normalization by Antiangiogenic Therapy on Interstitial Hypertension, Peritumor Edema, and Lymphatic Metastasis: Insights from a Mathematical Model," *Cancer Research* 67(6), 2729-2735.

Jang, H.-J. et al. (2007) "Enhancement Patterns of Hepatocellular Carcinoma at Contrast-enhanced US: Comparison with Histologic Differentiation," *Radiology* 244(3), 898-906.

Jang, H.-J. et al. (2006) "Imaging of Malignant Liver Masses: Characterization and Detection," *Ultrasound Quarterly* 22(1), 19-29.

Jensen, J. A. et al. (1986) "Effect of lactate, pyruvate, and pH on secretion of angiogenesis and mitogenesis factors by macrophages," *Laboratory Investigation* 54(5), 574-578.

Karpanen, T. et al. (2001) "Vascular Endothelial Growth Factor C Promotes Tumor Lymphangiogenesis and Intralymphatic Tumor Growth," *Cancer Research* 61(5), 1786-1790.

Kato, Y. et al. (2005) "Acidic Extracellular pH Induces Matrix Metalloproteinase-9 Expression in Mouse Metastatic Melanoma Cells through the Phospholipase D-Mitogen-activated Protein Kinase Signaling," *Journal of Biological Chemistry* 280(12), 10938-10944.

Keunen, O. et al. (2011) "Anti-VEGF treatment reduces blood supply and increases tumor cell invasion in glioblastoma," *Proceedings of the National Academy of Sciences* 108(9), 3749-3754.

Kim, J.-w. et al. (2006) "Cancer's Molecular Sweet Tooth and the Warburg Effect," *Cancer Research* 66(18), 8927-8930.

(56) References Cited

OTHER PUBLICATIONS

Kim, J. K. et al. (2005) "Wash-in rate on the basis of dynamic contrast-enhanced MRI: Usefulness for prostate cancer detection and localization," *Journal of Magnetic Resonance Imaging* 22(5), 639-646.

Klenke, F. et al. (2007) "Tyrosine kinase inhibitor SU6668 represses chondrosarcoma growth via antiangiogenesis in vivo," *BMC Cancer* 7(1), 49.

Kohn, S. et al. (1992) "Pathways of macromaolecular tracer transport across venules and small veins. Structural basis for the hyperpermeability of tumor blood vessels," *Laboratory Investigation* 67(5), 596-607.

Kondoh, H. et al. (2005) "Glycolytic Enzymes Can Modulate Cellular Life Span," *Cancer Research* 65(1), 177-185.

Koukourakis, M. I. et al. (2006) "Comparison of Metabolic Pathways between Cancer Cells and Stromal Cells in Colorectal Carcinomas: a Metabolic Survival Role for Tumor-Associated Stroma," *Cancer Research* 66(2), 632-637.

Koyama, H. et al. (2007) "Hyperproduction of Hyaluronan in Neu-Induced Mammary Tumor Accelerates Angiogenesis through Stromal Cell Recruitment: Possible Involvement of Versican/PG-M," *American Journal of Pathology* 170(3), 1086-1099.

Koyama, H. et al. (2008) "Significance of Tumor-Associated Stroma in Promotion of Intratumoral Lymphangiogenesis: Pivotal Role of a Hyaluronan-Rich Tumor Microenvironment," *American Journal of Pathology* 172(1), 179-193.

Kriege, M. et al. (2004) "Efficacy of Mri and Mammography for Breast-Cancer Screening in Women with a Familial or Genetic Predisposition," *New England Journal of Medicine* 351(5), 427-437.

Kuang, D.-M. et al. (2007) "Tumor-derived hyaluronan induces formation of immunosuppressive macrophages through transient early activation of monocytes," *Blood* 110(2), 587-595.

Kuhl, C. (2007) "The Current Status of Breast MR Imaging Part I. Choice of Technique, Image Interpretation, Diagnostic Accuracy, and Transfer to Clinical Practice 1," *Radiology* 244(2), 356-378.

Kuhl, C. K. (2007) "Current Status of Breast MR Imaging Part 2. Clinical Applications1," *Radiology* 244(3), 672-691.

Kuhl, C. K. et al. (1999) "Dynamic Breast MR Imaging: Are Signal Intensity Time Course Data Useful for Differential Diagnosis of Enhancing Lesions?," *Radiology* 211(1), 101-110.

Kumar, V. B. S. et al. (2007) "Endothelial cell response to lactate: Implication of PAR modification of VEGF," *Journal of Cellular Physiology* 211(2), 477-485.

Kyzas, P. A. et al. (2004) "COX-2 expression correlates with VEGF-C and lymph node metastases in patients with head and neck squamous cell carcinoma," *Modern Pathology* 18(1), 153-160.

Lao, M.-S. et al. (1997) "Effects of Ammonium and Lactate on Growth and Metabolism of a Recombinant Chinese Hamster Ovary Cell Culture," *Biotechnology Progress* 13(5), 688-691.

Le Floch, R. et al. (2011) "CD147 subunit of lactate/H+ symporters MCT1 and hypoxia-inducible MCT4 is critical for energetics and growth of glycolytic tumors," *Proceedings of the National Academy of Sciences* 108(40), 16663-16668.

Lee, K. H. Y. et al. (2004) "Triple-Phase MDCT of Hepatocellular Carcinoma," *American Journal of Roentgenology* 182(3), 643-649.

Leese, M. P. et al. (2008) "Structure—Activity Relationships of C-17 Cyano-Substituted Estratrienes as Anticancer Agents," *Journal of Medicinal Chemistry* 51(5), 1295-1308.

Li, C.-Y. et al. (2000) "Initial Stages of Tumor Cell-Induced Angiogenesis: Evaluation via Skin Window Chambers in Rodent Models," *Journal of the National Cancer Institute* 92(2), 143-147.

Li, Y. F. et al. (2009) "The effect of homoharringtonine in patients with chronic myeloid leukemia who have failed or responded suboptimally to imatinib therapy," *Leukemia and Lymphoma* 50(11), 1889-1891.

Li, Y. M. et al. (2005) "A Hypoxia-Independent Hypoxia-Inducible Factor-1 Activation Pathway Induced by Phosphatidylinositol-3 Kinase/Akt in HER2 Overexpressing Cells," *Cancer Reseearch* 65(8), 3257-3263.

Lin, E. Y. et al. (2006) "Macrophages Regulate the Angiogenic Switch in a Mouse Model of Breast Cancer," *Cancer Research* 66(23), 11238-11246.

Liu, L. P. et al. (2009) "Focal Hypoechoic Tumors of Fatty Liver. Characterization of Conventional and Contrast-Enhanced Ultrasonography," *Journal of Ultrasound in Medicine* 28, 1133-1142.

Liu, Y. et al. (2007) "Changes of Intratumoral Microvessels and Blood Perfusion during Establishment of Hepatic Metastases in Micel," *Radiology* 243(2), 386-395.

Lu, H. et al. (2005) "Reversible Inactivation of HIF-1 Prolyl Hydroxylases Allows Cell Metabolism to Control Basal HIF-1," *Journal of Biological Chemistry* 280(51), 41928-41939.

Majewski, N. et al. (2004) "Akt Inhibits Apoptosis Downstream of BID Cleavage via a Glucose-Dependent Mechanism Involving Mitochondrial Hexokinases," *Molecular and Cellular Biology* 24(2), 730-740.

Mankoff, D. A. et al. (2002) "Blood Flow and Metabolism in Locally Advanced Breast Cancer: Relationship to Response to Therapy," *Journal of Nuclear Medicine* 43(4), 500-509.

Marx, E. et al. (1988) "Lactate-induced inhibition of tumor cell proliferation," *International Journal of Radiation Oncology Biology Physics* 14(5), 947-955.

Mayer, A. et al. (2005) "Microregional Expression of Glucose Transporter-1 and Oxygenation Status: Lack of Correlation in Locally Advanced Cervical Cancers," *Clinical Cancer Research* 11(7), 2768-2773.

McFate, T. et al. (2008) "Pyruvate Dehydrogenase Complex Activity Controls Metabolic and Malignant Phenotype in Cancer Cells," *Journal of Biological Chemistry* 283(33), 22700-22708.

Mekhail, K. et al. (2004) "Oxygen Sensing by H+: Implications for HIF and Hypoxic Cell Memory," *Cell Cycle* 3(8), 1025-1027.

Milane, L. et al. (2011) "Role of hypoxia and glycolysis in the development of multi-drug resistance in human tumor cells and the establishment of an orthotopic multi-drug resistant tumor model in nude mice using hypoxic pre-conditioning," *Cancer Cell International* 11, 3.

Miller, J. et al. (2005) "Imaging angiogenesis: applications and potential for drug development," *Journal of the National Cancer Institute* 97(3), 172-187.

Mizukami, Y. et al. (2006) "Hypoxic Regulation of Vascular Endothelial Growth Factor through the Induction of Phosphatidylinositol 3-Kinase/Rho/ROCK and c-Myc," *Journal of Biological Chemistry* 281(20), 13957-13963.

Mizukami, Y. et al. (2004) "Hypoxia-Inducible Factor-Independent Regulation of Vascular Endothelial Growth Factor by Hypoxia in Colon Cancer," *Cancer Research* 64(5), 1765-1772.

Moyon, D. et al. (2001) "Plasticity of endothelial cells during arterial-venous differentiation in the avian embryo," *Development* 128(17), 3359-3370.

Mukherjee, A. et al. (2005) "Cytotoxic and antiangiogenic activity of AW464 (NSC 706704), a novel thioredoxin inhibitor: an in vitro study," *British Journal of Cancer* 92(2), 350-358.

Nagy, J. A. et al. (2006) "Permeability properties of tumor surrogate blood vessels induced by VEGF-A," *Laboratory Investigation* 86(8), 767-780.

Nagy, J. A. et al. (2002) "Vascular Permeability Factor/Vascular Endothelial Growth Factor Induces Lymphangiogenesis as well as Angiogenesis," *Journal of Experimental Medicine* 196(11), 1497-1506.

Nagy, J. A. et al. (2002) "VEGF-A induces angiogenesis, arteriogenesis, lymphangiogenesis, and vascular malformations," *Cold Spring Harbor Symposia on Quantitative Biology* 67, 227-237.

Nalluri, S. R. et al. (2008) "Risk of Venous Thromboembolism With the Angiogenesis Inhibitor Bevacizumab in Cancer Patients," *JAMA: The Journal of the American Medical Association* 300(19), 2277-2285.

Neri, D. et al. (2011) "Interfering with pH regulation in tumours as a therapeutic strategy," *Nature Reviews Drug Discovery* 10(10), 767-777.

Nissen, N. N. et al. (1999) "Heparin and heparan sulphate protect basic fibroblast growth factor from non-enzymic glycosylation," *Biochemical Journal* 338(3), 637-642.

(56) References Cited

OTHER PUBLICATIONS

Ocak, I. et al. (2007) "Dynamic Contrast-Enhanced MRI of Prostate Cancer at 3 T: A Study of Pharmacokinetic Parameters," *American Journal of Roentgenology* 189, W192-W201.
Ozturk, S. S. et al. (1992) "Effects of ammonia and lactate on hybridoma growth, metabolism, and antibody production," *Biotechnology and Bioengineering* 39(4), 418-431.
Padhani, A. R. et al. (2000) "Dynamic Contrast Enhanced MRI of Prostate Cancer: Correlation with Morphology and Tumour Stage, Histological Grade and PSA," *Clinical Radiology* 55(2), 99-109.
Panet, R. et al. (1994) "Bumetanide and furosemide inhibited vascular endothelial cell proliferation," *Journal of Cellular Physiology* 158(1), 121-127.
Pasqui, D. et al. (2005) "Hyaluronan and sulphated hyaluronan micropatterns: effect of chemical topographic cues on lymphatic endothelial cell alighment and proliferation," *Lymphology* 38(2), 50-65.
Patan, S. et al. (2001) "Vascular Morphogenesis and Remodeling in a Human Tumor Xenograft: Blood Vessel Formation and Growth After Ovariectomy and Tumor Implantation," *Circulation Research* 89(8), 732-739.
Patel, S. D. et al. (2000) "The Lactate Issue Revisited: Novel Feeding Protocols to Examine Inhibition of Cell Proliferation and Glucose Metabolism in Hematopoietic Cell Cultures," *Biotechnology Progress* 16(5), 885-892.
Pedersen, P. (2007) "Warburg, me and Hexokinase 2: Multiple discoveries of key molecular events underlying one of cancers' most common phenotypes, the "Warburg Effect", i.e., elevated glycolysis in the presence of oxygen," *Journal of Bioenergetics and Biomembranes* 39(3), 211-222.
Pettersson, A. et al. (2000) "Heterogeneity of the Angiogenic Response Induced in Different Normal Adult Tissues by Vascular Permeability Factor/Vascular Endothelial Growth Factor," *Laboratory Investigation* 80(1), 99-115.
Pham, C. et al. (1998) "Magnetic resonance imaging detects suppression of tumor vascular permeability after administration of antibody to vascular endothelial growth factor," *Cancer Investigation* 16(4), 225-230.
Picchio, M. et al. (2008) "Intratumoral Spatial Distribution of Hypoxia and Angiogenesis Assessed by 18F-FAZA and 125I-Gluco-RGD Autoradiography," *Journal of Nuclear Medicine* 49(4), 597-605.
Pore, N. et al. (2006) "Akt1 Activation Can Augment Hypoxia-Inducible Factor-1α Expression by Increasing Protein Translation through a Mammalian Target of Rapamycin-Independent Pathway," *Molecular Cancer Research* 4(7), 471-479.
Pore, N. et al. (2004) "Sp1 is Involved in Akt-mediated Induction of VEGF Expression through an HIF-1-independent Mechanism," *Molecular Biology of the Cell* 15(11), 4841-4853.
Provenzale, J. M. et al. (2006) "Correlation of Relative Permeability and Relative Cerebral Blood Volume in High-Grade Cerebral Neoplasms," *American Journal of Roentgenology* 187(4), 1036-1042.
Quaia, E. et al. (2007) "Diagnostic Value of Hepatocellular Nodule Vascularity After Microbubble Injection for Characterizing Malignancy in Patients with Cirrhosis," *American Journal of Roentgenology* 189(6), 1474-1483.
Quennet, V. et al. (2006) "Tumor lactate content predicts for response to fractionated irradiation of human squamous cell carcinomas in nude mice," *Radiotherapy & Oncology* 81(2), 130-135.
Raatschen, H.-J. et al. (2008) "Vascular Permeability during Antiangiogenesis Treatment: MR Imaging Assay Results as Biomarker for Subsequent Tumor Growth in Rats1," *Radiology* 247(2), 391-399.
Radjenovic, A. et al. (2008) "Measurement of pharmacokinetic parameters in histologically graded invasive breast tumours using dynamic contrast-enhanced MRI," *British Journal of Radiology* 81(962), 120-128.
Ranieri, G. et al. (2006) "Vascular endothelial growth factor (VEGF) as a target of bevacizumab in cancer: from the biology to the clinic," *Current Medicinal Chemistry* 13(16), 1845-1857.
Robin, J. et al. (2008) "Multiple myeloma presenting with high-output heart failure and improving with anti-angiogenesis therapy: two case reports and a review of the literature," *Journal of Medical Case Reports* 2, 229.
Rutz, H. P. (1999) "A biophysical basis of enhanced interstitial fluid pressure in tumors," *Medical Hypotheses* 53(6), 526-529.
Rutz, H. P. et al. (1995) "Exogenous lactate interferes with cell-cycle control in Balb 3T3 mouse fibroblasts," *International Journal of Radiation Oncology Biology Physics* 31(3), 525-528.
Saksela, O. et al. (1990) "Release of basic fibroblast growth factor-heparan sulfate complexes from endothelial cells by plasminogen activator-mediated proteolytic activity," *Journal of Cell Biology* 110(3), 767-775.
Samuvel, D. J. et al. (2009) "Lactate Boosts TLR4 Signaling and NF-κB Pathway-Mediated Gene Transcription in Macrophages via Monocarboxylate Transporters and MD-2 Up-Regulation," *Journal of Immunology* 182(4), 2476-2484.
Sato, Y. (2008) "VEGFR1 for Lymphangiogenesis. An Alternative Signaling Pathway?," *Arteriosclerosis, Thrombosis, and Vascular Biology* 28, 604.
Sattler, U. G. A. et al. (2010) "Glycolytic metabolism and tumour response to fractionated irradiation," *Radiotherapy & Oncology* 94(1), 102-109.
Schlemmer, H.-P. et al. (2004) "Can pre-operative contrast-enhanced dynamic MR imaging for prostate cancer predict microvessel density in prostatectomy specimens?," *European Radiology* 14(2), 309-317.
Schmidt, D. et al. (2007) "Critical role for NF-κB-induced JunB in VEGF regulation and tumor angiogenesis," *EMBO Journal* 26(3), 710-719.
Schönmeyr, B. et al. (2008) "The effect of hyperbaric oxygen treatment on squamous cell cancer growth and tumor hypoxia," *Annals of Plastic Surgery* 60(1), 81-88.
Segal, D. et al. (2008) "Analysis of Bcl-2 family protein expression after treatment of leukemia cell lines with homoharringtonine," *Cancer Research* 68(9 Supplement), 2350.
Selvakumaran, M. et al. (2008) "Antitumor effect of the angiogenesis inhibitor bevacizumab is dependent on susceptibility of tumors to hypoxia-induced apoptosis," *Biochemical Pharmacology* 75(3), 627-638.
Semenza, G. L. (2008) "Tumor metabolism: cancer cells give and take lactate," *Journal of Clinical Investigation* 118(12), 3835-3837.
Semenza, G. L. et al. (1996) "Hypoxia Response Elements in the Aldolase A, Enolase 1, and Lactate Dehydrogenase A Gene Promoters Contain Essential Binding Sites for Hypoxia-inducible Factor 1," *Journal of Biological Chemistry* 271(51), 32529-32537.
Sheikh, A. Y. et al. (2000) "Effect of hyperoxia on vascular endothelial growth factor levels in a wound model," *Archives of Surgery* 135(11), 1293-1297.
Shi, Q. et al. (2001) "Regulation of vascular endothelial growth factor expression by acidosis in human cancer cells," *Oncogene* 20(28), 3751-3756.
Shime, H. et al. (2008) "Tumor-Secreted Lactic Acid Promotes IL-23/IL-17 Proinflammatory Pathway," *Journal of Immunology* 180(11), 7175-7183.
Siemann, D. W. (2011) "The unique characteristics of tumor vasculature and preclinical evidence for its selective disruption by Tumor-Vascular Disrupting Agents," *Cancer Treatment Reviews* 37(1), 63-74.
Song, Y. et al. (2009) "Sp-1 and c-Myc Mediate Lysophosphatidic Acid-Induced Expression of Vascular Endothelial Growth Factor in Ovarian Cancer Cells via a Hypoxia-Inducible Factor-1-Independent Mechanism," *Clinical Cancer Research* 15(2), 492-501.
Sonveaux, P. et al. (2008) "Targeting lactate-fueled respiration selectively kills hypoxic tumor cells in mice," *Journal of Clinical Investigation* 118(12), 3930-3942.
Spampinato, M. V. et al. (2007) "Cerebral blood volume measurements and proton MR spectroscopy in grading of oligodendroglial tumors," *American Journal of Roentgenology* 188(1), 204-212.
Srinivasan, R. S. et al. (2007) "Lineage tracing demonstrates the venous origin of the mammalian lymphatic vasculature," *Genes & Development* 21, 2422-2432.

(56) References Cited

OTHER PUBLICATIONS

Stahl, P. H. et al., (Eds.) (2002) *Handbook of Pharmaceutical Salts: Properties Selection and Use*, Verlag Helvetica Chimica Acta/Wiley-VCH, Zurich.

Stein, I. et al. (1995) "Stabilization of vascular endothelial growth factor mRNA by hypoxia and hypoglycemia and coregulation with other ischemia-induced genes," *Molecular and Cellular Biology* 15(10), 5363-5368.

Stein, R. (2011) FDA revokes Avastin's approval for breast cancer treatment, Washington Post, Washington, D.C. (Nov. 18, 2011).

Swift, M. R. et al. (2009) "Arterial-Venous Specification During Development," *Circulation Research* 104(5), 576-588.

Tang, W. et al. (2004) "Caveolin-1 Regulates Matrix Metalloproteinases-1 Induction and CD147/EMMPRIN Cell Surface Clustering," *Journal of Biological Chemistry* 279(12), 11112-11118.

Thangaraju, M. et al. (2006) "SLC5A8 Triggers Tumor Cell Apoptosis through Pyruvate-Dependent Inhibition of Histone Deacetylases," *Cancer Research* 66(24), 11560-11564.

Thukral, A. et al. (2007) "Inflammatory Breast Cancer: Dynamic Contrast-enhanced MR in Patients Receiving Bevacizumab—Initial Experience 1," *Radiology* 244(3), 727-735.

Timoshenko, A. V. et al. (2006) "COX-2-mediated stimulation of the lymphangiogenic factor VEGF-C in human breast cancer," *British Journal of Cancer* 94(8), 1154-1163.

Tong, R. T. et al. (2004) "Vascular Normalization by Vascular Endothelial Growth Factor Receptor 2 Blockade Induces a Pressure Gradient Across the Vasculature and Improves Drug Penetration in Tumors," *Cancer Research* 64(11), 3731-3736.

Vaupel, P. (2004) "The Role of Hypoxia-Induced Factors in Tumor Progression," *Oncologist* 9(suppl 5), 10-17.

Vaupel, P. et al. (1976) "Pathophysiological aspects of glucose uptake by the tumor tissue under various conditions of oxygen and glucose supply," *Advances in Experimental Medicine and Biology* 75, 547-553.

Vihanto, M. M. et al. (2005) "Hypoxia up-regulates expression of Eph receptors and ephrins in mouse skin," *FASEB Journal*.

Wadee, A. et al. (2011) "Recent advances in the design of drug-loaded polymeric implants for the treatment of solid tumors," *Expert Opinion on Drug Delivery* 8(10), 1323-1340.

Walenta, S. et al. (2004) "Lactate in solid malignant tumors: Potential basis of a metabolic classification in clinical oncology," *Current Medicinal Chemistry* 11(16), 2195-2204.

Weidner, N. et al. (1991) "Tumor Angiogenesis and Metastasis—Correlation in Invasive Breast Carcinoma," *New England Journal of Medicine* 324(1), 1-8.

Winkler, F. et al. (2004) "Kinetics of vascular normalization by VEGFR2 blockade governs brain tumor response to radiation: Role of oxygenation, angiopoietin-1, and matrix metalloproteinases," *Cancer Cell* 6(6), 553-563.

Workman, P. et al. (2006) "Minimally invasive pharmacokinetic and pharmacodynamic technologies in hypothesis-testing clinical trials of innovative therapies," *Journal of the National Cancer Institute* 98(9), 580-598.

Xiong, B. et al. (2002) "TGF beta1 expression and angiogenesis in colorectal cancer tissue," *World Journal of Gastroenterology* 8(3), 496-498.

Xu, L. et al. (2002) "Acidic Extracellular pH Induces Vascular Endothelial Growth Factor (VEGF) in Human Glioblastoma Cells via ERK1/2 MAPK Signaling Pathway," *Journal of Biological Chemistry* 277(13), 11368-11374.

Yancopoulos, G. D. et al. (2000) "Vascular-specific growth factors and blood vessel formation," *Nature* 407(6801), 242-248.

Yano, S. et al. (2011) "Antiangiogenic therapies for malignant pleural mesothelioma," *Frontiers in Bioscience* 16, 740-748.

Yoon, S. et al. (2009) "Multiphasic MDCT enhancement pattern of hepatocellular carcinoma smaller than 3 cm in diameter: tumor size and cellular differentiation," *American Journal of Roentgenology* 193(6), W482-489.

Yoshiji, H. et al. (1997) "Vascular Endothelial Growth Factor is Essential for Initial but not Continued in Vivo Growth of Human Breast Carcinoma Cells," *Cancer Research* 57(18), 3924-3928.

Zhong, H. et al. (2000) "Modulation of Hypoxia-inducible Factor 1α Expression by the Epidermal Growth Factor/Phosphatidylinositol 3-Kinase/PTEN/AKT/FRAP Pathway in Human Prostate Cancer Cells: Implications for Tumor Angiogenesis and Therapeutics," *Cancer Research* 60(6), 1541-1545.

PCT International Search Report of International Application No. PCT/US2013/027373 dated May 3, 2013.

European Search Report for Application No. 12802456.9 dated Jul. 14, 2015.

\* cited by examiner

TARGETED TREATMENT OF ANEROBIC CANCER

FIELD OF THE INVENTION

The present invention relates to a pharmaceutical cocktail and methods of treatment involving said cocktail, in particular, a combination of effective amounts of a carbonic anhydrase inhibitor, in combination with effective amounts of an angiogenesis inhibitor, including a vascular endothelial growth factor (VEGF) inhibitor such as bevacizumab for the treatment of cancer. The merits of this invention are based on the fact that cancer in its untreated state uses both aerobic and anaerobic/glycolytic pathways and both must be treated if the best results are to be achieved. Treatment of both metabolic pathways more completely deprives cancer of ATP energy production, thereby producing greater damage or killing of cancerous cells. Treatment of the aerobic pathway alone temporarily controls cancer but it induces mutation to a glycolytic form, which does not respond to anti-VEGF or other anti-vascular growth factor agents.

In other embodiments, it relates to compositions and methods of treating cancer involving effective amounts of a carbonic anhydrase inhibitor. Pharmaceutical compositions and methods of treating cancer (eliminating the tumor, shrinking the tumor, prolonging the life of the patient, increasing quality of life by decreasing the grade of adverse events seen with other cancer treatments, and/or preventing/reducing the likelihood of the tumor's metastases) are additional aspects of the present invention. In addition, the present invention may be used to favorably affect the therapeutic result of patients who have not responded to alternative, traditional anti-cancer therapy.

BACKGROUND OF THE INVENTION

While a number of anti-angiogenesis agents have been reported, including bevacizumab, it is not clear whether they possess the appropriate pharmacological effectiveness required to be therapeutically useful in the treatment of cancer in many situations. Therefore, there is a continued need for additional therapeutics to target such cancer and augment or revive the effectiveness of anti-angiogenesis agents to provide effective treatment of cancer.

SUMMARY OF THE INVENTION

The present invention relates to a pharmaceutical cocktail and methods of treatment involving said cocktail, in particular, a combination of effective amounts of a carbonic anhydrase inhibitor, in combination with effective amounts of an angiogenesis inhibitor, including a vascular endothelial growth factor (VEGF) inhibitor such as bevacizumab for the treatment of cancer. In other embodiments, it relates to compositions and methods of treating cancer involving effective amounts of a carbonic anhydrase inhibitor. Pharmaceutical compositions and methods of treating cancer (eliminating the tumor, shrinking the tumor, prolonging the life of the patient, increasing quality of life by decreasing the grade of adverse events seen with other cancer treatments, and/or preventing/reducing the likelihood of the tumor's metastases) are additional aspects of the present invention. In addition, the present invention may be used to favorably affect the therapeutic result of patients who have not responded to alternative, traditional anti-cancer therapy.

In one embodiment, the invention contemplates a method of treating cancer comprising administering to a patient an effective amount of a loop diuretic and an angiogenesis inhibitor. In one embodiment, said angiogenesis inhibitor is a humanized monoclonal antibody. In one embodiment, said antibody is bevacizumab. In one embodiment, said treating comprises repeated administration of at least one of the loop diuretic and angiogenesis inhibitor. In one embodiment, said loop diuretic is bumetanide. In one embodiment, said cancer is hypoxic cancer. In one embodiment, said administering results in the shrinkage of said cancer. In one embodiment, said patient has metastases and said administration reduces metastases of said cancer.

In one embodiment, the invention contemplates a method of treating cancer comprising administering to a patient an effective amount of a carbonic anhydrase inhibitor and an angiogenesis inhibitor. In one embodiment, said angiogenesis inhibitor is a humanized monoclonal antibody. In one embodiment, said treating comprises repeated administration of at least one of the carbonic anhydrase inhibitor and angiogenesis inhibitor. In one embodiment, said antibody is bevacizumab. In one embodiment, said carbonic anhydrase inhibitor and an angiogenesis inhibitor are administered to said patient at the same time. In one embodiment, said cancer is hypoxic cancer. In one embodiment, said carbonic anhydrase inhibitor is a carbonic anhydrase 9 and carbonic anhydrase 12 inhibitor. In one embodiment, said administering results in the shrinkage of said cancer. In one embodiment, said patient has metastases and said administration reduces metastases of said cancer.

In one embodiment, the invention contemplates a pharmaceutical composition comprising an effective amount of a loop diuretic and an angiogenesis inhibitor. In one embodiment, said angiogenesis inhibitor is bevacizumab. In one embodiment, said loop diuretic is bumetanide. In one embodiment, the invention contemplates said pharmaceutical composition formulated for oral administration. In one embodiment, the invention contemplates said pharmaceutical composition formulated for parenteral administration. In one embodiment, the invention contemplates said pharmaceutical composition formulated for intravenous administration.

In one embodiment, the invention contemplates a pharmaceutical composition comprising an effective amount of a carbonic anhydrase inhibitor and an angiogenesis inhibitor. In one embodiment, said angiogenesis inhibitor is bevacizumab. In one embodiment, said carbonic anhydrase inhibitor and said angiogenesis inhibitor are in a mixture. In one embodiment, the invention contemplates said formulated for oral administration. In one embodiment, the invention contemplates said formulated for parenteral administration. In one embodiment, the invention contemplates said formulated for intravenous administration.

In one embodiment, the invention contemplates a method for treating a patient with cancer, said method comprising: a) administering to said patient a carbonic anhydrase inhibitor, and b) occluding the blood vessels providing blood to said cancer. In one embodiment, said cancer is hypoxic cancer. In one embodiment, said treating results in the shrinkage of said cancer. In one embodiment, said occluding of blood vessels providing blood to said cancer comprises embolization. In one embodiment, said embolization comprises embolization with polymers embedded with carbonic anhydrase inhibitors. In one embodiment, said occluding of blood vessels providing blood to said cancer comprises thermal ablation. In one embodiment, said treating of said cancer with thermal ablation is preceded with bumetanide treatment. In one embodiment, said anhydrase inhibitor is bumetanide.

In one embodiment, the invention relates to a method of treating cancer comprising administering to a patient in need of therapy an effective amount of low dose, frequently administered combination of a carbonic anhydrase inhibitor and an angiogenesis inhibitor. In one embodiment, said angiogenesis inhibitor is selected from the group consisting of ZD6474, ZD 6126, AZD2171, SU6668 and SU5416, bevacizumab, mv833, anti-FLT-1 ribozyme, SU5416, PTK 787, ZD4190, ZD6474, CEP-7055, SU11248, and mixtures thereof. In one embodiment, said angiogenesis inhibitor is bevacizumab. In one embodiment, said carbonic anhydrase inhibitor is bumetanide. In one embodiment, said carbonic anhydrase inhibitor is a carbonic anhydrase 9 and carbonic anhydrase 12 inhibitor. In one embodiment, the treatment results in one or more of clinical benefit remission, an increased quality of life or prolongation of survival of the patient. In one embodiment, said treatment results in the shrinkage of a tumor or prolonged stability of the cancer. In one embodiment, said treatment reduces metastases of said cancer.

In one embodiment, the invention relates to a pharmaceutical composition comprising an effective amount of a combination of a carbonic anhydrase inhibitor and an angiogenesis inhibitor. In one embodiment, said angiogenesis inhibitor is selected from the group consisting of ZD6474, ZD 6126, AZD2171, SU6668 and SU5416, bevacizumab, mv833, anti-FLT-1 ribozyme, SU5416, PTK 787, ZD4190, ZD6474, CEP-7055, SU11248, and mixtures thereof. In one embodiment, said angiogenesis inhibitor is bevacizumab. In one embodiment, said carbonic anhydrase inhibitor is bumetanide. In one embodiment the invention relates to the composition described above adapted for oral administration. In one embodiment the invention relates to the composition described above adapted for parenteral administration. In one embodiment the invention relates to the composition described above adapted for intravenous administration.

In one embodiment, the invention relates to a method for treating a patient with cancer, wherein said cancer is unresponsive to traditional therapy, said method comprising administering to said patient a combination of a carbonic anhydrase inhibitor and an angiogenesis inhibitor in amounts effective to provide a clinical benefit remission, an increased quality of life or prolongation of survival of the patient. In one embodiment, said treatment results in the shrinkage of a tumor or prolonged stability of the cancer. In one embodiment, said method results in a complete remission of said cancer. In one embodiment, said angiogenesis inhibitor is bevacizumab. In one embodiment, said carbonic anhydrase inhibitor is bumetanide.

In one embodiment, the invention relates to the treatment of hypoxic cancer. In one embodiment, treatment of hypoxic cancer includes targeted bloodstream injection of a carbonic anhydrase inhibitor, such as bumetanide. In one embodiment, treatment comprises catheterization of the hepatic artery. In one embodiment, treatment comprises occluding arteries with the treatment of bumetanide. In one embodiment, treatment comprises embolization. In one embodiment, treatment comprises embolization with polymers embedded with carbonic anhydrase inhibitors. In one embodiment, said carbonic anhydrase inhibitors include a carbonic anhydrase 9 or 12 inhibitor, such as bumetanide. In one embodiment, said polymers embedded with carbonic anhydrase inhibitors slowly release bumetanide. In one embodiment, said treatment bumetanide is given intravenously in combination with artery embolization with polymers embedded with carbonic anhydrase inhibitors.

In one embodiment, the invention contemplates the treatment of cancer. In one embodiment, said cancer comprises well-defined tumors. In one embodiment, said treatment involves thermal ablation of arteries supplying blood to well defined tumors in combination with treatment with bumetanide. In one embodiment, treatment comprises additional treatment with an angiogenesis inhibitor. In one embodiment, said angiogenesis inhibitor is selected from the group consisting of ZD6474, ZD 6126, AZD2171, SU6668 and SU5416, bevacizumab, mv833, anti-FLT-1 ribozyme, SU5416, PTK 787, ZD4190, ZD6474, CEP-7055, SU11248, and mixtures thereof.

In one embodiment, the invention contemplates a method for treating a patient with cancer, said method comprising administering to said patient a carbonic anhydrase inhibitor and occlusion of blood vessels providing blood to said cancer effective to provide a clinical benefit remission, an increased quality of life or prolongation of survival of the patient. In one embodiment, said cancer is hypoxic cancer. In one embodiment, said treatment results in the shrinkage of a tumor or prolonged stability of the cancer. In one embodiment, said method results in a complete remission of said cancer. In one embodiment, said occlusion of blood vessels providing blood to said cancer comprises embolization. In one embodiment, said embolization comprises embolization with polymers embedded with carbonic anhydrase inhibitors. This embodiment provides treatment of aerobic cancer cells by occlusion of the arteries and treatment of the glycolytic cancer cells by direct action of the carbonic anhydrase inhibitor and indirectly by inhibition of glycolysis by the induced low pH. In one embodiment, said carbonic anhydrase inhibitor is bumetanide. In one embodiment, said occlusion of blood vessels providing blood to said cancer comprises thermal ablation. In one embodiment, said treatment of said cancer with thermal ablation is preceded with bumetanide treatment.

The described features, structures, or characteristics of the invention may be combined in any suitable manner in one or more embodiments. In the following description, numerous specific details are recited to provide a thorough understanding of embodiments of the invention. One skilled in the relevant art will recognize, however, that the invention may be practiced without one or more of the specific details, or with other methods, components, materials, and so forth. In other instances, well-known structures, materials, or operations are not shown or described in detail to avoid obscuring aspects of the invention.

Definitions

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

The term "patient" or "subject" is used throughout the specification to describe an animal, generally a mammal and preferably a human, to whom treatment, including prophylactic treatment, with the compositions according to the present invention is provided. For treatment of those infections, conditions or disease states, which are specific for a specific animal such as a human patient, the term patient refers to that specific animal.

The term "neoplasia" or "cancer" is used throughout the specification to refer to the pathological process that results in the formation and growth of a cancerous or malignant neoplasm, i.e., abnormal tissue that grows by cellular proliferation, often more rapidly than normal and continues to grow after the stimuli that initiated the new growth cease. Malignant neoplasms show partial or complete lack of structural organization and functional coordination with the normal tissue and most invade surrounding tissues, metastasize to several sites, and are likely to recur after attempted removal and to cause the death of the patient unless adequately treated. As used herein, the term neoplasia is used to describe all cancerous disease states and embraces or encompasses the pathological process associated with malignant hematogenous, ascitic and solid tumors. Representative cancers include, for example, stomach, colon, rectal, liver, pancreatic, lung, breast, cervix uteri, corpus uteri, ovary, prostate, testis, bladder, renal, brain/CNS, head and neck, throat, Hodgkin's disease, non-Hodgkin's lymphoma, multiple myeloma, leukemia, melanoma, acute lymphocytic leukemia, acute myelogenous leukemia, Ewing's sarcoma, small cell lung cancer, choriocarcinoma, rhabdomyosarcoma, Wilms' tumor, neuroblastoma, hairy cell leukemia, mouth/pharynx, oesophagus, larynx, kidney cancer and lymphoma, among others, including soft tissue sarcomas, which may be treated by the combination of compounds according to the present invention.

The term "remission" or "clinical benefit remission" is used to describe a remission in a patient's cancer, which may be a complete remission, a partial remission or evidence of stability of the disease.

The term "coadministration" or "combination therapy" is used to describe a therapy in which at least two active compounds or compositions in effective amounts (in the present application, at least bumetanide is coadministered with the angiogenesis inhibitor, preferably bevacizumab also being coadministered or being administered before or after the administration of bumetanide) to treat cancer, and preferably both compounds are used to treat a disease state or condition as otherwise described herein at the same time. In some embodiments, the invention involves administration of an additional chemotherapy compound(s) or composition(s).

Although the term coadministration preferably includes the administration of at least two active compounds to the patient at the same time, it is not necessary that the compounds be administered to the patient at the same time, although effective amounts of the individual compounds will be present in the patient at the same time.

The term "traditional cancer therapy" as used herein includes, but is not limited to radiation, surgical removal of cancerous tissue, and treatment with chemotherapeutic drugs, which generally have significant toxicity and undesirable side effects.

The term "carbonic anhydrase(s)" (CAs) as used herein refer to a large family of zinc metalloenzymes that catalyze the reversible hydration of carbon dioxide. They participate in a variety of biological processes, including, but not limited to, respiration, calcification, acid-base balance, bone resorption, and the formation of aqueous humor, cerebrospinal fluid, saliva, and gastric acid. Carbonic anhydrase 9 (CA9) is an enzyme that in humans is encoded by the CA9 gene and carbonic anhydrase 12 (CA12) is an enzyme that in humans is encoded by the CA12 gene. CA9 and CA12 are most commonly present in many cancer types, i.e. colon, breast, brain, kidney, lung etc. but uncommonly present in normal tissues, making them suitable for therapeutic targeting.

The term "angiogenesis inhibitor", "vascular endothelial growth factor inhibitor" "VEGF inhibitor" or "anti-VEGF therapy" all used within context, refers to a compound, composition or therapy which inhibits or otherwise prevents the angiogenesis effects of vascular endothelial growth factor (VEGF, a factor which is involved in the angiogenesis of tissue, including growth in and vascularization of tumors), regardless of mechanism.

As used herein, bumetanide (also known under trade names Bumex or Burinex) is a loop diuretic, a carbonic anhydrase inhibitor, and an aquaporin inhibitor. Bumetanide is a thiazide diuretic. The IUPAC name is 3-butylamino-4-phenoxy-5-sulfamoyl-benzoic acid. Bumetanide has the chemical structure:

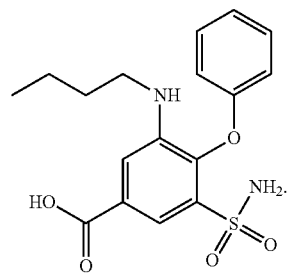 [SMILES: CCCCNc1cc(C(=O)O)cc(S(N)(=O)=O)c1Oc1ccccc1]

As used herein, thiazides are a class of drug that promotes water loss from the body ((diuretics)). They inhibit Na+/Cl− reabsorption from the distal convoluted tubules in the kidneys. Thiazides also cause loss of potassium and an increase in serum uric acid. The chemical structure of the original thiazide diuretics contained a thiazide ring system; the term is also used for drugs with a similar action that are not chemically thiazides, such as chorthalidone.

As used herein, aquaporins refer to proteins embedded in the cell membrane that regulate the flow of water. Aquaporins selectively conduct water molecules in and out of the cell, while preventing the passage of ions and other solutes. Also known as water channels, aquaporins are integral membrane pore proteins. Some of them, known as aquaglyceroporins, transport also other small uncharged solutes, such as glycerol, carbon dioxide, ammonia and urea across the membrane, depending on the size of the pore.

As used herein, embolization is a non-surgical, minimally invasive procedure performed by an interventional radiologist and interventional neuroradiologists. It involves the selective occlusion of blood vessels by purposely introducing emboli. The purpose of embolization is to prevent blood flow to an area of the body, which effectively can shrink a tumor or block an aneurysm and/or deliver therapeutic drugs or/and agents. The procedure is carried out as an endovascular procedure by a consultant radiologist in an interventional suite. It is common for most patients to have the treatment carried out with little or no sedation, although this depends largely on the organ to be embolized. Patients who undergo cerebral embolization or portal vein embolization are usually given a general anesthetic. Access to the organ in question is acquired by means of a guidewire and catheter(s). Depending on the organ, this can be very difficult and time consuming. The position of the correct artery or vein supplying the pathology in question is located by digital subtraction angiography (DSA). These images are then used as a map for the radiologist to gain access to the correct vessel by selecting an appropriate catheter and or wire, depending on the 'shape' of the surrounding anatomy. Once in place, the treatment can begin. The artificial embolus used is usually, but not limited to, one of the following: Guglielmi detachable coil or hydrocoil, particles, foam, and plug.

As used herein, thermal ablation is a method of removing aberrant tissue from within the body preferably via minimally invasive procedures. There are several types of thermal ablation used to destroy targeted tissue: cryoablation uses extremely cold temperatures to freeze diseased tissue, radiofrequency ablation uses heat generated by radiofrequency energy, microwave ablation uses heat generated by microwave energy, Laser ablation uses heat from a laser beam, and ultrasound ablation uses heat from focused ultrasound energy.

As used herein, the "nano knife system" is a minimally invasive cancer treatment that uses irreversible electroporation technology to precisely target and kill hard-to-reach tumors at the cellular level. It employs irreversible electroporation that uses a series of microsecond electrical pulses.

The term "occluding" as used herein refers to cause to become closed, such as blood vessels; to obstruct or occlude an artery. Embolization is one method of occluding blood vessels or lymphatic vessels.

The term "salts", as used herein, refers to any salt that complexes with identified compounds contained herein while retaining a desired function, e.g., biological activity. Examples of such salts include, but are not limited to, acid addition salts formed with inorganic acids (e.g. hydrochloric acid, hydrobromic acid, sulfuric acid, phosphoric acid, nitric acid, and the like), and salts formed with organic acids such as, but not limited to, acetic acid, oxalic acid, tartaric acid, succinic acid, malic acid, fumaric acid, maleic acid, ascorbic acid, benzoic acid, tannic acid, pamoic acid, alginic acid, polyglutamic, acid, naphthalene sulfonic acid, naphthalene disulfonic acid, and polygalacturonic acid. Pharmaceutically acceptable salts also include base addition salts, which may be formed when acidic protons present are capable of reacting with inorganic or organic bases. Suitable pharmaceutically-acceptable base addition salts include metallic salts, such as salts made from aluminum, calcium, lithium, magnesium, potassium, sodium and zinc, or salts made from organic bases including primary, secondary and tertiary amines, substituted amines including cyclic amines, such as caffeine, arginine, diethylamine, N-ethyl piperidine, histidine, glucamine, isopropylamine, lysine, morpholine, N-ethyl morpholine, piperazine, piperidine, triethylamine, and trimethylamine. All of these salts may be prepared by conventional means from the corresponding compound of the invention by reacting, for example, the appropriate acid or base with the compound of the invention. Unless otherwise specifically stated, the present invention contemplates pharmaceutically acceptable salts of the considered prodrugs.

In addition, atoms making up the compounds of the present invention are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}C$ and $^{14}C$. Similarly, it is contemplated that one or more carbon atom(s) of a compound of the present invention may be replaced by a silicon atom(s). Furthermore, it is contemplated that one or more oxygen atom(s) of a compound of the present invention may be replaced by a sulfur or selenium atom(s).

In structures wherein stereochemistry is not explicitly indicated, it is assumed that all stereochemistry is considered and all isomers claimed.

Any undefined valency on an atom of a structure shown in this application implicitly represents a hydrogen atom bonded to the atom. Bonds to copper (Cu) metal may be coordinate bonds and are not necessarily considered covalent.

The term "effective," as that term is used in the specification and/or claims, means adequate to accomplish a desired, or hoped for result.

The term "hydrate" when used as a modifier to a compound means that the compound has less than one (e.g., hemihydrate), one (e.g., monohydrate), or more than one (e.g., dihydrate) water molecules associated with each compound molecule, such as in solid forms of the compound.

An "isomer" of a first compound is a separate compound in which each molecule contains the same constituent atoms as the first compound, but where the configuration of those atoms in three dimensions differs.

As used herein, the term "patient" or "subject" refers to a living mammalian organism, such as a human, monkey, cow, sheep, goat, dog, cat, mouse, rat, guinea pig, or transgenic species thereof. In certain embodiments, the patient or subject is a primate. Non-limiting examples of human subjects are adults, juveniles, infants and fetuses.

The term "Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Pharmaceutically acceptable salts" means salts of compounds of the present invention which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylicacids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, trimethylacetic acid, and the like. Pharmaceutically acceptable salts also include base addition salts, which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, and Use* (P. H. Stahl & C. G. Wermuth eds., Verlag Helvetica Chimica Acta, 2002) [1] herein incorporated by reference. Unless otherwise specifically stated, the present invention contemplates pharmaceutically acceptable salts of the considered pro-drugs.

As used herein, "predominantly one enantiomer" means that a compound contains at least about 85% of one enantiomer, or more preferably at least about 90% of one enantiomer, or even more preferably at least about 95% of one enantiomer, or most preferably at least about 99% of one enantiomer. Similarly, the phrase "substantially free from other optical isomers" means that the composition contains at most about 15% of another enantiomer or diastereomer, more preferably at most about 10% of another enantiomer or diastereomer, even more preferably at most about 5% of another enantiomer or diastereomer, and most preferably at most about 1% of another enantiomer or diastereomer.

The term "Prevention" or "preventing" as used herein includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

The terms "reduce," "inhibit," "diminish," "suppress," "decrease," "prevent" and grammatical equivalents (including "lower," "smaller," etc.) when in reference to the expression of any symptom in an untreated subject relative to a treated subject, mean that the quantity and/or magnitude of the symptoms in the treated subject is lower than in the untreated subject by any amount that is recognized as clinically relevant by any medically trained personnel. In one embodiment, the quantity and/or magnitude of the symptoms in the treated subject is at least 10% lower than, at least 25% lower than, at least 50% lower than, at least 75% lower than, and/or at least 90% lower than the quantity and/or magnitude of the symptoms in the untreated subject.

The term "saturated" when referring to an atom means that the atom is connected to other atoms only by means of single bonds.

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers.

Enantiomers are compounds that individually have properties said to have "optical activity" and consist of molecules with at least one chiral center, almost always a carbon atom. If a particular compound is dextrorotary, its enantiomer will be levorotary, and vice-versa. In fact, the enantiomers will rotate polarized light the same number of degrees, but in opposite directions. "Dextrorotation" and "levorotation" (also spelled laevorotation) refer, respectively, to the properties of rotating plane polarized light clockwise (for dextrorotation) or counterclockwise (for levorotation). A compound with dextrorotation is called "dextrorotary," while a compound with levorotation is called "levorotary."

A standard measure of the degree to which a compound is dextrorotary or levorotary is the quantity called the "specific rotation" "$[\alpha]$". Dextrorotary compounds have a positive specific rotation, while levorotary compounds have negative. Two enantiomers have equal and opposite specific rotations. A daxtrorotary compound is prefixed "(+)-" or "d-". Likewise, a levorotary compound is often prefixed "(−)-" or "l-". These "d-" and "l-" prefixes should not be confused with the "D-" and "L-" prefixes based on the actual configuration of each enantiomer, with the version synthesized from naturally occurring (+)-compound being considered the D-form. A mixture of enantiomers of the compounds is prefixed "(±)-". An equal mixture of enantiomers of the compounds is considered "optically inactive."

The invention contemplates that for any stereocenter or axis of chirality for which stereochemistry has not been defined, that stereocenter or axis of chirality can be present in its R form, S form, or as a mixture of the R and S forms, including racemic and non-racemic mixtures.

The present invention contemplates the above-described compositions in "therapeutically effective amounts" or "pharmaceutically effective amounts", which means that amount which, when administered to a subject or patient for treating a disease, is sufficient to effect such treatment for the disease or to ameliorate one or more symptoms of a disease or condition (e.g. ameliorate pain).

As used herein, the terms "treat" and "treating" are not limited to the case where the subject (e.g. patient) is cured and the disease is eradicated. Rather, the present invention also contemplates treatment that merely reduces symptoms, improves (to some degree) and/or delays disease progression. It is not intended that the present invention be limited to instances wherein a disease or affliction is cured. It is sufficient that symptoms are reduced.

"Subject" refers to any mammal, preferably a human patient, livestock, or domestic pet.

In a specific embodiment, the term "pharmaceutically acceptable" means approved by a regulatory agency of the federal or a state government or listed in the U.S. Pharmacopeia or other generally recognized pharmacopeia for use in animals, and more particularly in humans. The term "carrier" refers to a diluent, adjuvant, excipient or vehicle with which the active compound is administered. Such pharmaceutical vehicles can be liquids, such as water and oils, including those of petroleum, animal, vegetable or synthetic origin, such as peanut oil, soybean oil, mineral oil, sesame oil and the like. The pharmaceutical vehicles can be saline, gum acacia, gelatin, starch paste, talc, keratin, colloidal silica, urea, and the like. In addition, auxiliary, stabilizing, thickening, lubricating and coloring agents can be used. When administered to a subject, the pharmaceutically acceptable vehicles are preferably sterile. Water can be the vehicle when the active compound is administered intravenously. Saline solutions and aqueous dextrose and glycerol solutions can also be employed as liquid vehicles, particularly for injectable solutions. Suitable pharmaceutical vehicles also include excipients such as starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol and the like. The present compositions, if desired, can also contain minor amounts of wetting or emulsifying agents, or pH buffering agents.

Pharmaceutically acceptable sugars include but are not limited to sucrose, dextrose, maltose, galactose, rhamnose, and lactose. Pharmaceutically acceptable sugar alcohols include but are not limited to mannitol, xylitol, and sorbitol.

As used herein, "extended release" refers to providing continuous therapeutic level of an active agent (e.g., neuregulin) over a period of time. The extended release includes, without limitation various forms of release, such as continuous release, controlled release, delayed release, depot, gradual release, long-term release, programmed release, prolonged release, proportionate release, protracted release, repository, retard, slow release, spaced release, sustained release, time coat, timed release, delayed action, extended action, layered-time action, long acting, prolonged action, repeated action, slow acting, sustained action, sustained-action medications, and controlled release. The ability to obtain extended release, controlled release, timed release, sustained release, delayed release, long acting, pulsatile delivery or immediate release is performed using well-known procedures and techniques available to the ordinarily skilled artisan.

The amount of time over which the active agent continues to be released depends on the characteristics of the active agent and the extended release technology or technologies used, but in all cases is longer than that of administration of the active agent without the extended release technology or technologies. Other forms of slow release compositions are described in the following: U.S. Pat. No. 4,828,836 [2], U.S. Pat. No. 6,190,591 [3].

DESCRIPTION OF THE FIGURES

The accompanying figures, which are incorporated into and form a part of the specification, illustrate several embodiments of the present invention and, together with the description, serve to explain the principles of the invention. The figures are only for the purpose of illustrating a preferred embodiment of the invention and are not to be construed as limiting the invention.

FIG. 4A shows a T2-weighted image. FIG. 4B shows a relative cerebral blood volume map shows low tumoral vascularity.

FIG. 5B shows a relative cerebral blood volume map shows elevated tumor vascularization of tumor.

FIG. 8A shows the region of interest (black oval on the left image) and FIG. 8B shows the corresponding time-signal intensity curve.

DETAILED DESCRIPTION OF THE INVENTION

I. Introduction

Figure 1:
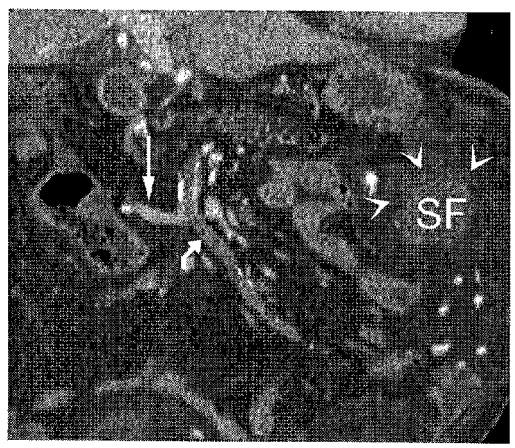
FIG. 1A-1B shows a multidetector computed tomography (MDCT) of the abdomen performed on a patient with severe abdominal pain.
Figure 1:
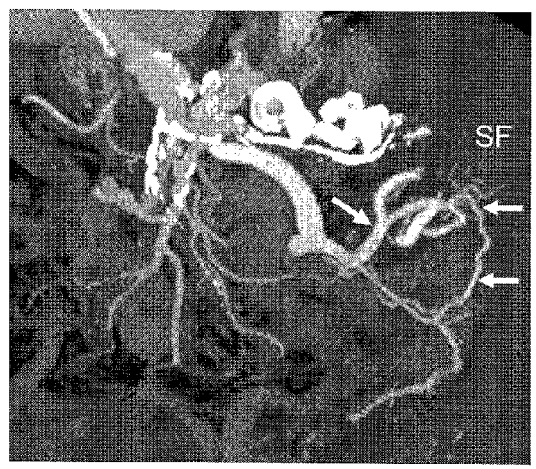

The currently accepted oxygen based arteriogenesis concept evolved from an experiment by Gimbrone [4] and Folkman [5] (both herein incorporated by reference) which reported the interruption of tumor dormancy by vasculogenesis. Although no oxygen measurements were made, it has since been inferred that hypoxia induces the VEGF (vascular endothelial growth factor) which initiates arterial growth.

Of the voluminous amounts of research data on angiogenesis, numerous data has been contradictory and inconsistent with the current hypoxia/arterial based theory, Sheikh, A. Y. et al. (2000) [6] herein incorporated by reference. Hypoxia is not necessary for angiogenesis because it occurs in normoxic wounds. Relative to treatment, it had been believed that anti-VEGF drugs would destroy arteries and cancer but recently the FDA withdrew its approval of the use of Avastin as a primary treatment for breast cancer (Stein 2011) [7], incorporated herein by reference. This negative action was based on lack of effectiveness and increased incidence of complications with Avastin, most notably venous thrombophlebitis [8-11], incorporated herein by reference. Another contradictory observation regarding anti-VEGF drugs are that they transiently increase arterial flow (or normalize) rather than decreasing it [12-15], incorporated herein by reference.

Other important inconsistencies are based on imaging studies of tumor perfusion. Vascular physiology dictates that arterial flow cannot occur without pre-existing venous outflow, (FIG. 1A-1B); ingrowth of arteries without veins cannot occur. Perfusion studies using MRI (magnetic resonance imaging), MDCT (multidetector computed tomography), and ultrasound show that the most reliable vascular parameters are venous not arterial.

In an attempt to resolve these inconsistencies, data was studied from diverse fields (i.e. bioenergetics, biomechanics, genetics, biomarkers, cytoarchitecture, proteonics, and signaling pathways) related to angiogenesis and found that much of the reported data can be interpreted to suggest an alternate angiogenesis theory. By collating these data, the following concept was formulated: Cancers prefer glycolytic metabolism, requiring only glucose and not oxygen, which makes ample ATP energy but also creates large amounts of lactate and low pH. Depending upon the concentration levels these waste products may provide specific benefits to cancer, cause tumor dormancy, and transform the microenvironment. Angiogenesis follows transformation and interrupts tumor dormancy, thus promoting cancer growth. The vascular changes occur sequentially in the lymphatics, veins, and lastly, the arteries (not first, as previously believed).

We propose the newly formulated concept, designated by the acronym $A^3L^2PHA$ (Aerobic Anaerobic Acid and Lactate sequentially induced Lymphatics, PHlebos/veins Arteries) for consideration by the scientific community.

II. Contradictions and Inconsistencies of the Current Theory

The impetus for this new angiogenesis concept has been the revelation of numerous inconsistencies and paradoxes. Some will only be mentioned and others discussed more fully to emphasize the need for a new paradigm. From the basic science arena, it has been noted that anti-VEGF drugs do not decrease central arterial blood flow but actually increases it, in a process called "normalization" [12-15]. Interruption of the arterial supply to a tumor by surgical ligature or angiographic bland (no chemical agents) embolization has little long-term effect on tumor viability. Although cancer becomes hypovascular as they enlarge, their aggressive nature increases when hypoxia is present.

There are two inconsistencies that will be more fully discussed: 1) the lack of effectiveness of anti-VEGF drugs for the primary treatment of tumors; and 2) the inconsistencies noted in perfusion imaging of cancer in clinical patients.

FDA Withdrew its Approval of an Anti-VEGF Drug

In July 2010, the Oncologic Drug Advisory Committee withdrew its approval of Avastin for the treatment of breast cancer. This action was taken because of its lack of effectiveness and its association with higher complications Nalluri, S. R. et al. (2008) [11], incorporated herein by reference.

Angiographic Principles and Modern Perfusion Studies Demonstrate the Importance of the Venous System for Cancer Considering the numerous and varying reports, greater significance must be given to patient studies reflecting clinical reality. In the clinical imaging realm, experience based on angiography and the vascular perfusion of tumors, the importance of the venous system is quite evident.

The concept that arteries form first is contrary to basic vascular physiology because without venous outflow arterial inflow cannot occur or be sustained. This is unequivocally well known to angiographers and surgeons as surgical repair of an occluded vascular stenosis cannot succeed unless there is adequate downstream flow. Most intestinal infarctions treated by abdominal surgeons are caused by venous occlusion which impair arterial flow and causes infarction.

Using modern multiphasic contrast enhanced CTA (computed tomographic arteriography) and CTV (computed tomographic venography), with reconstructions, such venous infarctions can now be imaged, (FIG. 1A-1B).

FIG. 1A-1B shows a multidetector computed tomography (MDCT) of the abdomen performed on a patient with severe abdominal pain, multiplanar reconstructions were obtained. Arteries and veins are displayed. FIG. 1A: The coronal plane shows the inferior mesenteric vein with contrast flow noted in the lateral branch, indicated by the vertical arrow, but with no flow in the main vein, as indicated by the horizontal veins. Note the edema and stranding for the splenic flexure, which is infracted because there is no arterial flow. Extensive edema of the splenic flexure region is also noted. FIG. 1B: Combined Arterial and venous enhancement shows collateral veins draining the descending colon, but not the splenic flexure (SF). Arterial flow is maintained to the descending colon but there is no arterial supply to splenic flexure.

Additional data on cancer perfusion obtained from MRI, MDCT and ultrasound reveal that the most consistently useful assessments of tumor vascular perfusion are derived from the venous and not the arterial system. The specific assessment techniques will only be discussed only in general terms, although all of the modern methods, such as DCE MRI, MDCT, and ultrasound use similar techniques. With each modality, baseline unenhanced images are obtained and subsequent repetitive images are obtained at varying time intervals during an intravenous bolus injection of appropriate contrast material (i.e. gadolinium, iodinated, or microbubbles)

Figure 2:
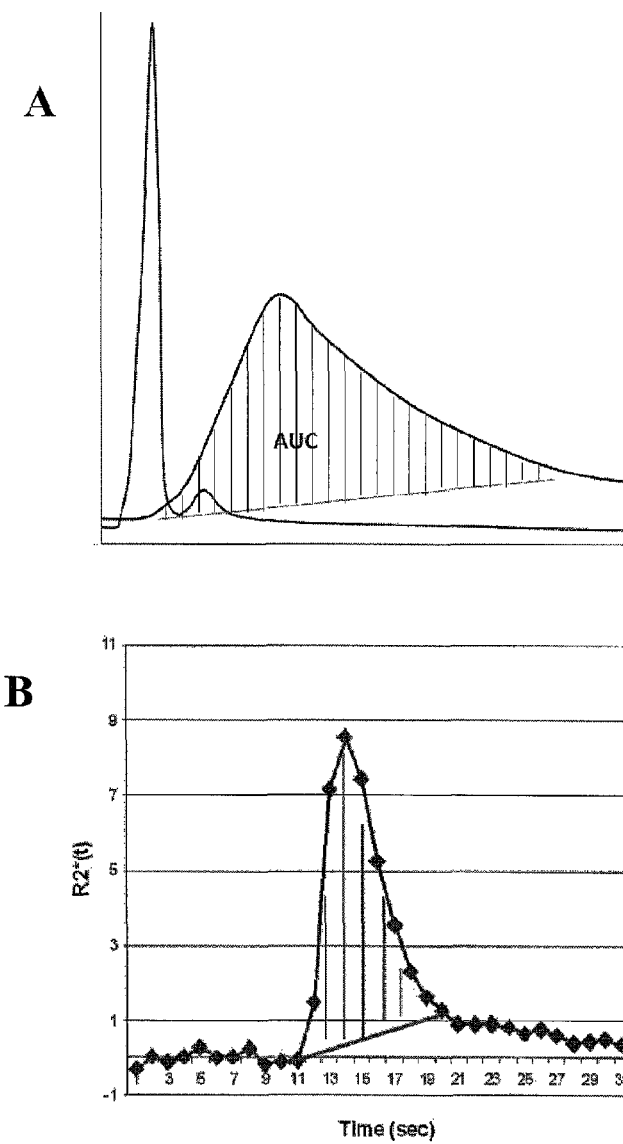
FIG. 2A-2B shows blood volume calculated using the area under the contrast curve over time (AUC).

The contrast-enhanced images can be analyzed visually or more vigorously by graphing or analyzed mathematically. Such contrast time curves are an essential component of MRI vascular imaging. The typical graph shows the density or intensity curve over the time intervals, (FIG. 2a). Depending upon the character of the arteries, veins, and arteriovenous shunts the shape of the curve varies (FIG. 2b). With MRI, semiquantitative measurements are made because absolute values of intensity, density, or flow measurements are quite variable due to the technical, paramagnetic, physiologic and equipment factors. Mathematical calculation of the permeability expressed as K or K, can be calculated Workman, P. et al. (2006) [16] and Miller, J. et al. (2005) [17], incorporated herein by reference.

FIG. 2a. shows data obtained from a contrast enhanced study graph is used to construct an intensity/time or density/time curve. The diagram compares the contrast time curve for the aorta (A) and a typical density time curve over a mass. The AUC (area under the curve) represents the opacified blood as seen during the arterial and venous outflow phase. The shape of the curve can be visually analyzed as a "kinetic curve", as is commonly done with gadolinium enhanced DCE MRI mammography. Although inflow and outflow are related, the outflow curve mostly depends upon the venous characteristics. The second image in FIG. 2b shows, a "spike" which requires rapid inflow and rapid outflow. In either curve, the outflow down slope depends on the venous system.

FIG. 2b shows a demonstration of the CBV calculation method by which integrates from the start to the end of the R2* (t) curve first-pass bolus, using the baseline subtraction method from T2/T2*—weighted leakage correction [18], Hu, L. S. et al. (2009) incorporated herein by reference.

Blood Volume

Blood volume is calculated using the area under the contrast curve over time (AUC), (FIG. 2A-2B). This area represents the total blood volume including the arteries and the veins, although as can be seen, the greatest contributor to the total volume is the venous volume. Duong et al. [19], incorporated herein by reference, calculated that in the normal blood volume, the venous space represents 70%, with the arteries contributing the rest.

Permeability Values

Permeability represents the exchange of fluid or small particles in the intravascular and extravascular spaces. This exchange depends somewhat on the arterial inflow and the venous outflow characteristics but also on the nature of the exchange sites at the capillary level. Dvorak [20, 21], Nagy [22, 23], and Kohn [24], all incorporated herein by reference, have shown that permeability occurs in venules through fenestra as well as in the vesiculo-vacuolar transport organelles which traverse the venous wall. Dvorak [20, 21] and Kohn [24] studied tracer macromolecular transport across vessels. Nagy et al. [22, 23] studied vascular permeability in an adenovirus transfected VEGF model and determined permeability occurred in veins not arteries using electron microscopy, Evan's blue dye, and albumin dual radiotracers.

Permeability values can be calculated from both CT and MRI, but they are most commonly used in conjunction with gadolinium-enhanced DCE MRI (dynamic contrast-enhanced magnetic resonance imaging). According to Workman [16], these are "$K^{trans}$ ($min^{-1}$), the rate of flux of contrast agent into the extracellular extravascular space within a given volume, or volume transfer constant); $v_e$, the volume of the extracellular extravascular space; and $k_{ep}$ ($min^{-1}$), the rate constant for the back flux from the extracellular extravascular space to the vasculature. These parameters are related to each other by the equation, $k_{ep} = K^{trans}/v_e$." The mathematical derivations of these values are beyond the scope of this commentary, and the reader is referred to several excellent reports [16, 17].

Kinetic Curves

A subjective evaluation of the shape of the inflow and outflow portions of the time contrast curves has been found to be a useful interpretive tool for DCE MRI of the breast. Many sources especially Kuhl [25-27], all incorporated herein by reference, have used analysis of these "kinetic" curves for the diagnosis of breast cancer. However, attempts to apply these curves to other organ systems have been less successful.

Looking at the curve, FIG. 2a and FIG. 2b, it is apparent that the inflow slope represents the arterial inflow rate. The peak correlates with the maximal enhancement and the outflow portion reflects venous properties. In general, the inflow slope has been considered to be less useful in the analysis because it is too dependent upon technical factors related to contrast injection, e.g. rate, volume, etc. A very high peak is considered a spike if it is 60% above the baseline; although a spike is typically thought of as being characteristic of arteries, it is apparent that if there is not rapid outflow representing veins, it could not be a spike.

Washout

"Wash out" of contrast material is a simple interpretive sign based on the observation that an enhancing focal mass quickly shows decreased enhancement and compared to normal tissue enhancement, it "washes out" earlier. This has been most commonly used with hepatic masses, during a bolus of contrast material on DCE MRI, MDCT or ultrasound imaging.

Perfusion Parameters of Different Organ Systems

The literature shows that while the above mentioned parameters depend upon the venous properties, their usefulness in the different organs varies greatly. For example, permeability or kinetic curve analysis are worthwhile in some organs but not others. The most plausible explanation is of course that the receptors, physiology, chemistry of the organs differ greatly so the individual characteristics dictate the vascular properties.

Brain

Using DCE MRI and bold imaging, numerous sources have reported that blood volume measurements can be used without factors to predict the degree of a parotid [28] malignant brain tumor differentiation [14, 15, 29-32]. Spampinato et al. [32], incorporated herein by reference, concluded that, "Relative cerebral blood volume measurement and MRS (MRI spectroscopy) are helpful in differentiating low-grade from anaplastic oligodendroglial tumors", (FIG. 3, FIG. 4A-4B, and FIG. 5A-5B). Jain et al [31], incorporated herein by reference, noted that differentiating high and low grade astroglial tumors was possible using the PS (permeability surface area) and CBV (cerebral blood volume). Hu et al. [33], incorporated herein by reference, reported that cerebral blood volume measurements could differentiate high-grade glioma recurrence from post-radiation therapy changes.

Figure 3:
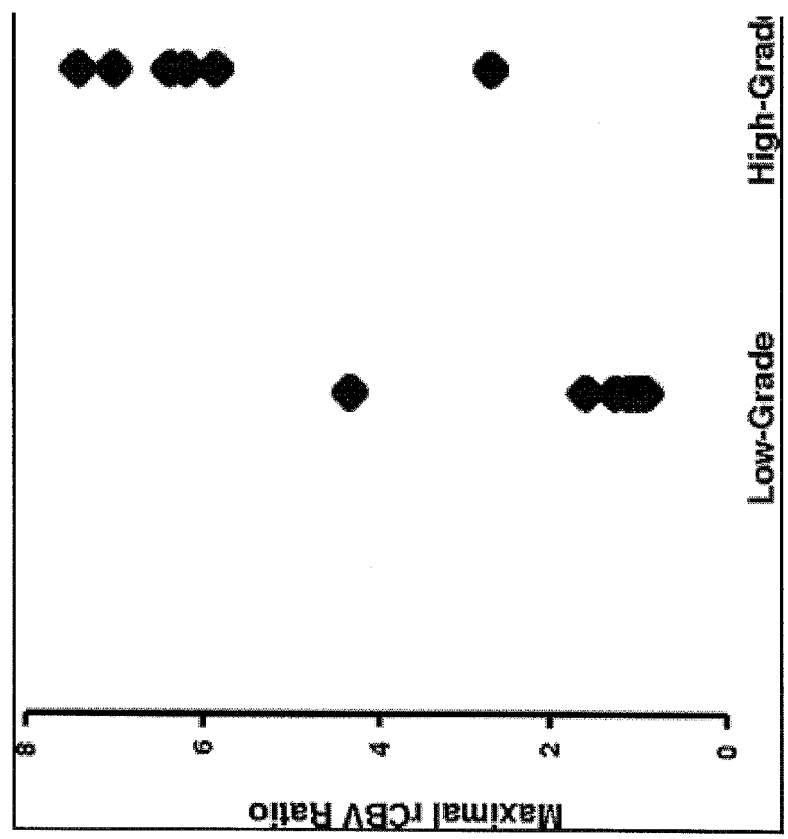
FIG. 3 shows a scatter plot of relative cerebral blood volume (rCBV) ratios for each tumor shows significant difference between the low-grade and high-grade oligodendroglial tumors (p<0.05)

FIG. 3 shows a scatter plot of relative cerebral blood volume (rCBV) ratios for each tumor shows significant difference between the low-grade and high-grade oligodendroglial tumors (p<0.05) [32].

Figure 4:
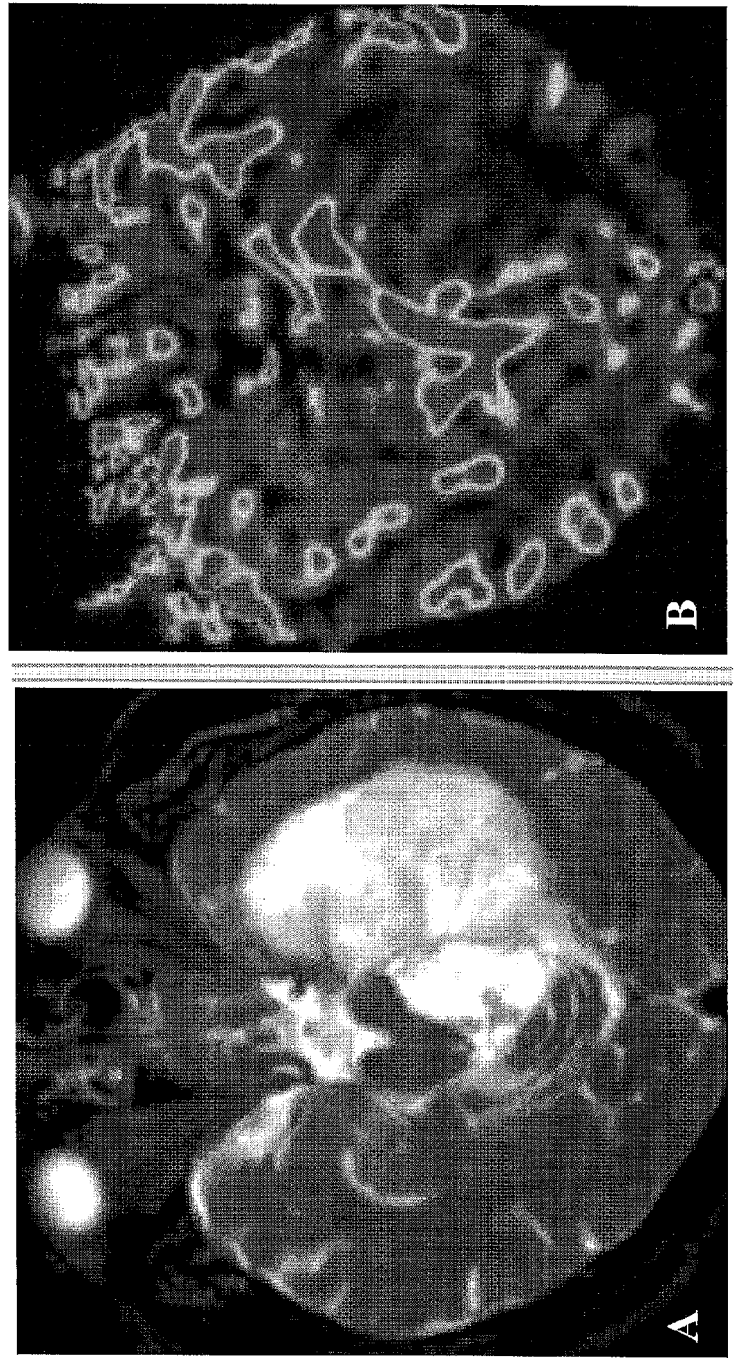
FIG. 4A-4B shows scans of a 44-year-old man with low-grade oligoastrocytoma.

FIG. 4A-4B shows a 44-year-old man with low-grade oligoastrocytoma. T2-weighted image. FIG. 4b Relative cerebral blood volume map shows low tumoral vascularity [32].

Figure 5:
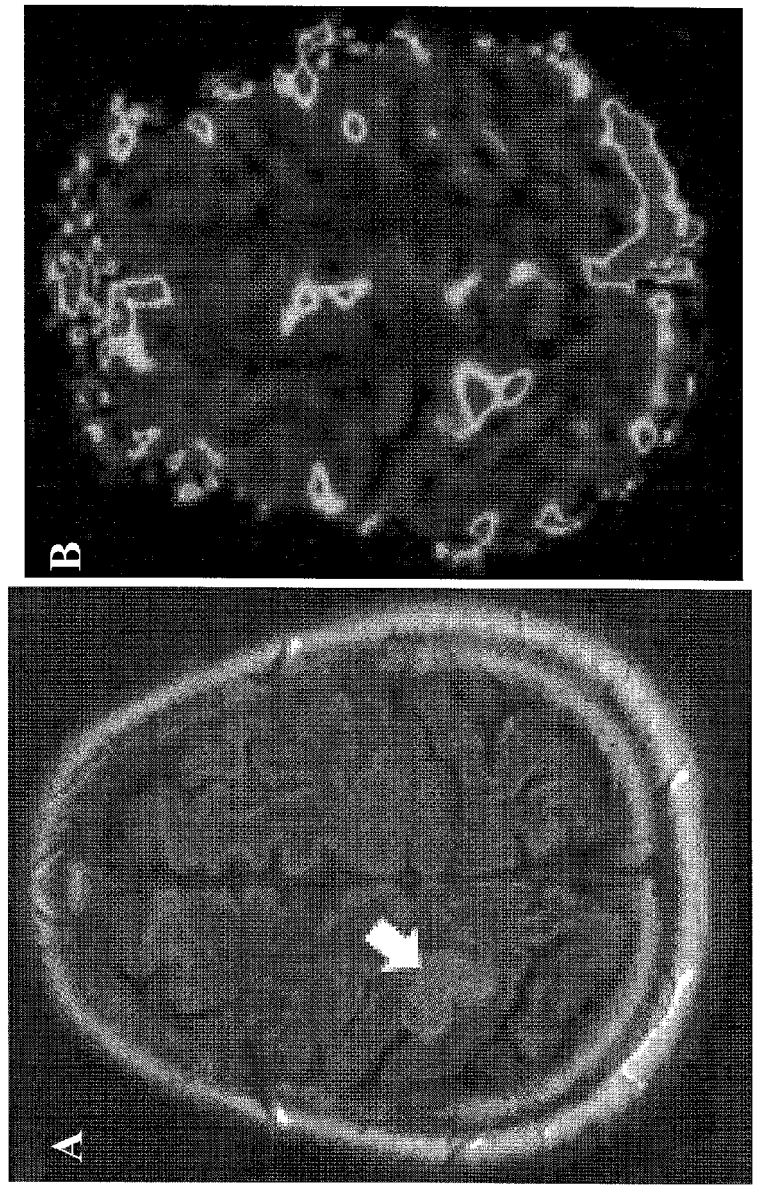
FIG. 5A-5B shows scans of a 64-year-old man with anaplastic oligodendroglioma. FLAIR image corresponding to FIG. 5A shows a right frontal cortex-based mass (arrow).

FIG. 5a. shows a 64-year-old man with anaplastic oligodendroglioma. FLAIR image corresponding to A shows a right frontal cortex-based mass (arrow). FIG. 5b. Relative cerebral blood volume map shows elevated tumor vascularization of tumor. [32].

Breast

To diagnose breast cancer using MRI, kinetic curves and permeability measurements have become widely accepted as useful diagnostic tools for both diagnosing and characterizing breast cancer. When the morphologic MRI appearance is not diagnostic, kinetic flow curves from gadolinium-enhanced dynamic contrast MRI have been proven quite useful for differentiating cancer from a benign lesion [25-27, 34-37], incorporated herein by reference. Kinetic curves can be interpreted by visual analysis; however, computer software programs facilitate their use.

The appearance of the contrast time-flow curves has been well described by Kuhl [25-27] and others (FIG. 6, FIG. 7, FIG. 8A-8B and FIG. 9) for benign and malignant lesions. According to Kuhl, cancer has two characteristic appearances, i.e. the rapid contrast spike and the appearance of the outflow curve.

The rapid enhancement spike is considered cancerous if the rapid early peak is 60% above the baseline (FIG. 2A-2B). Although there are only a few comments regarding the outflow curve of a spike, it is quite evident that the spike appearance depends upon rapid outflow (due to veins) as well as on rapid inflow.

Figure 6:
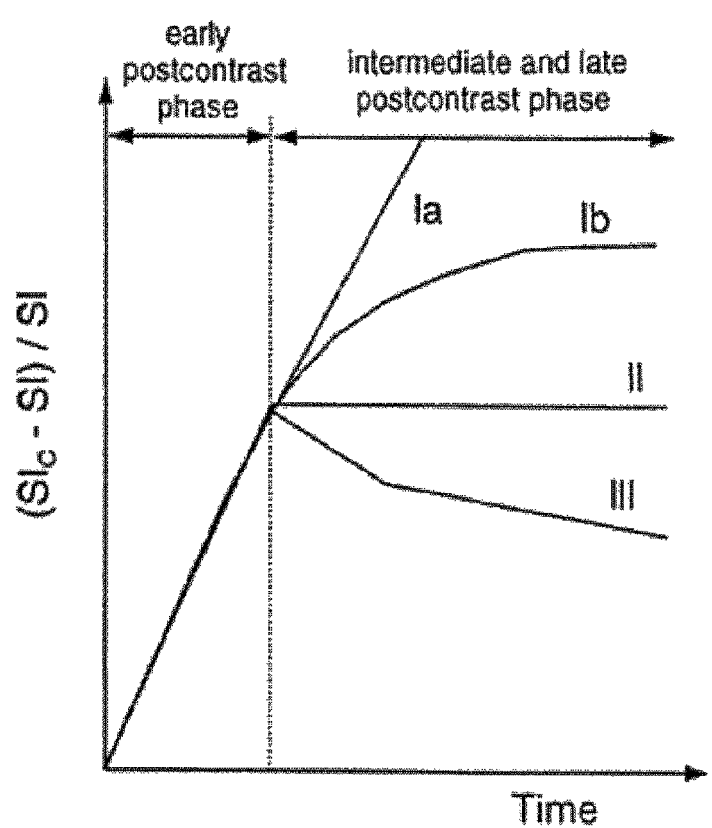
FIG. 6 shows that benign lesions typically have a kinetic curve which shows an increase or plateau flow, Ia and Ib. Cancer shows a decreasing "washout" type II and type III.
Figure 7:
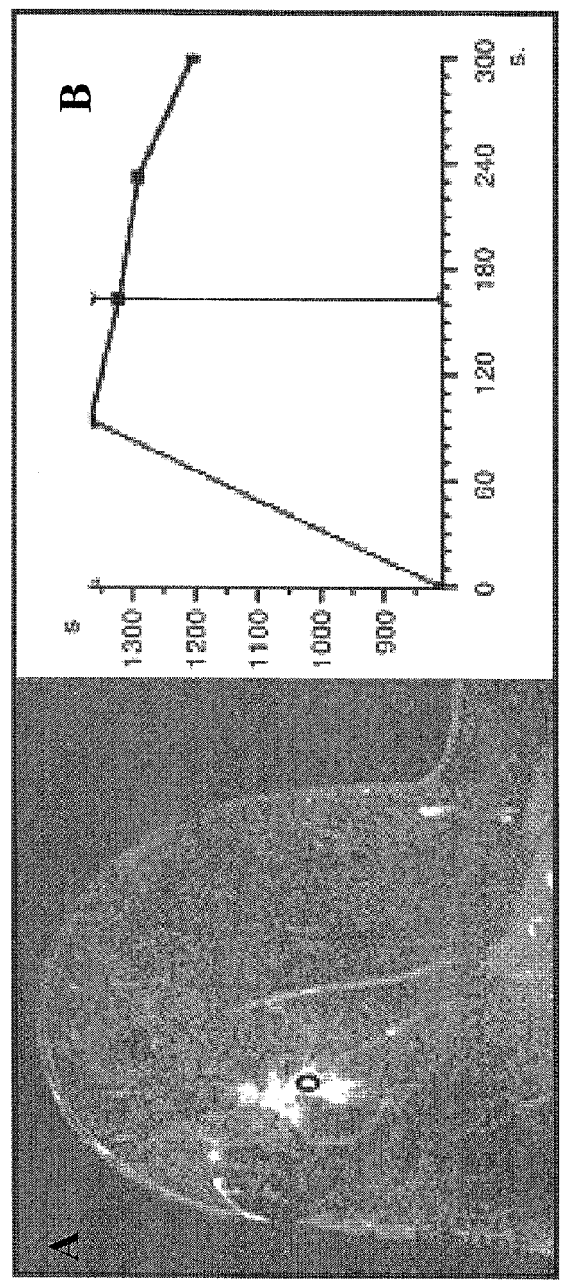
FIG. 7A and FIG. 7B show a region of interest (black oval on the left image) and corresponding time signal curve of an enhancing mass in the right breast, with an irregular shape, speculated borders, heterogeneous internal enhancement, and first initial enhancement followed by early washout.

When there is not a spike, correct diagnosis depends upon the shape of the outflow curve, which reflects venous drainage, (FIG. 6, FIG. 7, and FIG. 8A-8B). Benign lesions typically have a kinetic curve which shows an increase or plateau flow, Ia and Ib. Cancer shows a decreasing "washout" type II and type III, (FIG. 6). The outflow characteristics are determined by venous flow, permeability, and arteriovenous shunting [25-27, 38]. The steeper the outflow slope the more likely it is that there is cancer. For the best results, careful attention must be given to detail and the appearance of the kinetic curve; Comprehensive discussion of the technique should be reviewed in the article by Kuhl et al. [25-27], (FIG. 9).

FIG. 6 shows a schematic drawing of the time-signal intensity curve types. Type I corresponds to a straight (Ia) or curved (Ib) line; enhancement continues over the entire dynamic study. Type II is a plateau curve with a sharp bend after the initial upstroke. Type I is a washout time course Kuhl et al., [25].

FIG. 7a and FIG. 7b show a region of interest (black oval on the left image) and corresponding time signal curve of an enhancing mass in the right breast, with an irregular shape, speculated borders, heterogeneous internal enhancement, and first initial enhancement followed by early washout. The mass was determined to be Bi-Rads category 5, as the morphologic and kinetic criteria were both highly suggestive of malignancy Kuhl et al., [26].

Figures 8A, 8B:
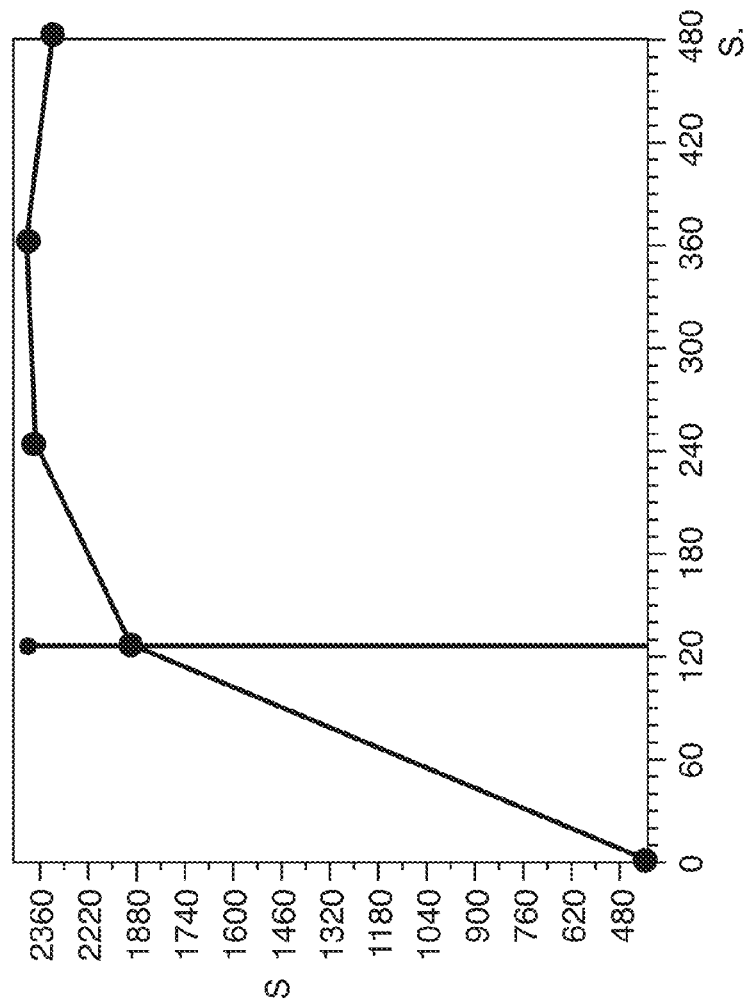
FIG. 8A-8B shows a Myxoid fibroadenoma.
Figure 9:
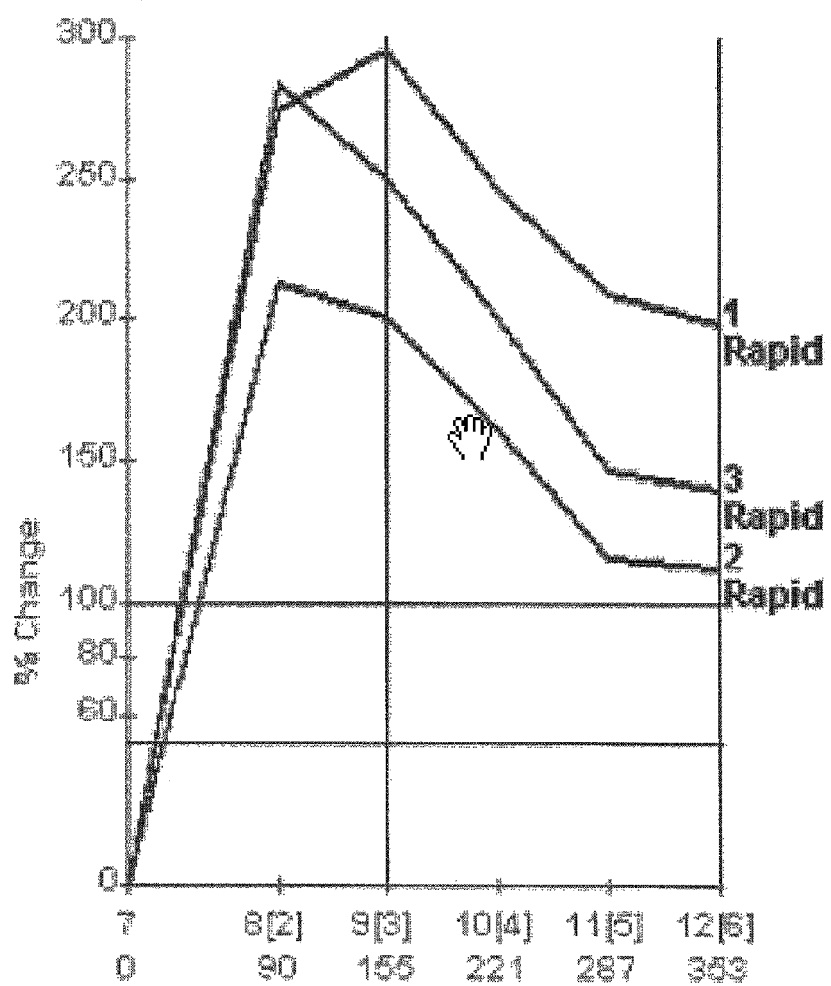
FIG. 9 shows a graph with three curves measured at different sites in the same breast cancer.

FIG. 8A-B shows a Myxoid fibroadenoma. (FIG. 8a) Region of interest (black oval on the left image) and (FIG. 8b) the corresponding time-signal intensity curve. The mass has a lobulated shape, smooth borders, heterogeneous internal enhancement with dark internal septations, and fast initial enhancement followed by persistent enhancement. The mass was determined to be BI-RADS category 2, as the morphologic and kinetic criteria were concordantly benign, Kuhl et al., [26].

FIG. 9 shows a computer evaluation of kinetic curves is more consistent and convenient. This graph shows three curves measured at different sites in the same breast cancer, and displaying some variability but still showing the characteristic cancer signature of rapid washout. Note that the inflow curve is quite steep, and it is because of the shape of the outflow that this is not a "spike." Spike enhancement also depends upon the venous outflow.

Figure 10:
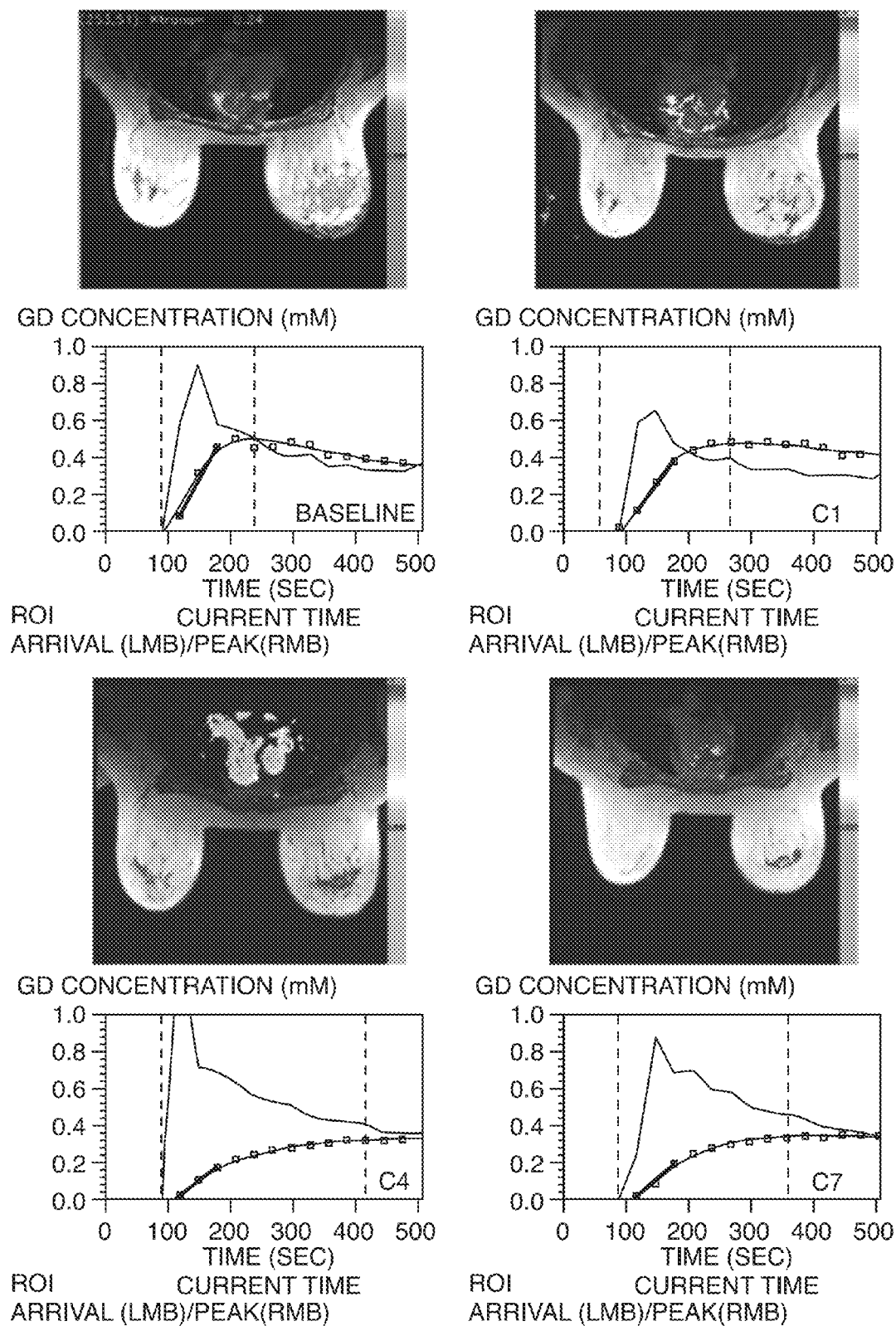
FIG. 10 shows changes in kinetic curves are also useful for assessing treatment response, as they show the early changes in the washout curve.

Changes in kinetic curves are also useful for assessing treatment response, as they show the early changes in the washout curve (FIG. 10). Kuhl et al. [25-27] stated: "As the earliest sign of response, a change of enhancement kinetics was observed (slower wash-in rate, absence of a washout pattern—ie, flattening of the enhancement curve), which preceded a change in tumor morphology by several weeks."

Permeability measurements have proven quite useful for the diagnosis and therapeutic follow-up of breast cancer. Radjenovic et al. [39], incorporated herein by reference, found, that "Parameters $k_{ep}$ and $K^{trans}$ were significantly higher in Grade 3 tumours than in low-grade tumours."

Figure 11:
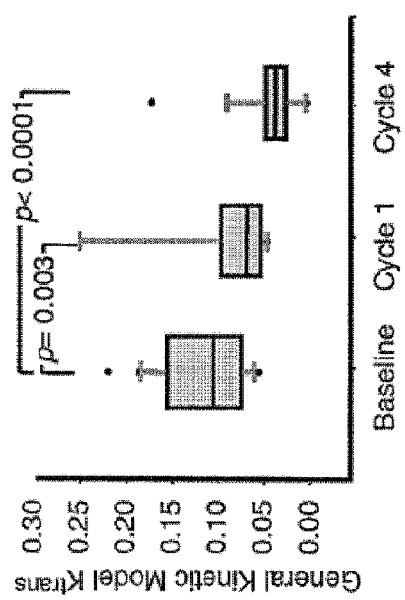
FIG. 11 shows MR imaging of breats and show the graphs illustrating the absolute decreases in $K^{trans}$ from the baseline to cycles 1 and 4.

When an untreated tumor shows increased permeability, anti-VEGF drugs change the permeability and kinetic curve [40-42], all incorporated herein by reference. Raatschen et al [40] concluded that, "The MR imaging-assayed acute change in vascular leakiness after a single dose of bevacizumab was an early, measurable predictive biomarker of tumor angiogenesis treatment response", (FIG. 11). Thukral et al. [42] reported that with effective treatment with bevacizumab, the permeability Ktrans and blood volume changes were statistically significant, (FIG. 11). Basic science reports by Jain [14, 15] and Boucher [43, 44], incorporated herein by reference, have confirmed that the increased permeability and interstitial edema are reduced by the effects of anti-VEGF.

Important to the ALPHA thesis is that the VEGFR receptor sites are producing permeability on the peripheral veins at the margin of tumors [20-25]. The location of the action sites of VEGF and anti-VEGF drugs on veins explains the increased incidence of the venous thromboembolism reported by Nalluri [11] and using anti-VEGF drugs.

FIG. 10 show a change in serial transverse GKM $K^{trans}$ parametric maps (calculated from the transverse T1-weighted spoiled gradient-echo sequence {8/4.2, 25° flip angle, 4-5-mm section thickness}) (images at the top) and in the gadolinium (Gd) concentration-time curves (graphs at the bottom) for one patient from baseline to cycle 7 (C7). Tumor enhancement in the involved breast can be seen in the following colors: Red and green indicate high enhancement, and blue indicates low enhancement. Gadolinium concentration-time curves show the rate of gadolinium-based contrast material perfusion throughout the tumor. The blue line represents arterial input function (Alfn). ROI data, CI=cycle 1, C4=cycle 4, LMB=left mouse button, RMB=right mouse button Thurkal et al. [42].

FIG. 11 show the graphs illustrating the absolute decreases in $K^{trans}$ from the baseline to cycles 1 and 4. Two-sided P values were calculated with the Wilcoxon signed rank test (P=0.003 for the difference in $K^{trans}$ between cycle 1 and the baseline, P<0.001 for difference between cycle 4 and baseline). The horizontal line inside each box represents the median quartile, the horizontal line below the box is the lower quartile, and the line above the box is the upper quartile. The vertical lines connect the quartiles, Thurkal et al., [42].

Prostate

Early reports on the usefulness of MRI of the prostate, were less than enthusiastic [45, 46], incorporated herein by reference, although there have been subsequent reports of considerable success in both the localization and differentiation of normal from cancerous tissues [47-51], incorporated herein by reference. Blood volume and kinetic curves [52], incorporated herein by reference, have not been consistently helpful, although permeability characteristics are quite useful. Jackson et al. [47] indicated that "quantitative parameter maps showed a significant difference between the benign peripheral zone and tumour for the parameters $K^{trans}$, $v_e$ and $k_{ep}$."

Liver

Washout or rapid clearance of intravenous contrast material after the peak enhancement has proven to be a reliable indicator of malignancy. This interpretative sign has been used with ultrasound, CT, and MRI and depends upon the rapid clearance of contrast material through tumors as compared to through normal liver.

With microbubble-enhanced ultrasound, sources [53-57], incorporated herein by reference, reported that HCC could be characterized by delayed washout after early enhancement. Jang et al. [53, 54] used ultrasound with microbubble-contrast material to study 97 hepatocellular cancers. Jang et al. [53, 54] reported that 43% showed washout by 90 seconds, 26% washed out at between 91-180 seconds, and 22% washed out in 181-300 second period. Only 8% of cancers showed no washout and they were well differentiated HCC's.

Figure 12:
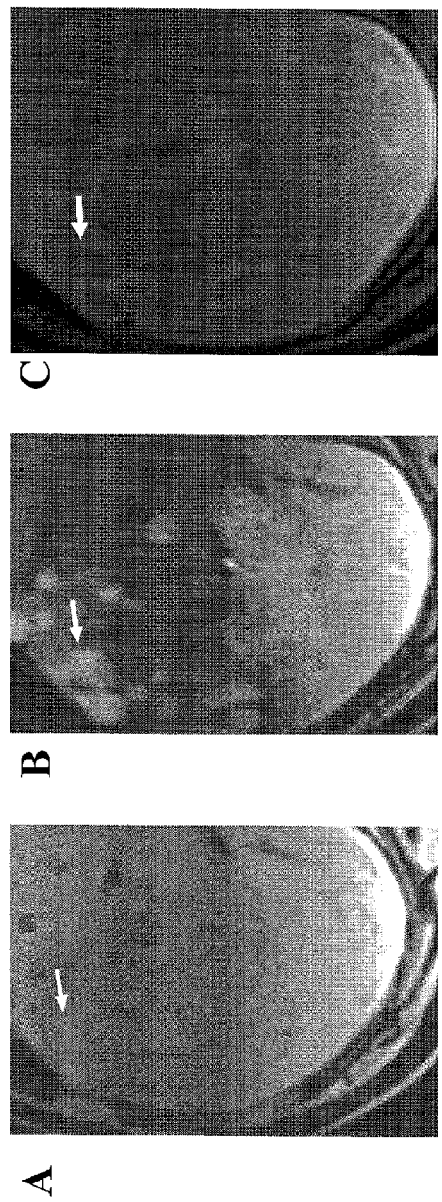
FIG. 12A-12C shows a gadolinium-enhanced MRI of liver metastases showing washout characteristic of malignancy.

Sources [58-60], incorporated herein by reference, reporting on gadolinium-enhanced MRI indicated that washout could distinguish benign and malignant lesions (FIG. 12A-12C). After studying 70 nodules, Ito, K. et al. (2004) [61], incorporated herein by reference, stated, "Rapid central washout after the early enhancement of the lesion and coronal enhancement surrounding the lesion are highly specific and diagnostic findings of small hypervascular hepatocellular carcinomas."

FIG. 12A-12C shows a gadolinium-enhanced MRI of liver metastases showing washout characteristic of malignancy. FIG. 12A. shows multiple subtle small masses (arrow) before enhancement. FIG. 12B. During gadolinium administration, these lesions showed increased enhancement. FIG. 12C. The lesions showed contrast washout at 70 seconds after contrast injection.

Multiple sources [62, 63] using MDCT reported the value of the washout sign. Lee et al. [63] reported, "Both subjective and objective washout correlated with an elevated alpha-fetoprotein level (p=0.01)."

Re-Examination of Seminal Gimbrone/Folkman Vasculogenesis Report

Finally, retrospective review and reinterpretation of the original vasculogenesis report by Gimbrone and Folkman [4] reveals inconsistencies (FIG. 4A-4B). Case Western Reserve Engineering school scientists, Dean and Professor Norman Tien and Professor Vera Chankong, re-analyzed all of Gimbrone's published 10 experiment data set, relative to the single "representative" graph from one animal. Tien and Chankong concluded with 95% certainty that the initial rapid tumor growth preceded arterial flow by at least one day.

Figure 13:
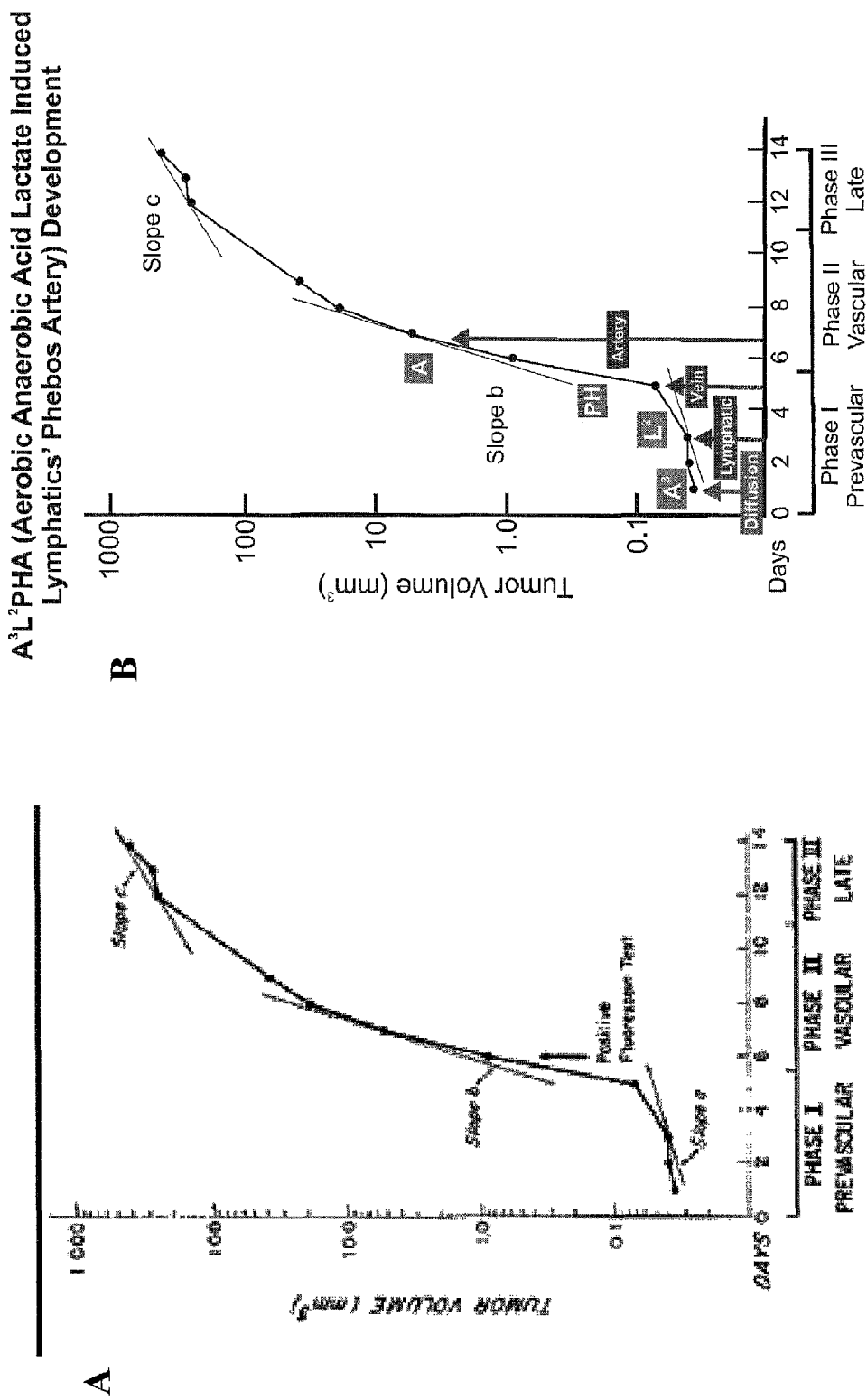
FIG. 13A shows characteristic growth curve of an iris implant (BP No. 29R) plotted on a semi-logarithmic scale.
FIG. 13B. Diagram shows an overlay over the original Gimbrone diagram illustrating the ALPHA concept.

FIG. 13A shows "The characteristic growth curve of an iris implant (BP No. 29R) plotted on a semi-logarithmic scale. Positive fluorescein test on day 6 represents earliest evidence of perfusion of the tumor and coincides with the beginning of exponential volume increase. Slopes "a," "b,", and "c," corresponding to prevascular, vascular, and late phases of growth, are indicated." Note the arrow indicating the arterial flow occurs after the rapid growth is initiated, Journal of Experimental Medicine, 1972; 136, p. 261-76 [4]. As discussed, statistical analysis of ten data sets, published but not used in this single graph reveals initiation of rapid tumor growth preceded arterial flow by at least one day. Therefore, the cause of the interruption of dormancy and growth cannot simply be elimination of hypoxia by arterialization.

FIG. 13B. Diagram shows an overlay over the original Gimbrone diagram illustrating the ALPHA concept. The contention being described herein is that the dormancy can only be explained by high lactate levels which may exist with or independent of hypoxia via aerobic glycolysis (glycolysis occurs in inflammatory, immune, or cancer cells even in normoxia). When high lactate levels produce dormancy reduction to moderate levels by lymphatics and veins interrupt tumor dormancy. As will be noted later, lymphatics and veins develop before arteries [20].

III. Cancer Metabolism: Energy Production, Waste Management, Glucose and Oxygen Availability, Disadvantages and Advantages of Aerobic and Glycolytic Metabolism Cancer consumes glucose by aerobic and/or glycolysis (anaerobic) processes [64-67], incorporated herein by reference. Aerobic metabolism using glucose and oxygen occurs in mitochondria while glycolysis using only glucose without oxygen occurs in the cytoplasm.

Warburg [66], Pederson [67] and others have reported that glycolysis is the preferred metabolic path for cancer. Pederson [67] noted that even in normoxia 50% of cancer metabolism can be from glycolysis and is even greater in hypoxia.

Benefits of glycolysis and lactate are numerous. Glycolysis stimulates the production of critical substrates for cell proliferation (such as pentose from PPP pathway, acetyl-CoA, NADH). Acidic lactate 1) creates a selective adaptive environment which kills normal cells and selects cancer clones with specialized waste enzymes (carbonic anhydrase IX, CAIX), monocarboxylic transporter 4, MCT4), 2) induces hyaluronan which a) activates motogenic genes by cell membrane attachment and TGFb, b) hyaluronan stabilizes the mitotic spindle so aberrant clones can replicate, c) hyaluronan gradient aligns lymphatic endothelial cells via LYVE-1, a hyaluronan receptor, 3) induces TGFb which activates metalloproteases (Bauman 2009)[68], 4) Combination of MCT4, hyaluronan dependent molecule CD147 (Tang 2004 [69], Le Floch 2011 [70]) activates anti-apoptotic pathways including NFkB (Brown 2008 [71]), 5) acidic lactate releases VEGF and FGF from heparin sulfate and induces NFkB vasculogenic cytokines. (Brown 2008 [71]) 6) lactate induced specific cytokines 17/23 induce VEGF (Shime 2008 [72]) 7) induce COX2 stimulating VEGFC/D and cancer supporting prostaglandin E2.

Energy and Waste Production

Metabolism of glucose in normal and cancerous tissues occurs by two pathways, glycolysis and aerobic metabolism. Glycolysis creates ATP energy and pyruvate from glucose without oxygen. In the normal state, pyruvate moves into mitochondria to be processed with oxygen through the Krebs cycle. In the cancerous state, most pyruvate does not enter the Krebs cycle but is predominantly changed into lactate. In the cancerous state, the lactate feed back controls are altered and all pyruvate is completely converted into lactate by the cancer enzyme lactate dehydrogenases A [63]. The excessive lactate is detrimental to normal cells but cancer cells are unaffected because of specialized enzymes which protect the chemical balance of cancer cells.

Advocates of the current angiogenesis theory infer that the aerobic pathway should be preferred because of the efficient use of glucose, but Warburg [66] and others have confirmed that glycolysis is the preferred metabolic pathway for cancer. While glycolysis is chemically inefficient, it suits cancer well because its reaction speed is 100 times faster than aerobic processes and can generate ample energy. Very high lactate levels may cause cancer cell dormancy, but moderately high levels provide many benefits as noted below.

Taking a different perspective in examining the energy and waste production by the two metabolic pathways, a different teleologic rationale for angiogenesis related to glycolysis can be proposed.

With aerobic metabolism, one molecule of glucose and one molecule of oxygen produce 38 ATP's and C02 molecules. Glycolysis uses one molecule of glucose and no oxygen to make 2 ATP's and 2 lactates. Assuming a cell needs 38 ATP molecules to sustain life, a cancer cell would require 19 molecules of glucose and no oxygen to produce 38 ATP's which would also create 38 lactate molecules.

From this perspective and data, it is difficult to accept the current teleologic rationale that cancer angiogenesis is intended to grow arteries for improved oxygenation. The more logical teleologic rationale would be that if cancer has adequate glucose supply for glycolysis, its earliest immediate vascular need is to grow drainage vessels to remove the waste products rather than arteries to improve oxygen delivery.

Figure 14:
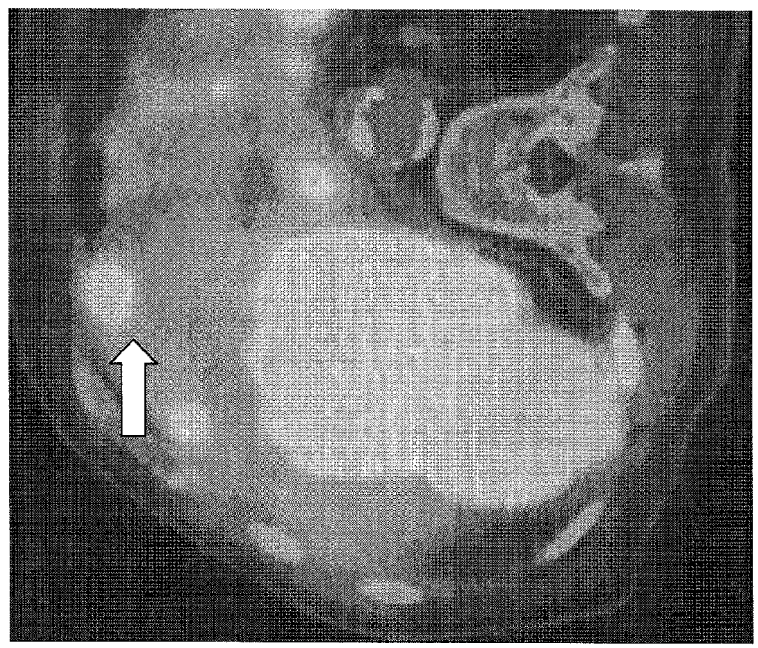
FIG. 14 shows FDG PET scan of metastatic colon cancer in the liver.

Cancer's increased requirement for glucose is clinically confirmed by the characteristic images produced by FDG (fluorodeoxyglucose) PET (positron emission tomography imaging. The rapid turnover of glucose appears as an increased signal indicating hypermetabolism, (FIG. 14). FIG. 14 shows a FDG PET scan of metastatic colon cancer in the liver. The lesions (arrow) show increased signal because more glucose must be processed for the same amount of energy, (see text).

Experimental and clinical reports confirm when both aerobic and aerobic metabolism are used by cancer, the overall metabolism is more dependent upon glucose than oxygen supply. Eskey et al. [73], incorporated herein by reference, elegantly confirmed the importance of glucose over that of oxygen for cancer metabolism. They used an animal model with an exteriorized tumor and separately varied the inflow of oxygen and glucose while they measure the effects on energy production. Energy production was directly related to glucose supply but not oxygen supply. Lui and Matsui [74], incorporated herein by reference, reported an interesting model which can be used to speculate further about glucose supply over arterial oxygen supply. In a mouse model, tumor cells were injected into an exteriorized live and observed with videomicroscopy. The first vessels to develop in the tumors was the portal vein, i.e. high glucose, followed later by the arterial system [74].

Clinical reports [75-78], incorporated herein by reference, confirmed the lack of correlation between oxygenated blood flow and energy in numerous PET studies. Vaupel et al. [79], incorporated herein by reference, reported lactate production is directly correlated with glucose uptake, as 40-85% may be released as lactate.

Adequate Glucose Supply is Provided without Normal Arterialization by Effective Diffusion and Active Glucose Transporters (GLUTS)

Certainly at the organ level, arteries are necessary to supply the inflow of glucose, but the movement of glucose across tissues and cells is quite efficient, without normal arterial supply. The effect of the increased distance between tumor and arteries on the supply of glucose and oxygen has been discussed by Gilles [80] and Gatenby [81], incorporated herein by reference. Gilles et al [80] reported (FIG. 14), that when the distance from arteries to tumors is more than 100-150 microns, the oxygen supply is restricted because of its poor diffusion. This hypoxia prevents aerobic metabolism.

Conversely, under the same circumstances the glucose supply is unaffected because of its favorable diffusion properties and active transport by glucose transporters (GLUTS). These up-regulated transporters are part of the metabolic adaptation (as well as waste enzymes) supported by HIF1a to initiate and support metabolic adaptation to glycolysis.

Figure 15:
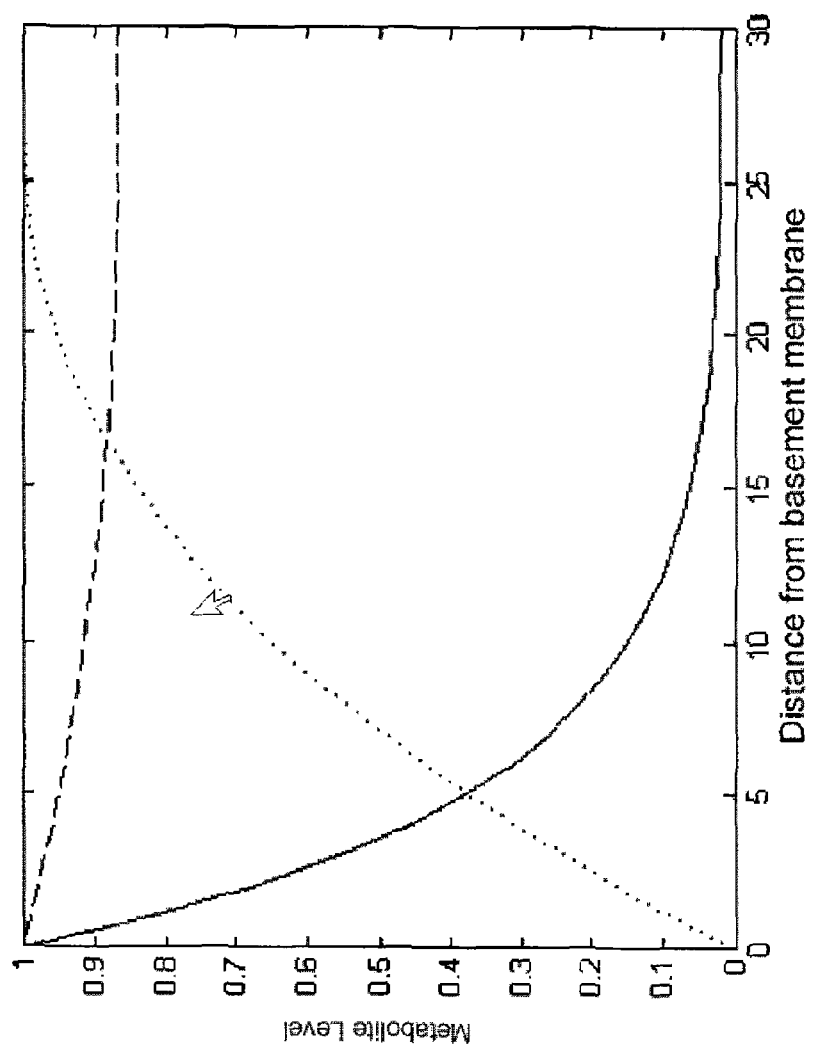
FIG. 15 shows substrate and metabolic profiles found in premalignant intraductal tumor using reaction-diffusion modeling.

FIG. 15 shows substrate and metabolic profiles found in premalignant intraductal tumor using reaction-diffusion modeling. Oxygen concentrations (solid line), glucose concentrations (dashed line), and H+ concentrations (dotted line) are shown, from Gillies and Gatenby, J Bioenerg Biomembr (2007) 39:251-257 [80], Depending Upon Concentration: Moderate Lactate Elevations Enhance Metastatic Properties and High Levels Induce Dormancy Although not generally recognized, molecular or drug effects can vary according to the concentration. An excellent clinical example is Dopamine, which affects blood pressure differently with different concentrations. Likewise, moderate or high elevations of lactate affect cancer cells differently. At moderately high levels, the neoplastic properties are enhanced and at very high levels, dormancy is induced. Whether dormancy is a positive or negative process depends upon the circumstances for the cancer cells.

Moderate Lactate Elevation/Low pH Provides Advantages for Cancer

If lactate is maintained at moderately elevated levels, there are advantages for cancer survival, proliferation and metastases. Moderate lactate levels create a locally hostile environment with low pH, toxic to normal cells to which, cancer cells can adapt by genetic mutation and survive [82], incorporated herein by reference. To ensure such adaptation, HIF has been recognized as critical for several dozen target genes that are transactivated by HIF-1 have been identified, including those encoding erythropoietin, glucose transporters, glycolytic enzymes, and vascular endothelial growth factor. The products of these genes either increase $O_2$ delivery or allow metabolic adaptation to reduced $O_2$ availability [83], incorporated herein by reference. While hypoxia is the best recognized inducing agent for HIF, other factors such as lactate [84, 85], incorporated herein by reference, and metabolic intermediates could increase HIF levels (see angiogenic mediators in FIG. 16).

Figure 16:
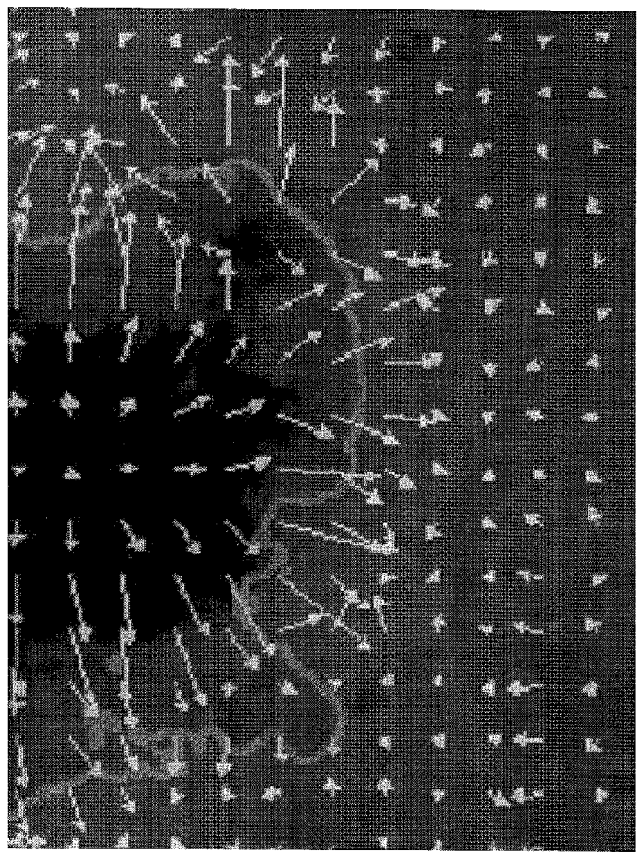
FIG. 16 shows a map of peritumoral H$^+$ flow using vectors generated from the $pH_e$ distribution around PC3N/Efgp.

FIG. 16 shows a map of peritumoral $H^+$ flow using vectors generated from the pH, distribution around PC3N/Efgp. The tumor is the darker region (left) and the tumor-host interface is drawn based on the GFP image. Arrows indicate the direction of $H^+$ (the steeper the gradient, the longer the arrow). Note the general flow of $H^+$ from the tumor core to its periphery, and from there, into the normal tissue, although there is significant heterogeneity, Gatenby, Cancer Research, 2006, vol. 66, May 15, 2006 [81].

Such clones possess specialized waste enzymes, such as carbonic anhydrase IX and lactate transporters increase the acidic environment, activating enzymes which enhance local invasion, FIG. 16. Unusual clones which might not be capable of normal mitotic division can successfully reproduce because the mitotic spindle is stabilized by the molecule hyaluronan which is induced by lactate [86], incorporated herein by reference, (FIG. 16).

Metastatic potential is enhanced by lactate because of numerous effects. Cancer cells and endothelial cells become capable of "locomotion" when the hyaluronan molecule (induced by lactate) attaches to the RHAMM receptor of the cell wall. This action signals the cytoskeleton to transform and produce the contractile protein actin [86] (FIG. 16). Lymphatic channels form from lymphatic endothelial cells with the unique biomarker hyaluronan receptor 1 (LYVE-1) Lymph cells under the influence of VEGF3, align according to the hyaluronan gradient (see later transformation section). Hamilton et al. [87], incorporated herein by reference, reported that hyaluronan sustained high basal motility in breast cancer. The large amounts of lactate produced increased interstitial fluid pressure which creates convective current toward lymphatic channels [88], incorporated herein by reference.

Figure 17:
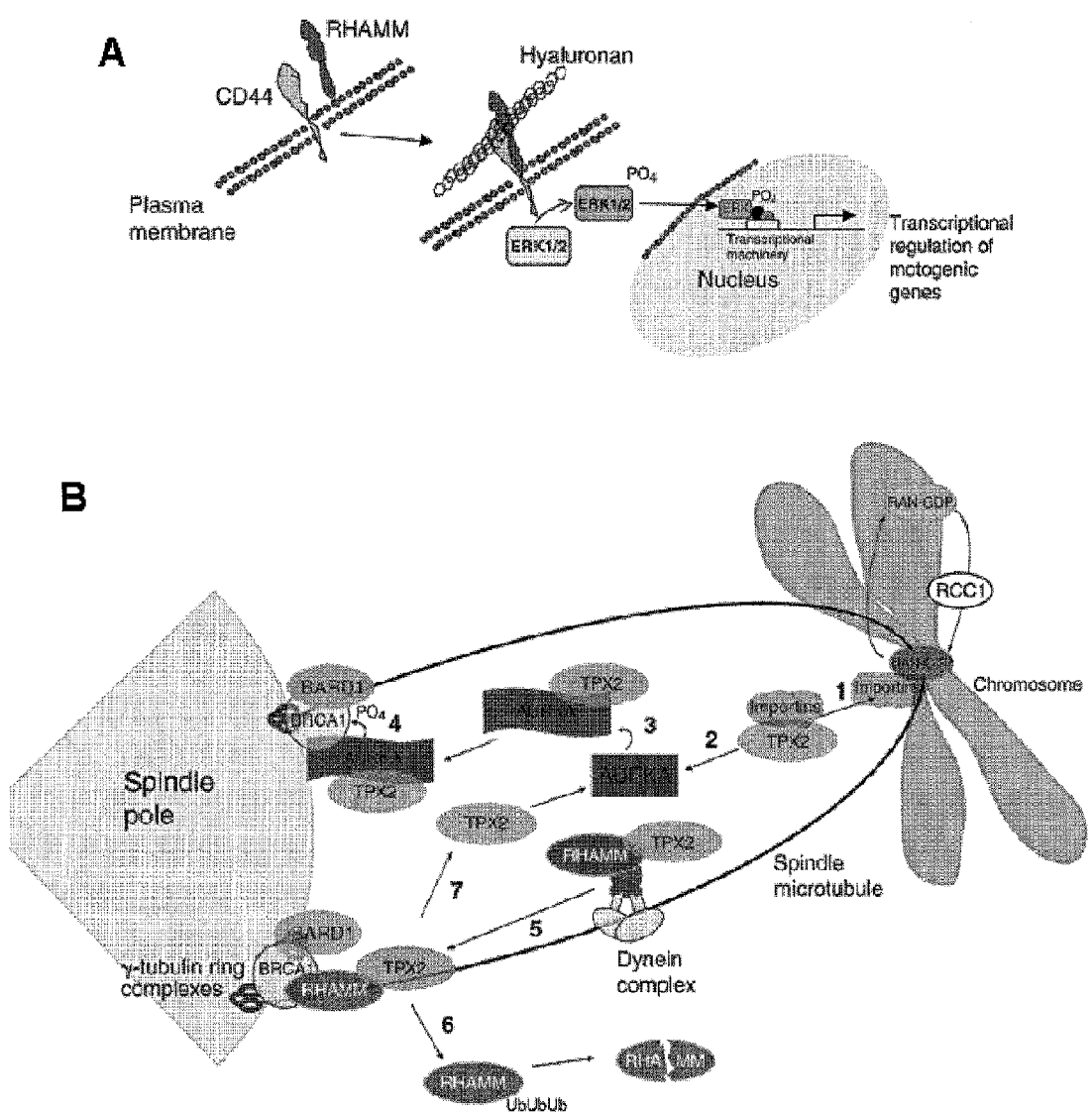
FIG. 17A-17B shows hyaluronan attaches to the cell membrane receptor, RHAMM, thus permitting transcription of motogenic genes.

FIG. 17A-17B shows hyaluronan attaches to the cell membrane receptor, RHAMM, thus permitting transcription of motogenic genes. Hyaluronan stabilizes the mitotic spindle, thus permitting more effective cell division and mitosis. Extracellular and intracellular functions of RHAMM are: (FIG. 17A) Cell-surface RHAMM promotes the activation of signaling cascades. Shown is one molecular mechanism for this. Cell-surface RHAMM, which is not an integral membrane protein, partners with CD44 and, in the presence of hyaluronan, activates ERK1/2 (indicated as phosphorylated ($PO_4$) ERK1,2), which results in the expression of genes that are required for motility and invasion. (FIG. 17B) In X, laevis egg extracts, a RAN-GTP gradient, which is established by chromosome-bound guanine nucleotide-exchange factor RCCI activity, is required for anastral mitotic-spindle assembly. RAN-GTP activity regulates the function of a number of mitotic-spindle proteins, including importins that then form inhibitory complexes with both spindle-assembly factors and TPX2. For example, by binding importins (indicated as step 1), RAN-GTP releases TPX2 (step 2), which is a major activator of Aurora kinase A (AURKA). TPX2 directly activates AURKA by protecting an autophosphorylated residue (step 3). AURKA, in turn, can phosphorylate ($PO_4$) BRCA1 to facilitate G2-M transition (step 4). Via an interaction with the dynein complex, RHAMM localizes to the spindle pole, at which it interacts with 7-tubulin (step 5). RHAMM also interacts with TPX2 and dynein, thereby having the potential to localize TPX2 to spindle poles (step 5). The BRCA1-BARD1 complex modifies TPX2 localization and spindle assembly by attenuating RHAMM function through ubiquitylation (Ub) (step 6). Ubiquitylation of RHAMM, and subsequently its degradation, probably releases TPX2 from the spindle pole (step 7), thus affecting AURKA activation and G2-M progression.

Tumor Dormancy

Dormancy of cancer cells is an inactive state from which tumor cells must emerge to grow, proliferate, and metastasize. Because interruption of dormancy has been the benchmark to judge effective vasculogenesis, a better understanding of its causative mechanisms is important. Because the traditional angiogenesis theory is derived from Gimbrone et al. inferring hypoxia causes dormancy and restoration of oxygen interrupts dormancy, it is interesting to note their direct statement [4]. Gimbrone et al. stated," "The mechanism of this population dormancy is not elucidated by these experiments." [4].

Surprisingly, direct data about hypoxia adversely reducing cancer cell activity leading to dormancy is not only lacking but there is abundant contrary information. Voluminous data indicates that hypoxia enhances the invasive metastatic process which is the essence of malignancy it does not retard such processes. As has been discussed, lactate that is produced by hypoxia produces lactate that enhances motility, mitosis, and local invasion as noted.

However, increased lactate levels, which is produced by cancer in either aerobic or hypoxic environment, has been reported to produce effects that would support dormancy, i.e. slowed metabolism, decreased proliferation, and anti-apoptotic effects. These data come from basis chemistry, simple cell culture experiments, clinical studies, and some specific signaling pathways.

If one considers the basic mass action dynamics of chemistry, the excess accumulation of an end product will decrease the forward reaction by mass action effect in reverse. Hence because cancer uses glycolysis, accumulation of lactate would decrease metabolic rate [89-93], incorporated herein by reference. Excess lactate impairs protein synthesis, growth and antibody production [88]. It also reduces cancer cell proliferation [90, 93].

Until this time, lactate was not evaluated as a possible cause of dormancy. Basic research has been down relative to the signaling pathways but there are a number which support this premise because lactate and glycolysis has been shown to prevent cell death by anti-apoptotic pathways. One of the major death pathways, FAS was reported by Erkilla [94], incorporated herein by reference, to be suppressed in germ cells by lactate. Erkilla [94] stated, "The final site of the death suppressing action of lactate appeared to take place in germ cells downstream of the FAS receptor activation." Thangarju et al. [95], incorporated herein by reference, studied the effect of lactate on the SLC5A8 trigger pathway for tumor cell apoptosis. Because this pathway depends upon pyruvate, they stated, "Tumor cells silence SLC5A8 and convert pyruvate into lactate as complementary mechanisms to avoid pyruvate induced cell death. The important inflammatory pathway NFkB is known to induce anti-apoptotic genes Bcl-3, IAP-1, and IAP-2 [71], incorporated herein by reference. Samuvel [96], incorporated herein by reference, reported that lactate boosts TLR4 signaling and NFkB pathway mediated gene transcription in macrophages. Also COX2 is up-regulated by NFkB and COX2 inhibits DNA damage induced apoptosis by p53 [97], incorporated herein by reference.

To understand causes of dormancy, changes in cell cycle control would need to be elucidated according to Blackstone [98], incorporated herein by reference. Rutz [99], incorporated herein by reference, noted "lactate interferes with mechanisms of cell-cycle control at two different points in the cell-cycle, depending on cell density and the resulting absence or presence of inhibition of cell proliferation. Interference with cell-cycle control may underlie the modification by exogenous lactate of radiosensitivity and postirradiation repair capacity in mammalian cells." Also several other papers suggest there might be a relationship between lactate and the chief regulator of cell cycle, pRb (protein retinoblastoma). Lactate induces and modulates both TNF (and TGFb, which have their own interaction) [100-102], incorporated herein by reference, which TGFb interacts with pRb [97]. If ALPHA is more completely investigated, perhaps other pathways related to cell cycle arrest will be elucidated. Glycolytic enzymes related to lactate and the Akt pathway is also known to inhibit apoptosis [98, 103].

There has been extensive study of tumor recurrence and its dependency on dormancy [71] but in clinically oriented reports there is an obvious lack of discussion about hypoxia. Blackstone et al. [98] extensively discussed tumor dormancy/recurrence and emphasized the importance of cell cycle pathways (no mention of hypoxia even after 40 years of study).

Other clinical reports are more consistent with lactate induced dormancy as it relates to cancer recurrence and treatments. Recognizing that dormant cells do not respond well to treatment, several sources have noted that treatment resistance may be associated with elevated lactate and that restoration of normoxia does not increase recurrence. Quennet et al. [104] and Sattler [105], both incorporated herein by reference, noted correlation between radioresistance and glycolysis and acidic lactate concentration. Feldmeyer [106] and Schonmeier [107], both incorporated herein by reference, dispelled the concern that tumor cells would be activated by restoration of normoxia by hyperbaric oxygen. Both sources found no increased local tumor recurrence as would be expected from the currently accepted concept that hypoxia causes tumor dormancy.

Lactate Level of Interstitial Fluid Modulated Predominantly by Lymphovenous Drainage and Partially by Aerobic Metabolism of Stromal or Cancer Cells After recognizing the cancerous processes controlled by elevated glycolytic lactate, in hypoxia (anaerobic) or normoxia (aerobic), the importance of maintaining appropriate levels can be appreciated. Increased glycolytic activity produces excessive lactate in the extracellular space producing increased interstitial pressure [108], incorporated herein by reference. This occurs because the 6 carbon glucose being split into two carbon lactate doubles the oncotic pressure. With convectional movement of free water [79] into the site hydrostatic pressure is produced stimulating flow into the lymphatics. Lactate levels depend predominantly upon the removal of lactate by the lymphatic and venous system.

Earlier studies by Gullino [88] on lactate reported that tumor interstitial fluid always had higher lactate than that of the inflow with the concentration being 25-100% higher. From baseline levels, the tumor levels increased until about 10 days when the levels were stabilized and maintained. Lymphatic drainage consistently measured 2-4 times that of tumor interstitial fluid. Studying a de novo squamous cell cancer model in mice, Eitchen et al. [109] verified that interstitial fluid was maintained by lymphatic flow. In the transition from normal to premalignant state, the host lymphatics dilated and increased in size due to the effects of VEGF-C. With the development of squamous cancer, the fluid increased and neolymphangiogenesis occurred, (see later Lymphangiogenesis section). Such lymphatics induced by VEGF-C are known to cause early local metastases [110, 111], both incorporated herein by reference.

The only incidental advantage of aerobic metabolism for cancer cells is indirectly related to lactate reduction by aerobically competent cells. When cancer cells retain mitochondria and oxygen is available, lactate is consumed, reducing local levels [112], incorporated herein by reference. Similarly, Kourakis [113], incorporated herein by reference, emphasized that adjacent stromal cells could reduce local lactate and pH levels, by metabolizing lactate.

Figure 18:
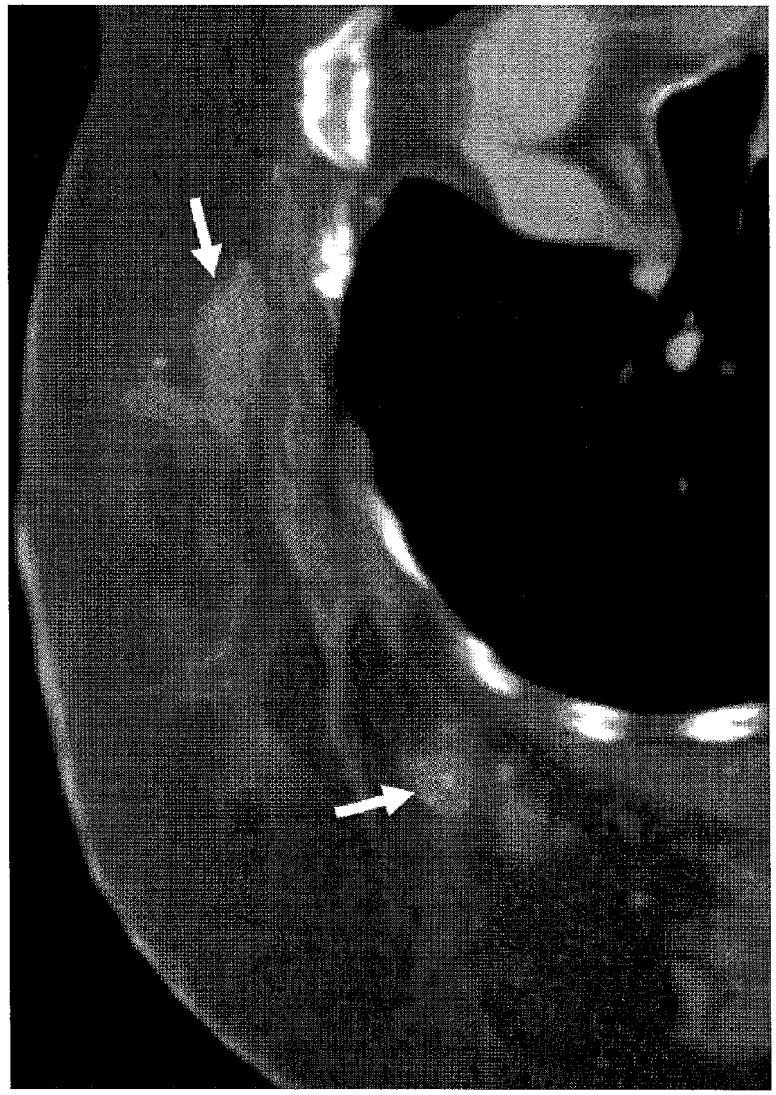
FIG. 18 show a CT scan showing a mass in the medial side of the breast, horizontal arrow as well as early metastases to small axillary node, vertical arrow.

FIG. 18 show a CT scan showing a mass in the medial side of the breast, horizontal arrow as well as early metastases to small axillary node, vertical arrow. Hyaluronan, which is produced by breast cancer, and fibroblasts stimulate cancer cell migration, and enhance mitotic activity and lymphatic development. Hamilton et al. [87] reported hyaluronan maintained breast cancer cell motility.

Lactate and Low pH Induce Vascular Growth Factors which Induce Lymphangiogenesis, Venogeneais, and Arteriogenesis As will be discussed in subsequent sections, virtually all of the angiogenic growth factors are released and/or produced by the effects of lactate and low pH. The processes include both the release of dormant growth factor in the microenvironment and production of new factors made by numerous cells. The stimulus for the production is the transformation of the microenvironment through numerous pathways most importantly through the TGF (transforming growth factor) by means of NFkB (nuclear factor kappa beta) pathway. The transformation includes endothelial cells, cancer cells, stromal fibroblasts and many immune cells.

There are No Real Advantages of Aerobic Metabolism for Cancer

The only incidental advantage of aerobic metabolism for cancer cells is that local lactate levels are reduced when adjacent aerobic cancer or stromal cells metabolize lactate [112-114], incorporated herein by reference. As discussed earlier, some sources refer to the chemical efficacy of aerobic metabolism but the fast reaction speed of glycolysis more than compensates to produce ample energy.

IV. Signaling Pathways, Vascular Growth Mediators, Action Site of Mediators for Lymphatics, Veins, and Arteries Signaling Pathways for Angiogenic Growth Mediators One of the most prevalent misconceptions supporting the current angiogenesis concept is that hypoxia is the sole mediator for VEGF and other vascular mediators. As will be discussed later, angiogenic growth mediators are induced by hypoxia but also many other pathways independent of the oxygenation level, i.e. normoxia, and hyperbaric oxygen. Among these other pathways lactate and low pH have been extensively discuss in the literature, especially in the early stages of angiogenesis and in wound healing.

Angiogenesis Growth Mediators are Induced in Hypoxia, Normoxia, and Hyperbaric Oxygen A most intriguing study by Heinzman et al [115], incorporated herein by reference, demonstrated that the production of many angiogenic growth factors is essentially equivalent in both hypoxia and normoxia. Cancer cells in hypoxia or normoxia produced almost equivalent amounts of angiogenic growth factors. Heinzman et al. [115] quantitated 11 angiogenic growth factors (VEGF, PDGF-AA, PDGF-AA/BB, IL-8, bFGF, EGF, IP-10, Flt-3 ligand, TGF-b1, TGF-b2, and TGF-B3) produced by different cancer cell lines in hypoxia and/or normoxia. Comparing the angiogenic products, they showed no or only a moderate increase of VEGF and no significant increase in bFGF in hypoxia. Of the other products, only IL-8 was generally higher and the levels in 8 of 11 mediators were closely correlated.

Hypoxic expression levels were generally higher than normoxic for IL-8 ($r^2>$ and VEGF ($r^2>0.60$), although only modestly. Heinzman [115] noted, "The degree of difference was surprising, as both IL-8 and VEGF have been reported to be up-regulated in response to hypoxic conditions." "It is remarkable to note that hypoxia did not increase bFGF compared to normoxia. Another in vitro study showed that bFGF was unaffected by hypoxia in cell lines" [116], incorporated herein by reference.

Reports regarding angiogenesis in hyperbaric oxygenation provide unique evidence indicating that factors other than oxygen levels are responsible for angiogenesis. In his study of squamous cell cancer, Schonmeyr et al. [107] observed that hyperbaric oxygen eliminated hypoxia and restored normoxia in squamous cell tumors. They unexpectedly found that with the restoration of tumor hypoxia to normoxia the amount of VEGF and vessel growth did not change compared to the preceding hypoxic state.

Signaling Pathways for Angiogenesis Include HIF (Hypoxia Induction Factor), Acidic Lactate and Other Pathways HIF-1a (Hypoxia Induction Factor) is the most important regulator for VEGF and FGF and well as most of the other enzymes which support glycolysis and the neoplastic processes. Although infrequently discussed, other processes affect HIF concentration. Of special note is that the increases of HIF can also be caused by non hypoxic intermediary metabolic imbalances [37, 72, 117-119], incorporated herein by reference. In addition to up-regulating angiogenesis, HIF is absolutely critical for adapting cellular metabolic processes to glycolysis associated with hypoxia or aerobic glycolysis [120]. In addition to up-regulating angiogenesis, HIF is absolutely critical for adapting cellular metabolic processes to glycolysis which is essential in hypoxia and also occurs with cancer it normoxia [114]. Interacting with cMyc, these include processes for substrate transport, expedited PPP pathways, rapid conversion of pyruvate to lactate and waste product management to maintain suitable cellular pH. These include enzymes involved with PPP cycle such as ketolases, glycolysis such LDHA, glucose transporters (GLUT I, II, IV), and waste enzymes carbonic anhydrases IX and XII, and lactate transporters MCT1,4 [83, 84].

The best described and recognized mechanism for controlling HIF concentrations is regulated by the degradation enzyme PhD (prolyl dehydrogenase). The enzyme increases in normal oxygen reducing levels and decreases in hypoxia to increase the HIF levels [83].

Less well known to most investigators is that HIF can be increased by non hypoxic intermediary metabolic imbalances [85, 121-123], incorporated herein by reference, and even low pH [124]. Lu et al. [122] stated, "with aerobic glycolysis (not aerobic metabolism but glycolysis in presence of oxygen), glucose metabolites can up-regulate HIF levels by preventing its degradation." McFate et al. [123] noted, "these data suggest that the buildup of glycolytic metabolites, resulting from high PDK-1 expression, may in turn promote HIP-1 activation, thus sustaining a feed-forward loop for malignant progression. 'Furthermore, Mekhail et al. [125], incorporated herein by reference, reported that as a result of the low pH induced predominantly by lactate, that "a decrease in environmental pH triggers the relocation of VHL (also degrades HIF), neutralizing its ability to degrade nuclear HIF even in the presence of oxygen."

Walenta [84] stated, "Demonstrating various biologic activities of lactate that can enhance the malignant behavior of cancer cells. These mechanisms include the activation of hyaluronan synthesis by tumor associated fibroblasts, up-regulation of VEGF and of HIF-alpha, and direct enhancement of cellular motility which generates favorable conditions for metastases."

Signaling Angiogenesis Pathways Other than Hypoxia and Waste Products

Recognizing the essential role of vasculogenesis for the success of tumors, it is no surprise there are many redundant vasculogenic pathways. Many diverse induction factors include hypoglycemia [45, 126], genetic anomalies i.e. VHL, PTEN, p53, RAS and oncogene [127-132], incorporated herein by reference. A complete discussion of these many factors is not possible nor is it relevant to the purpose of proposing an alternate angiogenesis concept to interrupt tumor dormancy.

Lactate and Low pH Increase Vascular Growth Mediators Independent of Oxygenation Level Although it is has not become widely known, there are many reports confirming that both lactate and low pH induce angiogenic growth factors. The origins of the acidic lactate are both macrophages and cancer cells which use glycolysis even when oxygen is present (aerobic glycolysis simply means oxygen is present with glycolysis). As noted above elevated metabolites especially lactate increases HIF as discussed above even in normoxia. When hypoxia occurs, even more acidic lactate is produced which likely acts in synergy with the HIF degradation enzyme PhD to elevated HIF further.

There are two mechanisms which increase local VEGF levels, the release of dormantly store VEGF and FGF [133-135], incorporated herein by reference, and the active production. First in early angiogenesis before hypoxia (see angiogenesis below) there is the release of dormant FGF and VEGF stored in the heparan sulfate matrix. In the later hypoxic phase the up-regulation of many other pathways occur from the effects of acidic lactate which is amplified and synergized by hypoxia.

It is odd that although many sources over many years have reported that low pH and lactate can increase vascular mediators, it has not become generally recognized [85, 100, 133-144], incorporated herein by reference. To amplify these facts and to forestall any concerns about paraphrasing errors, direct "quotes" are provided. If this exercise is tedious, the reader is invited to move to the next section.

D'Arcangelo et al. [133] reported "Acidosis Inhibits Endothelial Cell Apoptosis and Function and Induces Basic Fibroblast Growth Factor and Vascular Endothelial Growth Factor Expression.

Hunt stated [85], "Lactate, on the other hand is also a known instigator of cytokines and growth factors such as VEGF, TGF-β, and IL-1. Lactate stabilizes HIF-1α even in the presence of oxygen because lactate and pyruvate bind to and inhibit the HIF prolyl hydroxylases that would otherwise hydroxylate HIF-la and mark it for rapid degradation."

Fukumora et al. stated [134], "VEGF-promoter activity increased, with a decrease in pH and independent of $pO_2$." "VEGF transcription in brain tumors is regulated by both tissue $pO_2$ and pH via distinct pathways."

Xu et al. noted (140) that "acidic extracellular pH induces VEGF . . . via ERK1/2 MAPK signaling pathway." Kato et al. [137] stated, "Acidic pHe has also been shown to increase the expression of platelet-derived endothelial cell growth factor/thymidine phosphorylase, IL-8, and VEGF in varies types of cells."

Beckert [140] noted that "Lactate induces VEGF synthesis in endothelial cells and that this results in enhanced endothelial cell migration even in the absence of hypoxia." "Endothelial cells showed increased migration only when lactate was added in combination with endothelial cells" (it is now known lactate activates motogenic genes [86].

The emerging important role of cancer related inflammation and NFkB is enormous, which prompted Colotta et al. to call it the "seventh hallmark of cancer." As will be described below, these processes are part of a multi step process, which includes preangiogenic transformation of the microenvironment, early/incipient as well as delayed/maintenance angiogenesis.

Samuvel et al. observed, "Lactate boosts TLR4 activation and NF-κB-dependent inflammatory gene expression via monocarboxylatetransporters and MD-2 up-regulation." NFkB is the key orchestrator of innate immunity/inflammation and aberrant NFkB regulation has been observed in many cancers." Cytokines such as IL-1, IL-6, IL-8, and IL-23 are pro angiogenesis. IL-1 induces FGF2 [63] and VEGF. Mizukami et al. [117], stated "NFkB is induced by hypoxia specifically through accumulation of hydrogen peroxide when HIF-1 is blocked, and this compensatory pathway plays an important role to maintain angiogenesis in the absence of HIF-1 by up-regulating IL-8. Shime et al. [143] reported that lactate through NFkB induced IL-17, IL-23 which are proangiogenic inflammatory cytokines.

V. Modern Immunohistochemical Biomarkers Indicate that Target Receptor Sites of Vascular Growth Mediators Prior to 2000, it was believed that the lymphatic, venous or arterial character of vessels depended upon the nature, pressure and direction of fluid/blood flow. The development of specific immunohistochemical biomarkers combined with embryologic studies permits definition of the vascular mediator target receptor sites. Furthermore, retrospective review of earlier angiogenesis reports indicates early reports mistakenly labeled some venous structures as arterial. An excellent review of vascular specification was reported by Swift [119] in the journal Circulation Research provides valuable insights for reinterpretation of other reports.

Embryologic Origins of Vessels

The origins of the vascular and lymphatic vessels have been phylogenetically determined from tissue dissections and the immunohistologic biomarkers. Both the lymphatics and venous system evolve from the cardinal veins [120, 145], incorporated herein by reference. The arteries evolve from the dorsal aortas [119].

Figure 19:
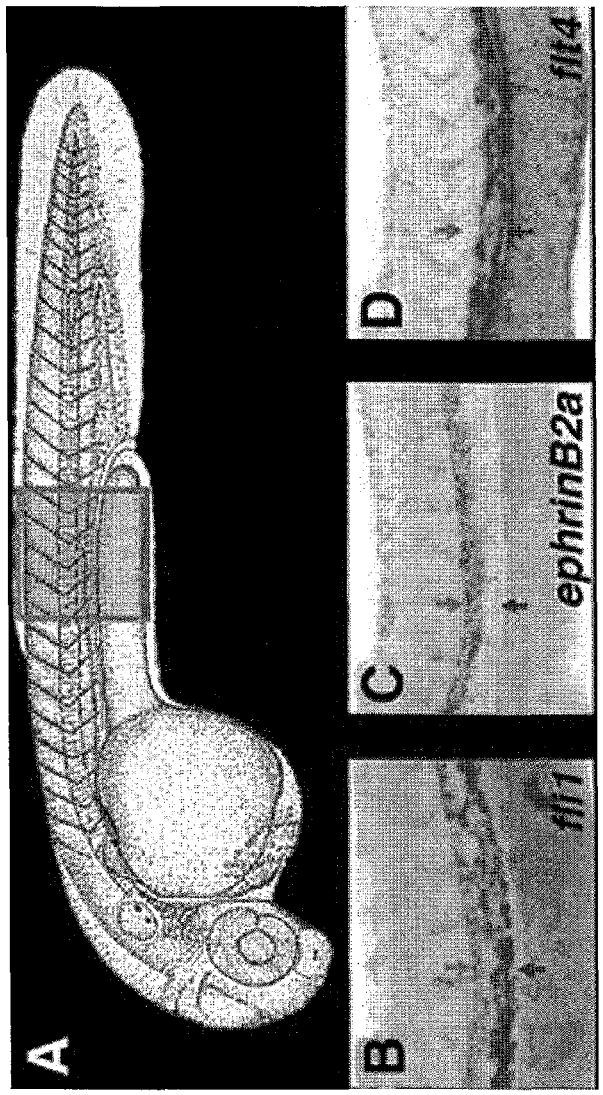
FIG. 19A-19D shows arterial and venous EC have molecularly defined identities that are evident before circulatory flow or even tubulogenesis.
Figure 20:
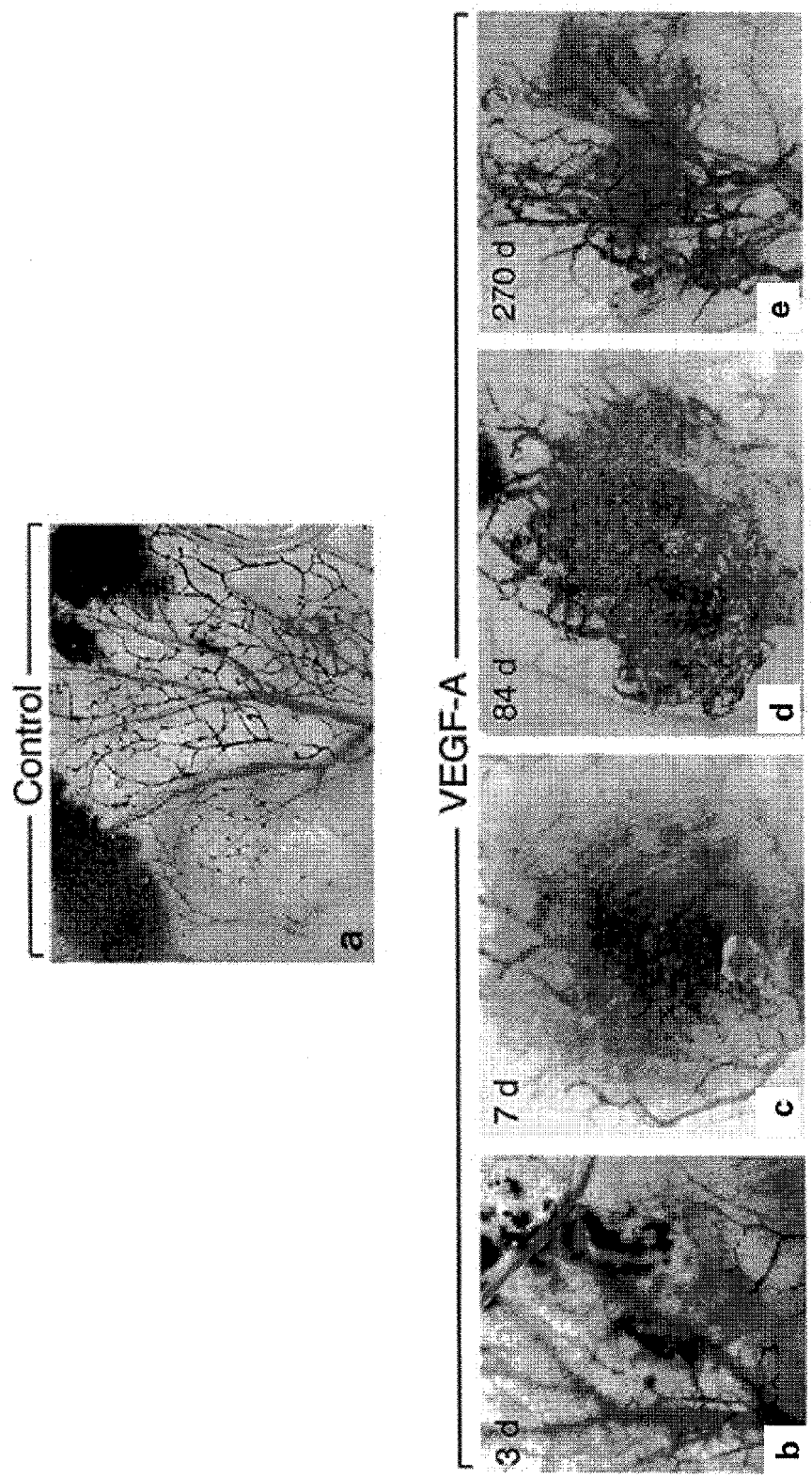
FIG. 20A-20E shows ear lymphatics after intravital infusion of colloidal carbon in a control mouse and in mice injected at the indicated intervals with Ad-PlGF or Ad-VEGF-A164.

FIG. 19A-19D shows arterial and venous EC have molecularly defined identities that are evident before circulatory flow or even tubulogenesis. Expression of artery markers such as ephrinB2a (FIG. 19C) and vein markers such as flt4 (FIG. 19D) is evident by in situ hybridization of 25 somite stage zebrafish embryos, several hours before circulation begins in the trunk. Expression of EphrinB2a within the dorsal aorta begins just as the migratory EC's arrive at the trunk midline from the lateral mesoderm and begin to aggregate into a cord of cells. FIG. 19B shows Expression of the pan-endothelial marker flt 1* is shown for the comparison. Box in upper diagram (FIG. 19A) shows approximate location of in situ images, for reference. Light arrows indicate dorsal aorta; dark arrow, posterior cardinal vein. * VEGFR-1 is receptor for VEGF-A, VEGFR-1 is significantly more enriched in veins during early embryologic vessel formation, but later is present in both arteries and veins (personal communication with Brant Weinstein, Director Molecular Genetics Laboratory. NIH). This is consistent with observations by Dvorak et al. who describe the first changes of transfected VEGF-A gene on blood vessels is on the venules.

Specification of Vascular Identity by Biomarkers

As a matter of record, specific markers for lymphatics, veins, and arteries have been defined and used in most of the studies referenced. The lymphatic marker is LYVE-1 (lymphatic endothelial cell hyaluronan receptor site-1). The venous markers are VEGFR1* (flt1), TIE-2, Ephrin 4, and COUP TF11. Both VEGFR1 and TIE-2 are very interesting in that these have been used by many sources and noted as being arterial markers [12, 146] when in fact they are associated with veins [147]. Moyon [147], incorporated herein by reference, showed that after seven days in the embryo, TIE-2 specifies veins. Earlier sources, such as Holash [146] assumed that TIE-2 receptor was the target site for angiopoietin was an arterial marker but this is not correct.

Also of note, according to Swift et al, the activation of PI3K/Akt pathway as commonly occurs in cancer, induces venous cell fate. PI3K promotes venous fate by suppressing NP1 and Notch gene activation [119, 148].

Using these biomarkers, numerous scientists have clarified the mechanistic action of the various growth mediators. Furthermore, because of the specificity of these markers, the sequence of vessel development can be accurately ascertained.

IV. Animal Models Studying Growth Mediators VEGF, FGF, Ephrin, and Others Support ALPHA Sequence of Vessel Development The vascular mediator receptor action sites and the observed sequential developmental changes in the vessels form an essential basis for ALPHA. As will be noted, the sequence of vascular changes occurs on the lymphatics, veins, and arteries.

VEGF A,-C,-D/VPF

The VEGF (vascular endothelial growth factor) family is the most important group of mediators for vasculogenesis, and consists of VEGF-A, VEGF-C, and VEGF-D.

VEGF affecting angiogenesis originates from two processes. Firstly, release of VEGF from a dormant form in the heparan matrix occurs during the early/initial phase of angiogenesis, see transformation section below. The initial elevation is from the release from the matrix by the effects of lactate, low pH, and induced inflammation [135, 136, 149, 150], incorporated herein by reference. As will be noted later, this may occur in hypoxia or normoxia [144, 151]. Secondly, VEGF is produced by tumor-associated cells occurs in hypoxia during the delayed/maintenance phase with other vascular growth mediators [71, 96, 144, 151].

In 1991, using immunohistochemical stains, Dvorak [20, 21] determined that the morphogeneic changes caused by VEGF-A is on the host veins adjacent to the tumor site. Dvorak [20, 21] stated, "Immunoreactive vessels (to VPF/VEGF antibodies) were venules and small veins." Kohn et al. [24] reported that the permeability of vessels occurred in the veins, and stated, "All tracers leaked primarily from venules and small veins at the tumor-host interface."

More recent sophisticated models using a transfected VEGF-A164 gene in a mouse model by Dvorak [20, 21] and Nagy [22, 23] studied the development of surrogate tumor vessels over a 128-day period. They reported that vessel morphogenesis occurred sequentially on lymphatics, Veins, and arteries (FIG. 20A-20E, FIG. 21, FIG. 22A-22C, and FIG. 23).

Figure 21:
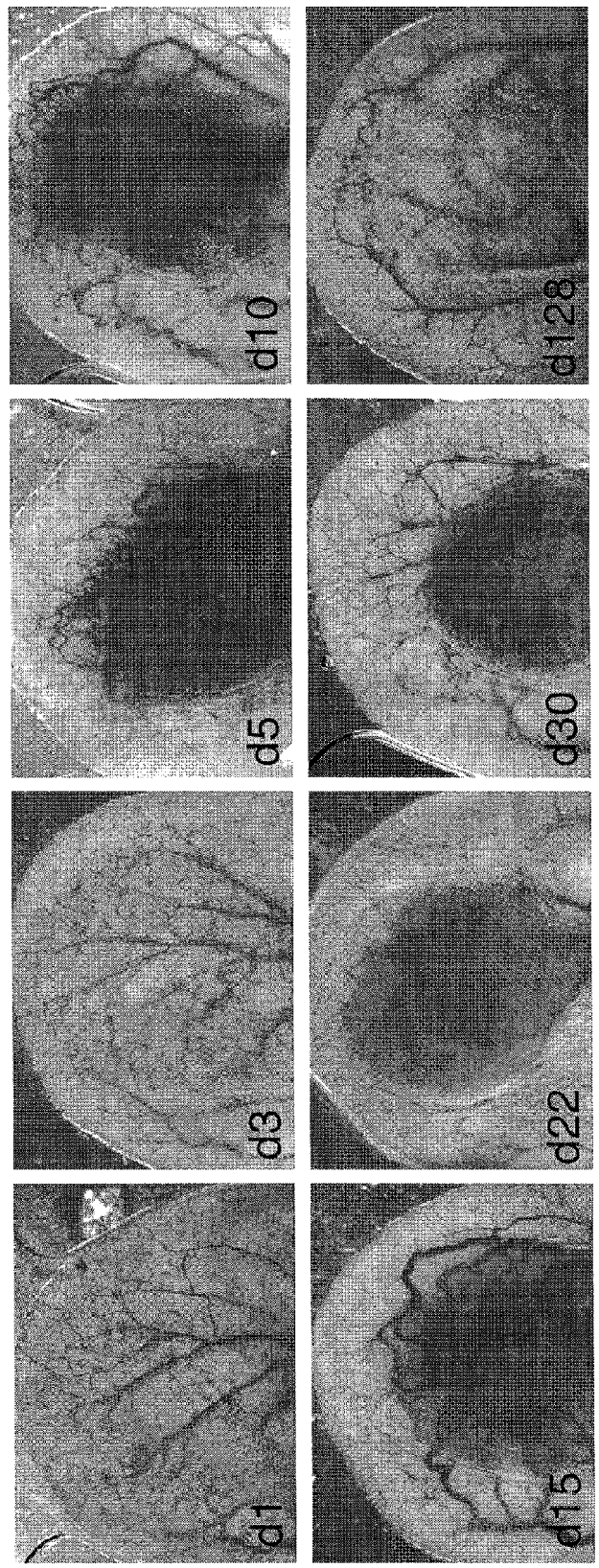
FIG. 21 shows angiogenic response to Ad-VEGF-A164 in the ears of nude mice at the indicated times and magnifications

Regarding lymphatic changes, these sources observed that dilatation of host lymphatics occurs 1-3 days before blood vessel changes occur [22, 23, 109] (FIG. 21). Nagy [22, 23] stated "Lymphatics at 3 days after Ad-VEGF-A are distended from dermal edema but have already enlarged further as the result of endothelial cell division and are transitioning into giant lymphatics." Eitchen [109] using a de novo skin squamous cell carcinoma showed lymphatics proliferated and dilated before blood vessels. Hong et al. [152], incorporated herein by reference, reported that the action of VEGF-A promoted wound-associated lymphangiogenesis by means of VEGFR-2 and integrins.

FIG. 20A-20E shows ear lymphatics after intravital infusion of colloidal carbon in a control mouse and in mice injected at the indicated intervals with Ad-PlGF or Ad-VEGF-A164. (FIG. 20a) Control ear. Multiple injection sites (black blotches at top) were required to fill the lymphatic network. Pattern of lymphatic filling in the ears of mice previously injected, as indicated, with Ad-VEGF-A164. Giant lymphatics are apparent as early as 3 days following injection (FIG. 20e) and persist through day 270. Kinetics of lymphatic filling in the ear of a mouse 84 days following injection with Ad-VEGF-A164. Nagy J A, Vasile E, Feng D, J Exp Med, vol. 196, No 11, 1497-1506, 2002 [23].

For lymphangiogenesis, VEGF-C and -D are specific and more effective than VEGF-A as they induce sprouting and lymphatic proliferation. Sato et al. [153], incorporated herein by reference, VEGF A attracted macrophages which in turn expressed VEGF-C and VEGF-D which induced new lymphatic formation. COX2 [154, 155], incorporated herein by reference, is up-regulated through the NFkB pathway induces VEGF-C production (Lactate initiates the induction of the NFkB inflammatory pathway [71, 100, 144, 151, 154, 155].) Enholm et al. [156] transfected the VEGF-C gene into a model showing its specificity for lymphangiogenesis.

Relative to the surrogate tumor blood vessels produced by VEGFA, Nagy [22, 23] stated "They arise from preexisting normal venules and are large, thin-walled, serpentine, pericyte-poor sinusoids that over express both of the VEGF-A receptor tyrosine kinases (VEGFR-1, VEGFR-2). MV (mother veins) then evolved into GMP and vascular malformations and also into structurally normal capillaries by a process of transcapillary bridging." Further Nagy said, "MV formed initially (1-5 days) and, from about 7 days, evolved into GMP (Glomeruloid bodies), vascular malformations, and capillaries." (FIG. 21, FIG. 22A-22C, and FIG. 23). It is interesting to note a similar time frame of the vessel formation as the 6.5 days in the Gimbrone experiment.

FIG. 21 shows angiogenic response to Ad-VEGF-A164 in the ears of nude mice at the indicated times and magnifications, from Nagy, J. A. et al. (2002) Cold Spring Harbor Symp Quant Biol 2002, 67:227-237 [157]

Figure 22:
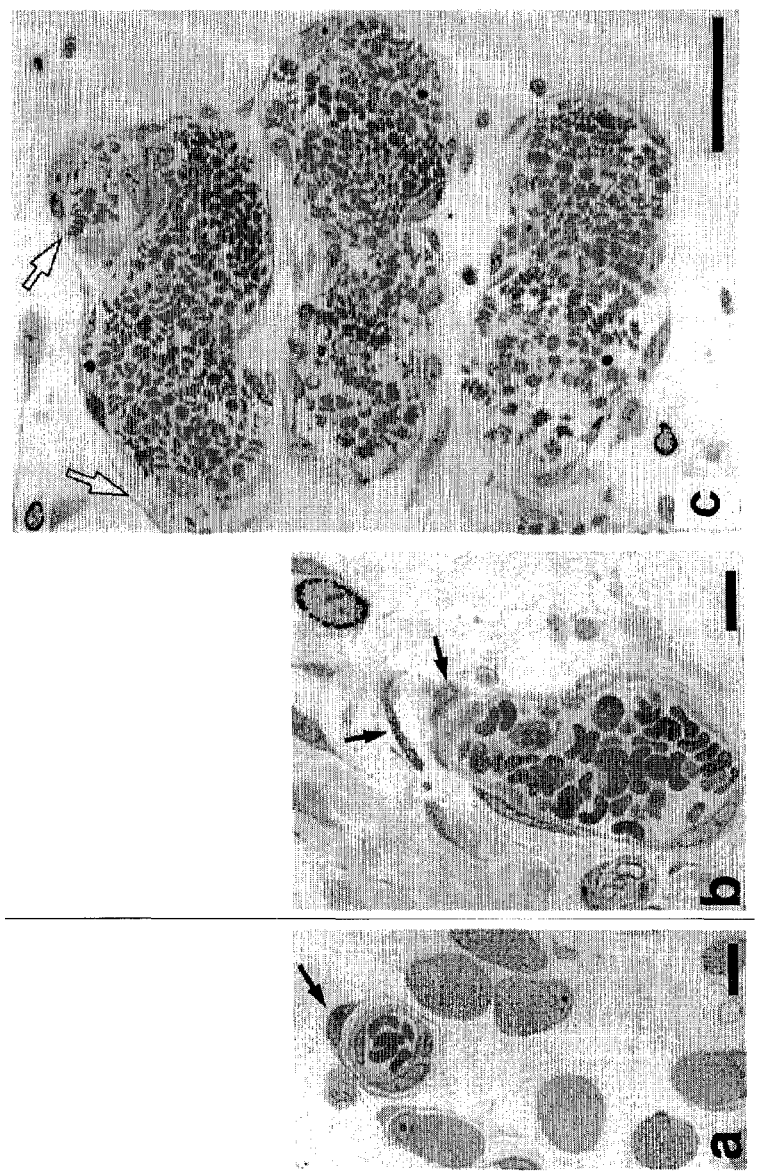
FIG. 22A-22C show vessels in ear skin at 18 hours after local injection of adeno-vpf/vegf.

FIG. 22A-22C show vessels in ear skin at 18 hours after local injection of adeno-vpf/vegf. FIG. 22a. Normal sized venule with slightly detached pericyte (arrow). Note the extensive edema separating adjacent muscle fibers. FIG. 22b. Evolving mother vessels illustrating striking vessel enlargement. EC (endothelial cell) activation (enlargement, prominent nucleoli) and pericytes (arrows) in various stages of detachment from vessels. FIG. 22c. Higher power magnification captures three sections through mother vessels, thus illustrating highly irregular luminal surfaces and EC (endothelial cell) bridging to form additional lumens (arrows) from Dvorak et al., Laboratory Investigation).

Figure 23:
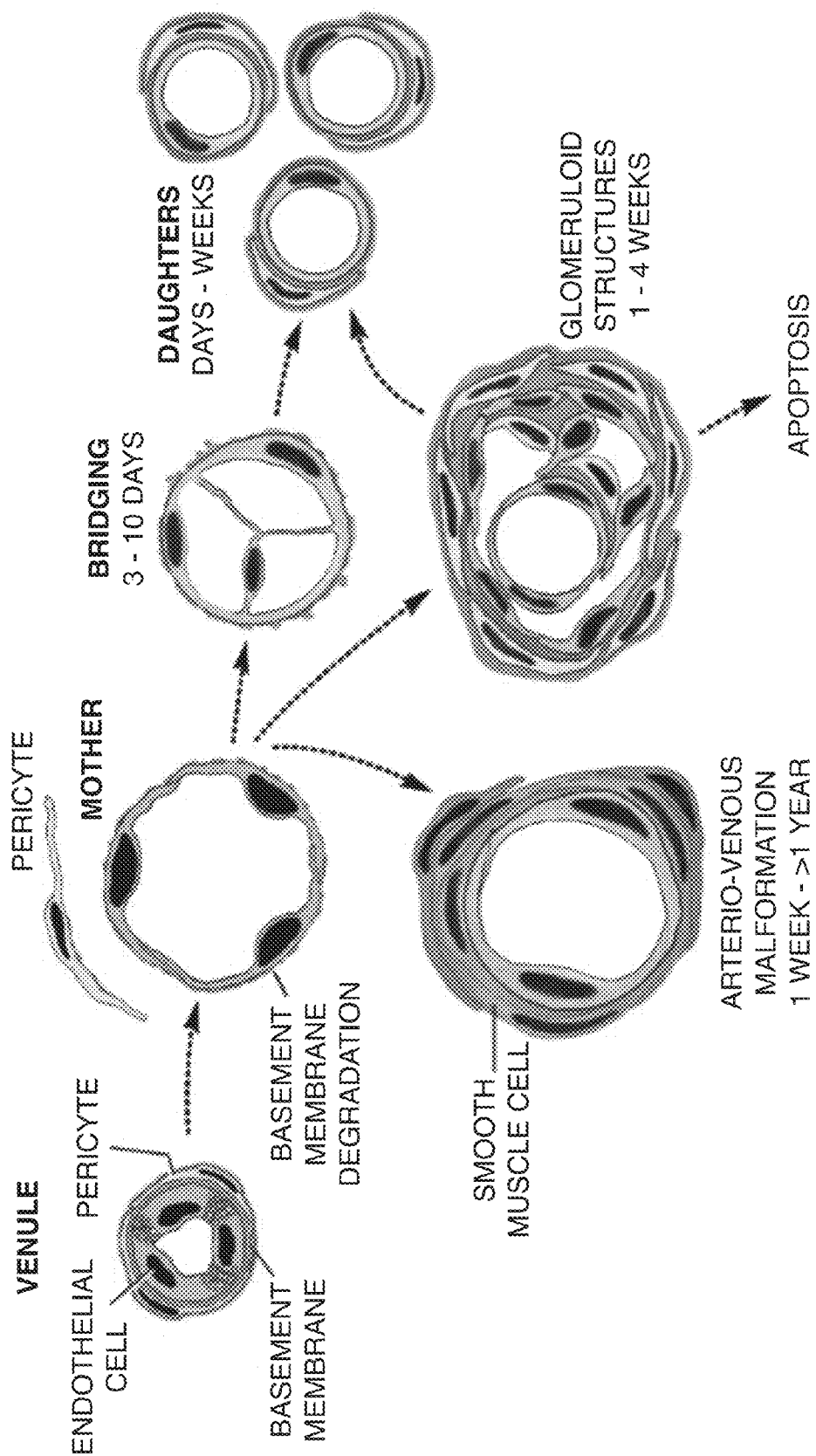
FIG. 23 shows a schematic diagram of mother vessel formation and evolution into daughter capillaries, vascular malformations and glomeruloid bodies.

FIG. 23 shows a schematic diagram of mother vessel formation and evolution into daughter capillaries, vascular malformations and glomeruloid bodies, modified from Pettersson, A. et al. (2000) Lab Invest, 80: 99-115 [158], incorporated herein by reference.

Fibroblast Growth Factor (bFGF or FGF2)

The FGF (fibroblast growth factor) family has two molecules, FGF2 (FGFb) and FGF1, although FGF2 is the more important and is typically referred to as FGF. FGF is produced by endothelial, cancer, stromal and inflammatory cells. As with VEGF, the local levels of FGF increase by the same two mechanisms, i.e. release from the heparan sulfate matrix due to the effects of waste products and the secondary production in the delayed/maintenance stage by a variety of cells.

Figure 24:
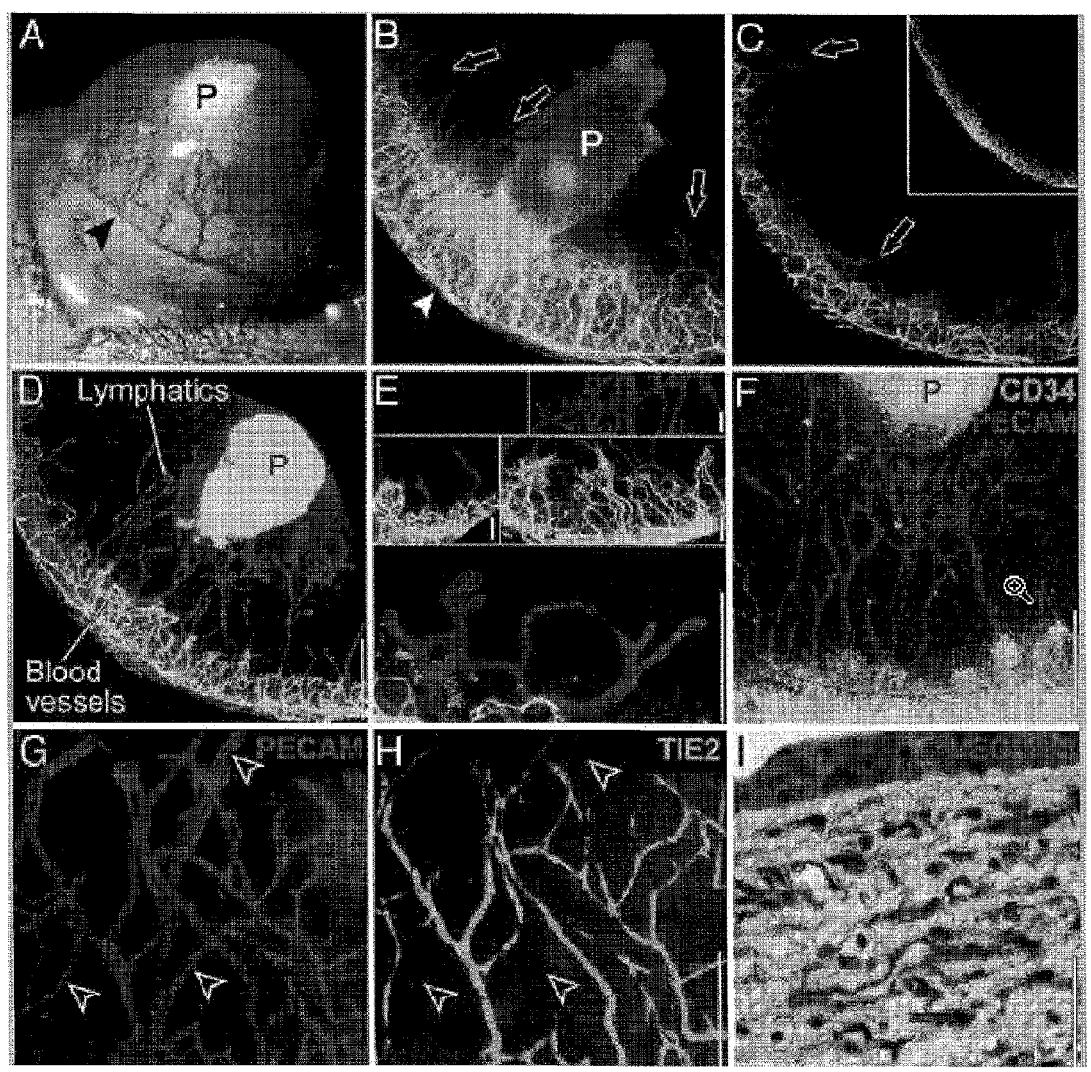
FIG. 24A-24I shows FGF-2 stimulates corneal lymphangiogenesis.

The primary action of FGF2 in the lowest concentration is the stimulation of lymphangiogenesis, while the secondary action is induction of VEGF A, C, and D via the promoter element API. Chang [126] said, "Low-Dose FGF-2 Selectively Stimulates Lymphangiogenesis", (FIG. 24). "Although the effects of 12.5 ng FGF-2 pellet are mediated through different cytokines, i.e. VEGF-A, -C, and -D, the predominant result is lymphangiogenesis."

FIG. 24A-24I shows FGF-2 stimulates corneal lymphangiogenesis. FIG. 24A. In the traditional corneal assay, 80 ng of FGF2 (P) stimulates blood vessel growth from the peripheral limbal vasculature (arrow). FIG. 24B The traditional assay is viewed under fluorescent microscopy after labeling blood vessels yellow-green and lymphatic vessels red, (arrow). Sucralfate in the FGF2 pellet autofluoresces green. FIG. 24C. At the opposite end of the cornes only lymphatic vessels sprout. Limbal vessels in the control corneas. FIG. 24D. Lowering the dose of the FGF2 pellet to 12.5 ng (P) and moving it farther from the limbus results in less angiogenesis, although lymphatic vessels still reach the pellet. FIG. 24E. Corneal lymphatic vessels were morphologically different from blood vessels. In additional corneal lymphatic vessels did not express CD34 (FIG. 24F) or Tie 2 (FIG. 24G, FIG. 24H) (arrow heads), but did express VEGFR3, (I), from, Chang et al., Proceedings of the National Academy of Science, 2004 [126].

Ephrin-2B, 4B

The ephrin family induced by hypoxia and HIF [159] affects the neovascularization processes [160, 161] after the early effects of VEGF. They are bidirectional markers. Ephrin-2B, an arterial marker, is the ligand for the downstream Ephrin-4B (venous receptor). The Ephrin-4b is enriched in veins as the principle functional partner for ephrin-2B [152]. When Ephrin-4B levels are high they reverse signal the Ephrin-2B to decrease arterial induction [161]. Hayashi [161], incorporated herein by reference, reported that VEGF had a stimulatory effect on ephrinB2 expression. Although this complicated feed forward/feedback process employs both Ephrin-2B and arterial marker and Ephrin-4b a venous marker, functionally the vascular development is based on the venous system. Hayashi et al. [161] stated, "An Ephrin-2B-rich environment was shown to induce neovascularization mainly through venous angiogenesis."

Angiopoietin

Angiopoietin 1 induces maturation of the newly formed vessels by increasing pericyte coverage and restoration of the basement membrane to its normal structure. Angiopoietin 2 blocks the angiogenic functions of Angiopoietin 1, Yancopoulos, G. D. et al. (2000) [162], incorporated herein by reference. Their receptor site, TIE-2 observed in early animal models was believed to be an arterial marker [146] but modern specification data confirms it is venous [119, 147, 162]. The most recent and definitive report was by Swift in Circulation Research (2009) [119] and emanating from the NIH Laboratory for Molecular Genetics.

Other Growth Factors Related to VEGF and FGF

There are many other angiogenic factors, which will only be discussed briefly for the sake of brevity. Most of these act or are formed by the actions of VEGF and FGF. These include platelet derived growth factor (PDGF), epidermal growth factor (EGF), IL-1 and others. Prostaglandins presensitize vessels to the effects of VEGF.

VII. Histopathology of Implanted Tumor Shows the First Vessel Ingrowth to be Venous Loops from Existing Veins Patan et al. [163], incorporated herein by reference, implanted human colon carcinoma into the ovarian pedicle of nude mice and permitted growth for 21 days. At 3, 7, 14, and 21 days, the tumors were harvested, and microscopic serial sections made, i.e. as many as 3500 serial histologic sections. At approximately seven days, they noted that vessel morphogenesis occurred in the small veins surrounded by tumor aggregates. They also noted venous loop formation, which began from larger veins in different tissue sites. The vessels were divided by intussceptive microvascular growth in the lumens as well as by segmentation.

Figure 25:
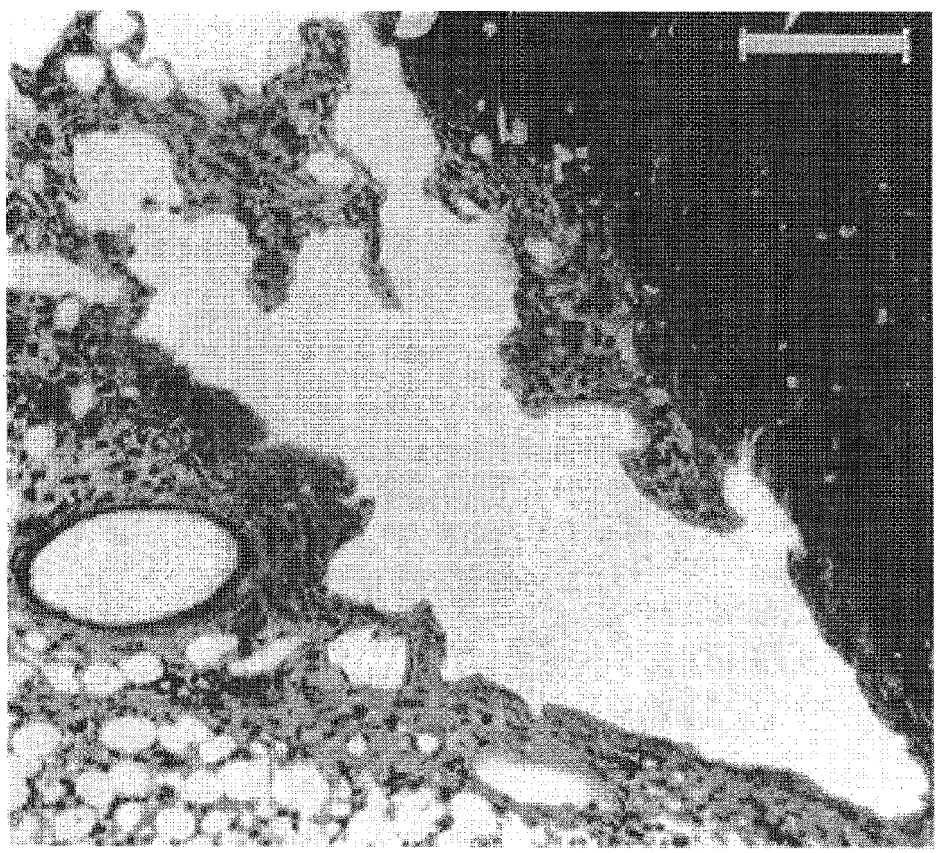
FIG. 25 shows an overview of the dilated main ovarian vein located close to the tumor margin (at the right) and near the ovarian artery (at the left).

Patan [163] stated, "Reconstruction of 3500 histological serial sections demonstrated that a new vascular network composed of venous-venous loops of varying sizes grows inside the tumor from the wall of the adjacent main vein." It should be noted that the source did not note any arterial changes in these dissections (FIG. 25). Dr. Patan verified that she saw no arterial morphogenesis in the study sections.

FIG. 25 shows an overview of the dilated main ovarian vein located close to the tumor margin (at the right) and near the ovarian artery (at the left). The venous lumen is divided by folds and ITSs, intussuceptive changes, arrows. A-L, from Patan et al., Circ. Res 2001, 89; 732-739 [163].

Vasculogenesis Models Document Sequential Development of Lymphangiogenesis, Phlebogenesis and Arteriogenesis Consistent with ALPHA The metabolic and signaling data discussed relative to ALPHA correlates well with observations from published animal models [109, 149, 150, 152, 164], incorporated herein by reference. In the medical literature, reports on blood vessel vasculogenesis were studied earlier than lymphangiogenesis because visualization of lymphatics in models was difficult because of their transparency. With the development of specific biomarkers, a more comprehensive appreciation of vasculogenesis is possible by collating the recent reports on lymphangiogenesis with earlier reports on blood vessel angiogenesis.

Lymphangiogenesis

The mechanisms and processes of lymphangiogenesis were recently reported by Eitchen et al. [109] using a de nova squamous cell cancer murine model. With these mice, skin lesions evolve over six months from dysplastic sites into squamous cell in situ and subsequently locally invasive squamous cell tumors. Eitchen et al. [109] quantitated the proliferation rate of lymphatic endothelial cells and blood vessels endothelial cells (it is not explained why stains were not use stains to differentiate veins and arteries).

Figure 26:
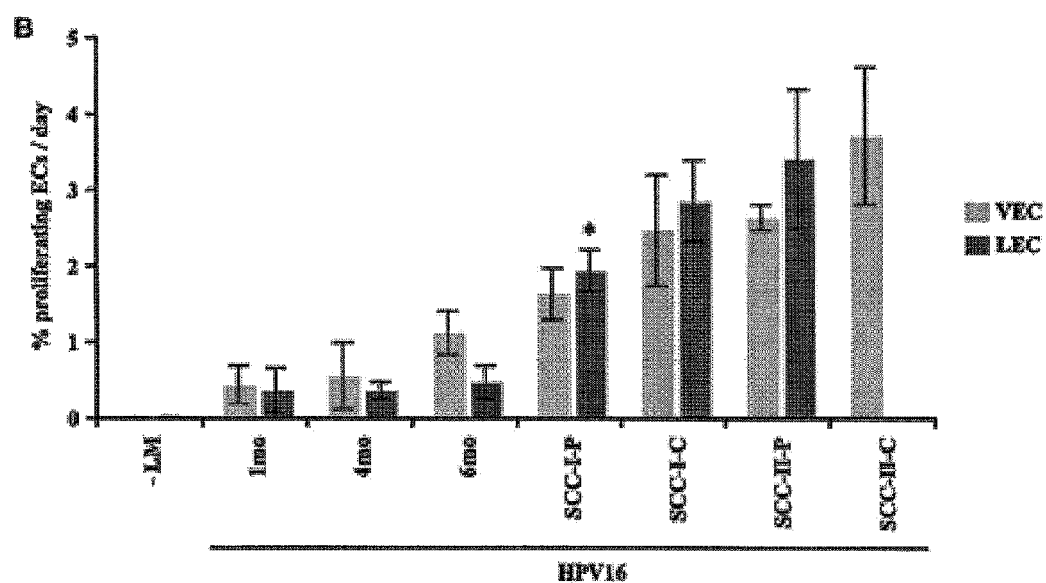
FIG. 26 show the rate of lymphatic endothelial cell proliferation is greater than that of vascular endothelial cells during the transition into the malignant form (SCC-I-P, SCC-I-C, SCC-II-P).

FIG. 26 show the rate of lymphatic endothelial cell proliferation is greater than that of vascular endothelial cells during the transition into the malignant form (SCC-I-P, SCC-I-C, SCC-II-P). VEC and LEC proliferation in premalignant and carcinoma tissue. Quantitative analysis of proliferating VECs and LECs in—LM, premalignant and carcinoma tissue. Proliferating LECs were identified in the periphery and center of well-differentiated grade 1 SCCs (SCC-1) but limited to periphery of less-differentiated grade 2 SCCs. Absence of open lumen lymphatic vessels SCC-II centers precluded analysis of LECs in that locale. *, P≤0.05, two-tailed unpaired nonparametric Mann-Whitney U test Dashed line, basement membrane. Blue staining, SYTO62-nuclear counterstain, Cancer Res, 2007; 67(11): 5211-20 [109].

The sequential vasculogenic changes observed Eitchen et al. confirmed that morphologic changes of lymphatics occur before blood vessel changes, FIG. 26. During the premalignant state, the proliferation rate of the lymphatic endothelial cells was less than the blood vessel rate, but increased dramatically when squamous cell carcinoma in situ developed. Lymphatics were abundant centrally and peripherally. As the squamous cell became less differentiated the center portion was devoid of open lumen lymphatics, but the peripheral areas had increased lymphatics. With blood vessel endothelial cells, they were present in both the center and the periphery in the less differentiated tumors. The phenotypic changes differed between blood vessels and lymphatics. The lymphatic vessels increased only in size and not density, while the morphogenic changes caused by increased diameter and number/density.

The same processes described by Eichten et al. [109] were manifested in the transfected VEGF/VPF DNA model described by Nagy and Dvorak [20-23] and shown in FIG. 18. They observed the earliest lymphatic changes induced by VEGF/VPF were dilatation of the host lymphatics. These changes occurred at 1-3 days, before there were subsequent changes in the veins and then arteries.

Eichten et al. [109] elegantly expressed the dynamic relationship between blood vessels and lymphatics. They noted that as the blood vessels become more permeable and leak into extracellular space during transition between the premalignant and malignant phases the excess tissue fluids are efficiently drained by the enlarged lymphatics balancing the fluid dynamics. As discussed earlier, cancer produces excess lactate in the extracellular space which stimulates hyaluronan forming lymphatics, which modulate amount of lactate laden extra cellular fluid [88, 108, 165, 166], incorporated herein by reference.

Blood Vessel Angiogenesis: Veins and Arteries

While there have been many vasculogenesis reports, most were published before the modern data was available. Rather than attempting to summarize than all and collate than with ALPHA, the discussion is framed around several reports by recognized investigators from only a few of the high quality journals, i.e. Journal of the National Cancer Institute [164], Proceedings of the National Academy [72], Cancer Research [150].

The primary report serving as the central discussion focus is by Li et al. [164] in the Journal of the National Cancer Institute, titled, "Initial Stages of Tumor Cell-Induced Angiogenesis: Evaluation Via Skin Window Chambers in Rodent Models." The uniqueness of this report is that they made numerous observations which were not understood at the time but in the light of modern data are completely consistent with the ALPHA concept.

The specifics of their experiment were as follows. A transparent window model in mice created and 20-50 cells were injected into the subcutaneous space. The cells were transfected with a green fluorescent protein so they were clearly visible during the morphologic angiogenic changes in the tissues. The tumor was observed for up to 4 weeks.

Figure 27:
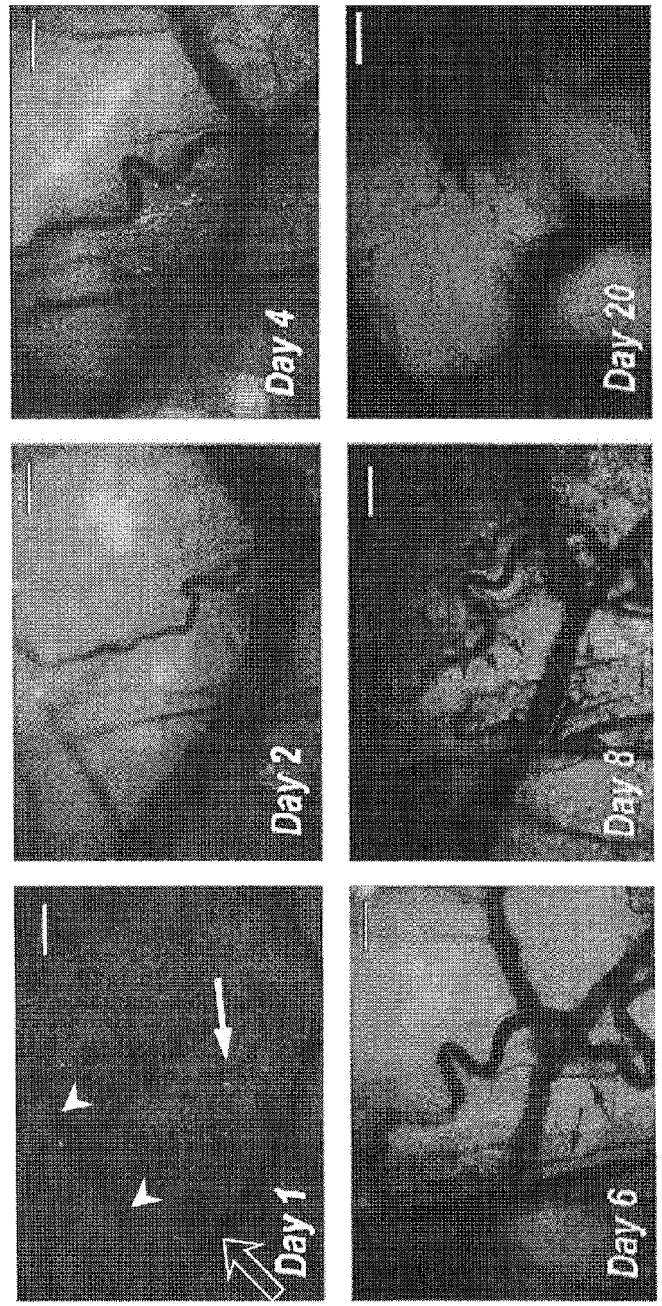
FIG. 27 shows the growth of a tumor from single 4T1 cells in a BALB/c mouse window chamber.

FIG. 27 shows the growth of a tumor from single 4T1 cells in a BALB/c mouse window chamber. Approximately 20 cells were injected in a BALB/c mouse window chamber and their growth followed serially after the initial implantation (white arrows on Day 1 indicate reference vessels seen on all images) which show references visible Red arrow in the day-2 panel indicates an elongated cell. Red arrows in the day-6 panel indicate dilated host vessels compared with the day-4 panel. Arrows in the day-8 panel indicate new microvessels. Pink arrows point to tumor (localized in the marked circle)-associated microvessels, and red arrows beneath the circled area point to dilated and/or tumor-induced vasculature outside the tumor. Size bars in the day-1 to day-8 panels represent 200 µm; size bar in the day-20 panel represents 500 µm, from J. Nat. Cancer Institute, 2000; 92(2):143-7 [164].

Li et al. [164] stated three phases for angiogenesis, FIG. 27: "1) the initial orchestration of tumor angiogenesis involved migration of tumor cells toward existing vasculature before neovascularization, Day 1-4. 2) Changes in surrounding microvessel structure, such as vasodilation and increased tortuosity, were seen at the approximately 60- to 80-cell stage of tumor growth, day 6-8.3) Clear demonstration of new vessel formation was seen at the approximately 100- to 300-cell stage of tumor growth."

Their observations that angiogenic changes occurred when the tumor cell masses were so small inferred that the tumor was not hypoxic because the cell number did not exceed $10^5$ cells or the overall size of 1-2 mm. They stated "Angiogenesis induced by tumor cells after implantation in the host begins at a very early stage, i.e., when the tumor mass contains roughly 100-300 cells." The variance with other sources discussing hypoxia and tumor size was noted but no cogent explanation was offered. As will be discussed later other sources [150, 167] have specifically stated this.

Their observation about, "Identification of chemotactic signals that initiate tumor cell migration toward the existing vasculature" indicates the activity of acidic lactate during transformation in the microenvironment. Although the causation of cell mobility and spindle configuration was not known at that time, it has since been proven that these changes can only occur by the lactate induction of hyaluronan in the tissues [86, 165, 166, 168, 169], incorporated herein by reference. Lactate is the only molecule which up-regulates the production of hyaluronan from fibroblasts, endothelial cells, and cancer cells [86, 165, 168-170] which is essential for motion and spindle shape. As mentioned earlier, hyaluronan produces these changes by attaching to specific hyaluronan receptor RHAMM on the cells membranes [86, 170], incorporated herein by reference. This attachment induces changes in the cytoskeleton, motogenic genes and mitotic spindle.

With transformation of the microenvironment, two processes which increase vascular growth mediators occur. VEGF and FGF have been found to be the essential growth mediators for the initial incipient angiogenic burst [149]. The low pH and lactate initiate early release of FGF and VEGF, which is stored dormantly [121, 122]. As previously discussed, dilatation of host vessels observed by Li et al. at Day 4-6, FIG. 27, is the first blood vessel change in blood vessels (after lymphatics) caused by VEGF [22, 23]. The second phase, delayed/maintenance neoangiogenesis observed at Day 8, is due to increased production of diverse vascular growth mediators from multiple pathways including hypoxia induced HIF, TGFb, NFkB and other signaling pathways [71, 85, 96, 100, 171-173], incorporated herein by reference, see Indracolla in FIG. 28.

Figure 28:
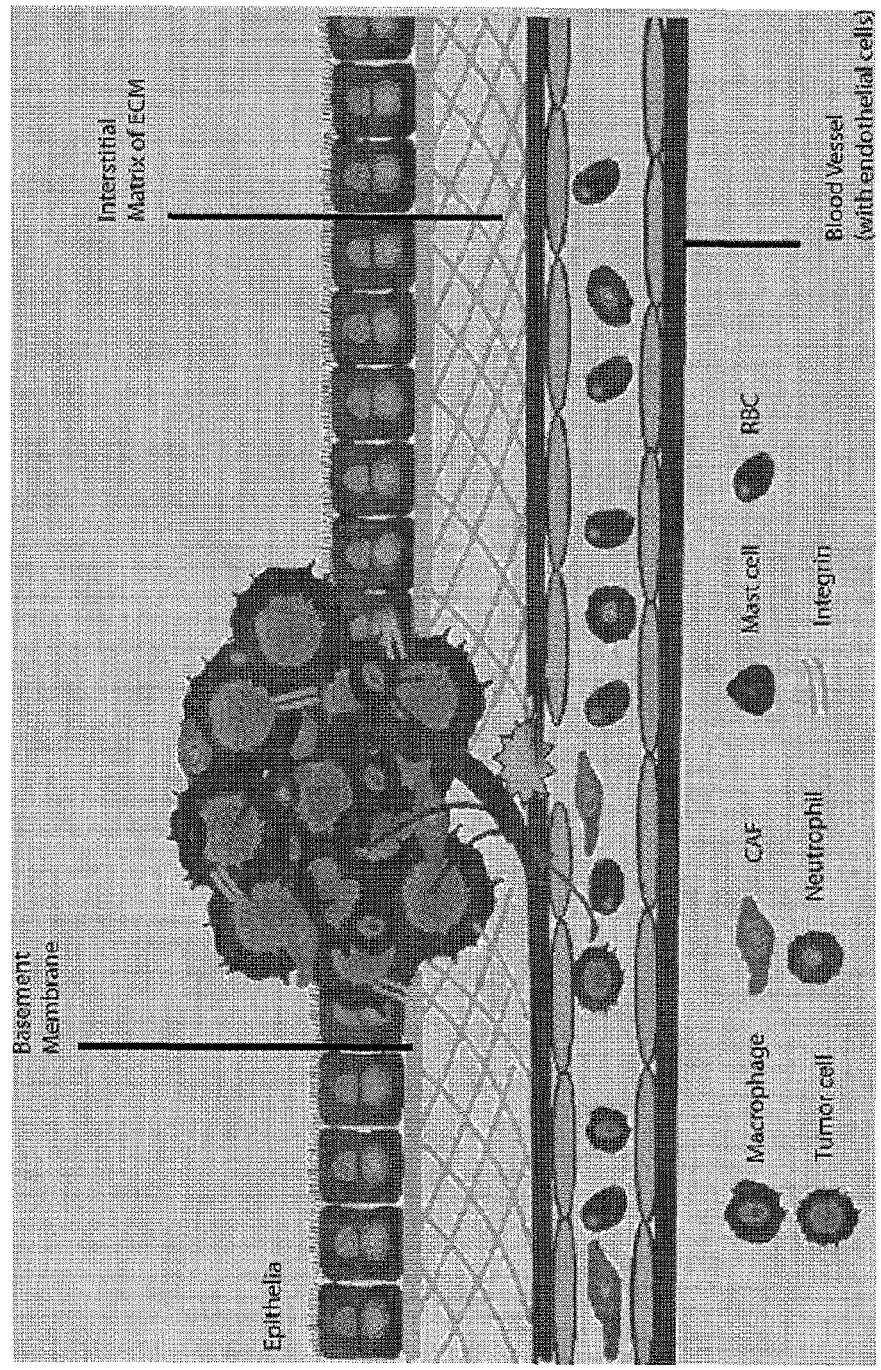
FIG. 28 shows a summary of the microenvironment.

FIG. 28 shows a summary of the microenvironment. The tumor mass environment is composed of heterogeneous mixture of stromal cells (such as fibroblasts, endothelial cells, and immune cells such as macrophages and ECM (extracellular matrix) components). Transformation of the microenvironment occurs with the activation of the metalloproteases which occurs as result of lactate effect on TGF b [68] and on macrophages with the release of IL-23/17 [72], and FGF2. Lactate induced MCT lactate transporters also activate metalloproteases in conjunction with lactate induced hyaluronan/CD147, and caveolin-1 [69] and FGF. IL-17 enhances the vascular growth effects of FGF2 and VEGF. Lactate induces the NFkB inflammatory pathway which increases various cytokines and COX 1 and COX-2 and anti apoptotic pathways [71]. The resulting prostaglandins enhance vasculogenesis. The tumor mass uses these various cell types to secrete cytokines, growth factors such as VEGF and TGF-b (transforming growth factor b), and matrix degrading proteins (MMP's) to create a prometastatic niche that supports the tumor during invasion, angiogenesis, and extravasatin. In addition, integrins and their receptors mediate cellular attachment and communication, from Alphonso and Alahari, Neoplasia, p 1264-71, December 2009 [174], incorporated herein by reference.

With recognition of the importance of transformation of the microenvironment it is relevant to note the role of acidic lactate in inducing the transformation and the effects on the metalloproteases, certain signaling pathways, and different cellular elements.

Angiogenesis Produced by Acidic Lactate Effects on Microenvironment

The merits of the ALPHA concept for angiogenesis are definitely supported by recent data reported by Indracollo et al. in the Proceedings of the National Academy [149]. In their report they noted that there were two distinct phases of angiogenesis, an early and a delayed/maintenance phase. The first phase was supported solely by FGF and VEGF while the later phase was supported by numerous other vascular growth factors, FIG. 29A-29B.

The other diverse vascular growth factors for the delayed/maintenance angiogenesis included COX2, Angiopoietin 1, IL-6, IL-8, IL-15 and others. The total dependence of the first stage on FGF and VEGF and the interaction and synergy of the many factors for the later phase has been emphasized by numerous sources [175-178], all incorporated herein by reference.

Figure 29:
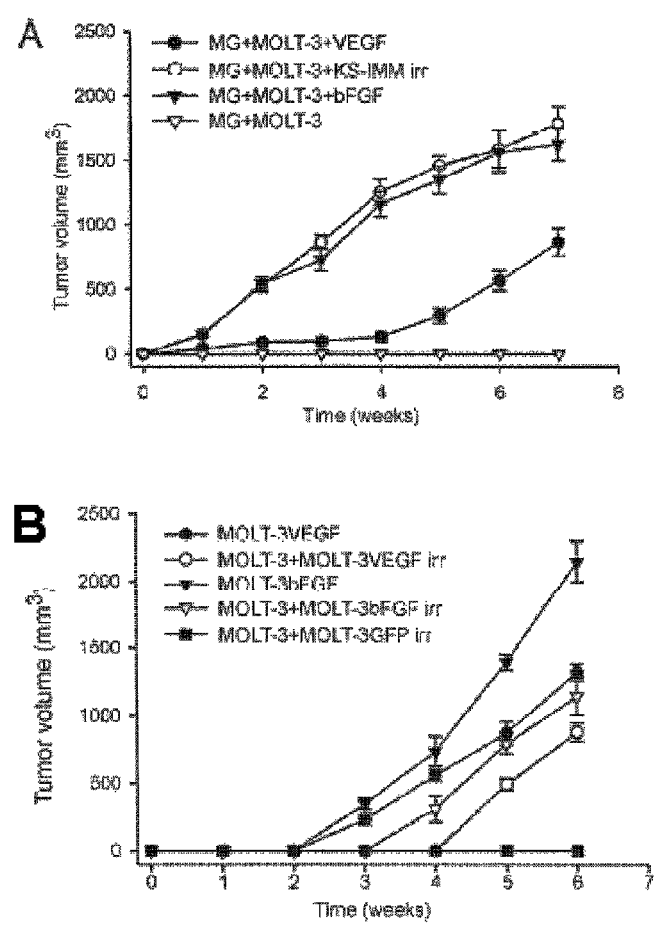
FIG. 29A-29B shows graphs demonstrating the effects of bFGF and VEGF on MOLT-3 tumor growth.

FIG. 29A-29B shows graphs demonstrating the effects of bFGF and VEGF on MOLT-3 tumor growth. FIG. 29A shows MOLT cells with matrigel (MG) and different vascular mediators. MG-MOLT3+bFGF pellets showed early/incipient and delayed/maintenance angiogenesis and growth. MG-MOLT3+KS (Kaposi Sarcoma)—IMMirr shows similar early and delayed growth. Indraccolo et al. state, "The phenomenon depends mainly on the influence of KS cells on the host microenvironment" [149]. Delayed growth of MG-MOLT3+VEGF produced delayed growth and angiogenesis. Without Kaposi cell sarcoma co injection the two phases early/incipient and late/delayed did not occur.

FIG. 29B shows the growth curves of MOLT3 cells which were transfected with retroviral vectors for bFGF and VEGF. MOLT3 cells that were transfected whether irradiated or not were capable of sustaining progressive growth. The delay in onset of growth was due to delay in mediator production. The cells not irradiated (MOLT3-VEGF and MOLT3-bFGF) grew earlier than the irradiated ones (MOLT3-MOLT-3VEGFirr, MOLT3-MOLT-3bFGF in). The MOLT3 GFP labeled with fluorescence did not grow because no growth factors were provided. As an aside it is interesting to note the animals were not submitted to hypoxia so it is likely that the tissues were at least initially normoxic.

Finally the most important conclusion by Indracolla et al. [149] is that the initial angiogenic burst which interrupted dormancy was not due to the tumor cells themselves but their effects on the microenvironment. This was definitively emphasized by direct statements by the sources. Indracolla titled the report, "Interruption of tumor dormancy by a transient angiogenic burst within the tumor microenvironment." Indracolla et al. further stated that the angiogenic "phenomenon observed depends mainly on the effect of the KS (Kaposi Sarcoma) cells on the host microenvironment." They also stated "A transient change in the microenvironment, such as that provided by local inflammation, would suffice for tumor cells with even low angiogenic potential to escape from dormancy and give rise to progressively growing lesions." It is a reasonable conclusion that acidic lactate may be the prime cause of such changes.

Oxygenation Levels: Normoxic State of Incipient Angiogenesis and Hypoxic State of Delayed Angiogenesis In addition to the inferences by Li et al. and others a very sophisticated study by Cao et al. [150] confirmed the different oxygenation levels of the two stages of angiogenesis. Their findings were clearly indicated by the title, "Observation of Incipient Tumor Angiogenesis That Is Independent of Hypoxia and Hypoxia Inducible Factor-1 Activation."

Their experimental design was simple, elegant, and sophisticated using a murine transparent widow model, as follows. They used "genetically engineered HCT116 human colon carcinoma cells and 4T1 mouse mammary carcinoma cells with constitutively expressed red fluorescence protein as a tumor marker and green fluorescence protein (GFP) as a reporter for hypoxia and HIF-1 activation.", see FIG. 30A-30I.

Figure 30:
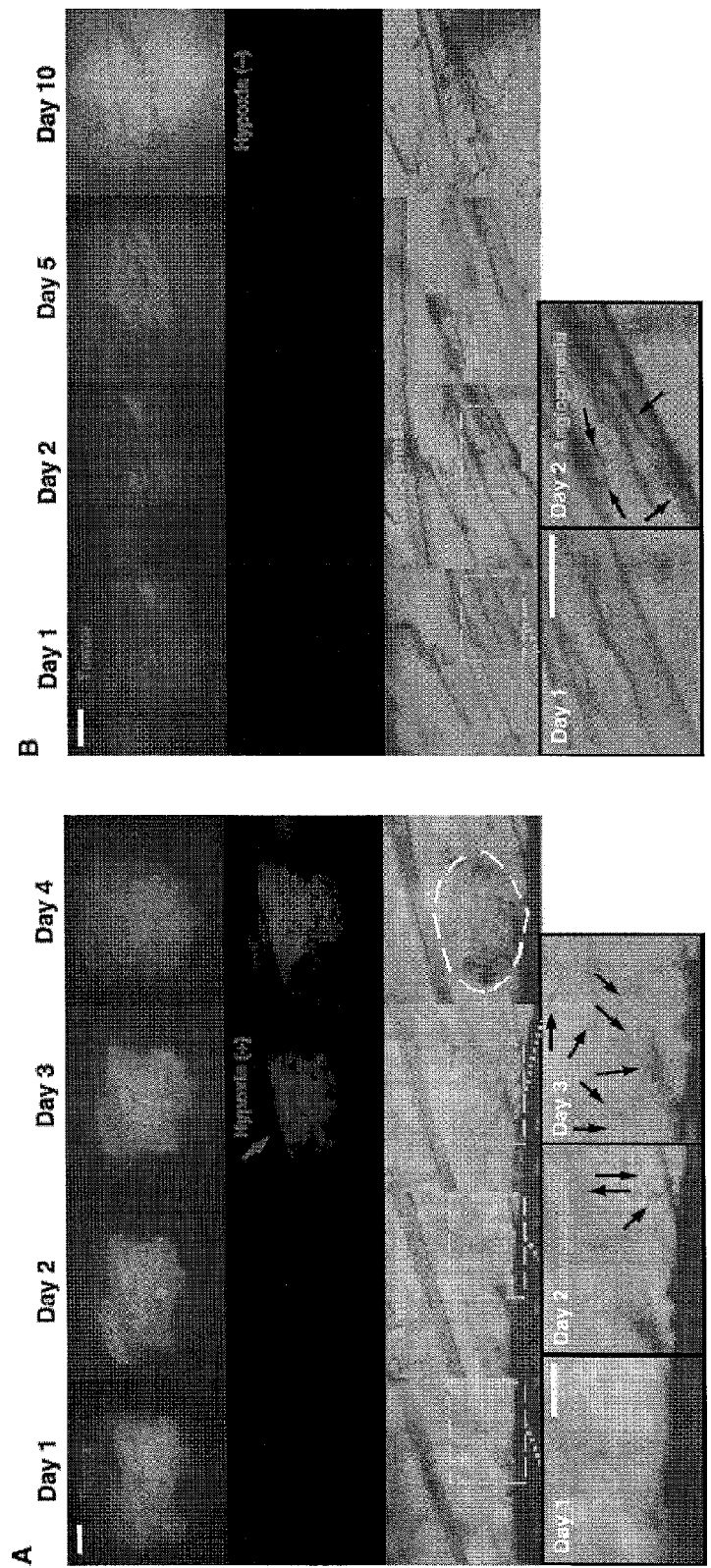
FIG. 30A-30I shows suppression of hypoxic response by selectively killing hypoxic cells does not delay incipient tumor angiogenesis.
Figure 30:
Figure 30:
Figure 30:
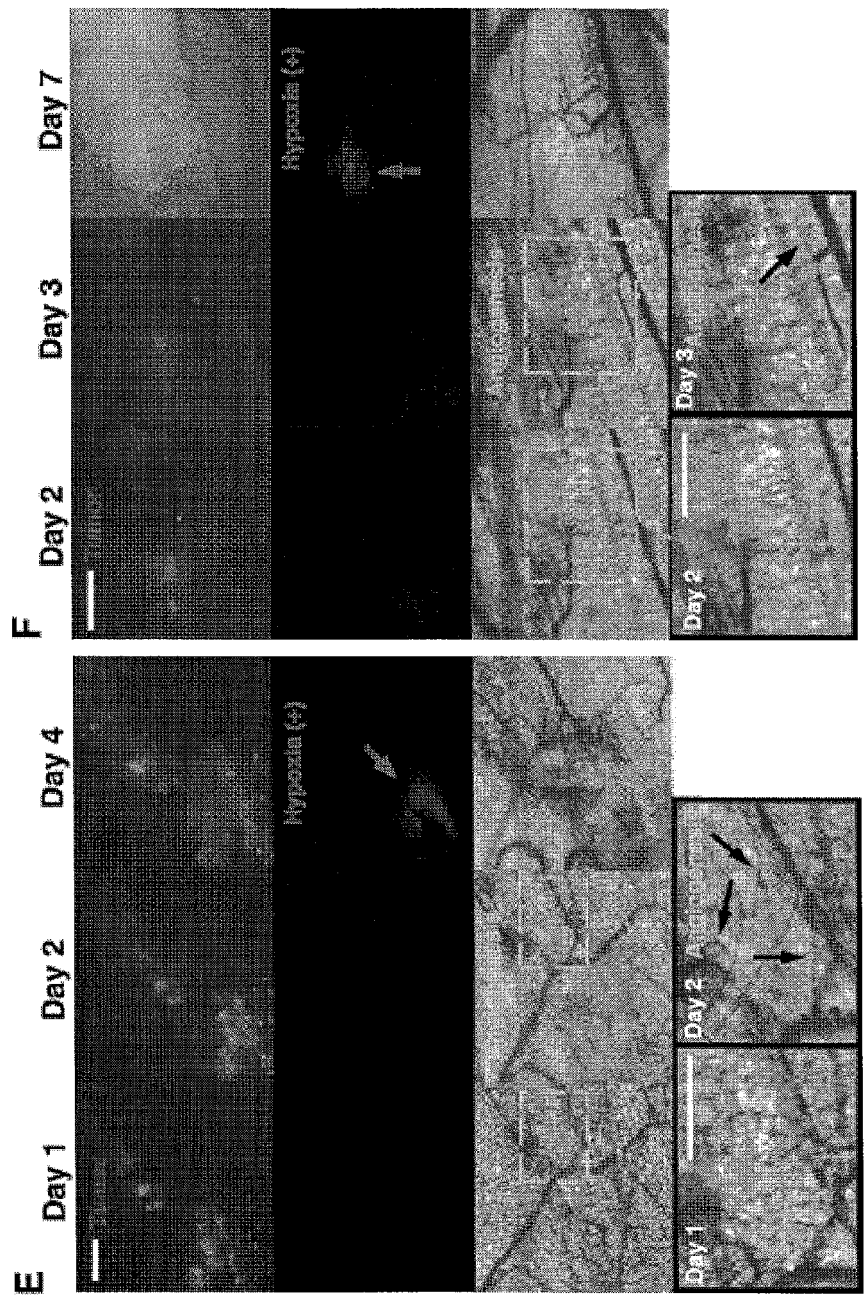
Figure 30:
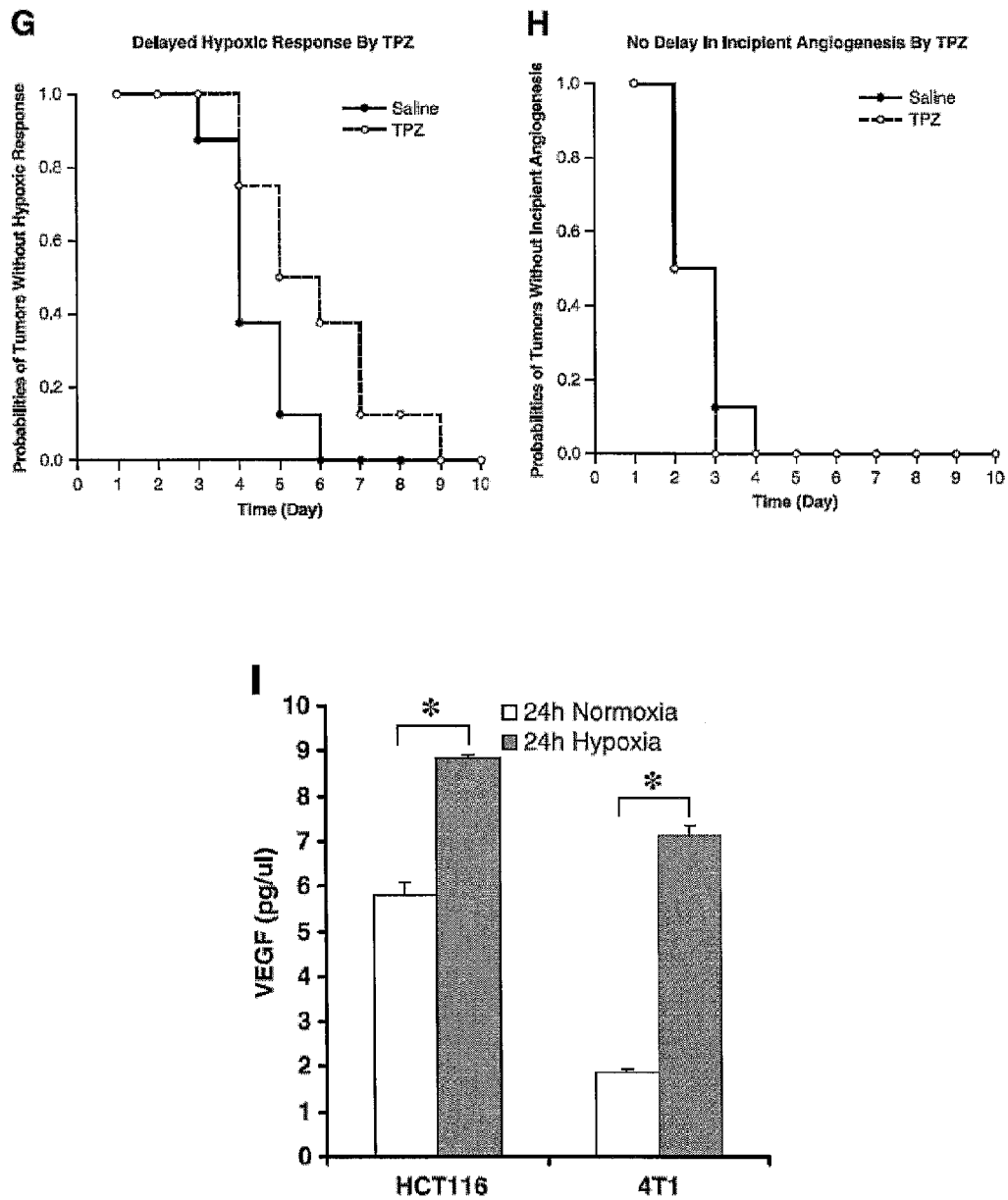

FIG. 30A-30I shows suppression of hypoxic response by selectively killing hypoxic cells does not delay incipient tumor angiogenesis. FIG. 30A shows a representative window chamber images of a saline-treated HCT116 tumor revealing the incipient angiogenesis (Day 2; black arrows) before the hypoxic response (Day 3; green arrow). Endothelial cords and sprouts surrounding the hypoxic region (Day 3; black arrows) developed into a vascular plexus (Day 4; white dashed circle). Bar, 0.3 mm. FIG. 30B shows a representative window chamber images of a tirapazamine-treated HCT116 tumor revealing incipient angiogenesis (Day 2; black arrows) and its development into a vascular plexus (Day 10; white field) in the absence of hypoxic response (no GFP fluorescence). Bar, 0.3 mm. FIG. 30C shows probabilities of time required for the initial hypoxic response in tirapazamine versus saline-treated HCT116 window chamber tumors. Tirapazamine treatment significantly delayed the initial hypoxic response when compared with saline treatment (median time: 9.5 days in the tirapazamine-treated group versus 3.5 days in the saline-treated group; Kaplan-Meier analysis, n=8, log-rank test, P<0.001). FIG. 30D shows probabilities of times required for onset of incipient angiogenesis in tirapazamine versus saline-treated HCT116 window chamber tumors. No significant difference was found between tirapazamine treatment and saline treatment (Kaplan-Meier analysis, n=8, log-rank test, P=0.33). FIG. 30E, representative window chamber images of a saline-treated 4T1 tumor revealing incipient angiogenesis (Day 2; black arrows) before the hypoxic response (Day 4; green arrow). Bar, 0.3 mm. FIG. 30F, representative window chamber images of a tirapazamine-treated 4T1 tumor revealing incipient angiogenesis (Day 3; black arrows) before the hypoxic response (Day 7; green arrow). Bar, 0.3 mm. FIG. 30G, probabilities of the time required for the initial hypoxic response in tirapazamine versus saline-treated 4T1 window chamber tumors. Tirapazamine treatment significantly delayed the initial hypoxic response when compared with saline treatment (median time: 5.5 days in the tirapazamine-treated group versus 4 days in the saline-treated group; Kaplan-Meier analysis, n=8,log-rank P<0.05). FIG. 30H, probabilities of time required for incipient angiogenesis in tirapazamine versus saline-treated 4T1 window chamber tumors. No significant difference was found between tirapazamine and saline treatment (Kaplan-Meier analysis, n=8, log-rank P=0.66). FIG. 30I, VEGF levels in the culture media of HCT116 and 4T1 cells treated with hypoxia versus normoxia. Hypoxia significantly stimulates VEGF secretion (n=6, t test, *P<0.001). Columns, mean; bars, SE. Notably, both cell lines secrete low levels of VEGF under normoxic conditions, from Cao et al., Cancer Research, 2004 [150].

The reference stated, "Mouse dorsal skin-fold window chambers showed that incipient angiogenesis preceded a detectable level of hypoxia. The detectable levels of hypoxia were spatially and temporally related with more intensive secondary angiogenesis following the initial onset of new vessel formation. Selective killing of hypoxic cells by tirapazamine efficiently eliminated or delayed the detection of hypoxic cells, but it did not significantly delay the onset of incipient angiogenesis", FIG. 30A-30I. Other sources [117, 167] have also confirmed angiogenesis may be initiated without hypoxia or HIF. Hendriksen [167] studied glioblastoma implanted tumors in a murine model and noted no hypoxia or HIF1a in small tumors. He stated, "in the tumors of one to four millimeters little or no hypoxia was detectable together with an increasing vascular development."

Summary Observations Supporting ALPHA

A brief, simple summary of their observations and relevance to ALPLHA is as follows. Cell movement and spindle shape of the tumor cells occurred at Day 1-4, which indicated the presence of low pH and lactate in the microenvironment. The presence of acidic lactate indicated transformation of the microenvironment which increases vascular mediators by two distinct pathways, one is release of dormantly stored angiogenic growth factors FGF and VEGF and the second is production of additional growth factors by other pathways (NFkB). Two distinct stages of angiogenesis were observed by Li et al. [164], early incipient at Day 4-6 and a delayed neoangiogenesis at Day 8. The early phase consisted of dilatation and enlargement of co-opted host vessels, Day 6, is known to be caused by the action of VEGF. This early phase was inferred by Li et al. [164] to be normoxic by virtue of the small tumor size and proven to be normoxic by others. In normoxia, release of VEGF from heparan matrix is dependent only upon acidic lactate not the oxygenation level. The delayed neoangiogenesis, which occurred at Day 8, is due to the effects of numerous vascular growth factors, likely by hypoxia and acidic lactate (see below oxygenation section). As noted above reports by Cao and Indracolla support the two critical premises of ALPHA that the early incipient angiogenesis is normoxic and that the vasculogenesis process occurs because of the effects of tumor on the microenvironment.

Analysis Conclusions

In a broad sense, the traditional angiogenesis theory has produced remarkable benefits to healthcare in that it has stimulated extensive research into molecular signaling pathways. However, it has not specifically fulfilled its promise to revolutionize the diagnosis and treatment of cancer, indicating that a new paradigm is needed as are cancer treatments that conform to this new paradigm Major deficiencies and numerous inconsistencies in the application of the traditional theory have become apparent with the premise that hypoxia drives angiogenesis and that arterial growth and oxygenation drives tumor growth. The traditional theory cannot explain why anti-VEGF drugs do not work as a single agent. Current theory does not explain how angiogenesis can occur in normoxic or hyperbaric situations. Normalization of oxygenation in cancer patients does not increase cancer recurrence. Furthermore, successful modern imaging perfusion methods depend upon venous, not arterial, attributes. Review and reinterpretation of the original Gimbrone and Folkman study [4] supports the ALPHA concept. If one considers the abundant data in many fields it can be used to formulate the proposed A3L2PHA concept which provides an alternate perspective on vasculogenesis.

Glycolysis is preferred by cancer because of numerous reasons. First it produces abundant energy but with large amounts of lactate. It is not intended that embodiments of the invention be limited to any particular mechanism; however, it is believed that moderate acidic lactate levels enhance cancerous process but excessive levels causes changes supporting dormancy, i.e. lower metabolism, reduced protein synthesis, reduced mitosis and proliferation, and lack of apoptosis). It is not intended that embodiments of the invention be limited to any particular mechanism; however, it is believed that removal or reduction of lactate (by change of culture medium or increased transport by lymphovenous drainage) restores tumor growth teleologically, The needs of cancer and normal cells are completely different, one depends upon glucose while the other depends upon oxygen and glucose. Teleologically, why would an organism preferring glycolysis not requiring oxygen want to grow arteries? It is more logical that it would require lymphovenous drainage to modulate and optimize the appropriate level of lactate.

It is not intended that embodiments of the invention be limited to any particular mechanism; however, it is believed that low pH and elevated lactate have well defined signaling pathways which induce most of the vascular mediators (FGF, VEGF, ephrin, PDGF, etc). Embryologic models, animal dissection studies and immunopathologic for vascular specification have shown that the mechanistic site of the vascular growth mediators sequentially occur on the lymphatics, veins, and finally arteries.

Modern angiogenesis models correlate well with the extensive basic science data. T It is not intended that embodiments of the invention be limited to any particular mechanism; however, it is believed that the recognized stages of angiogenesis (transformation of the microenvironment, early incipient angiogenesis, delayed maintenance angiogenesis can all be explained by the effects of low pH and elevated lactate. Modern models show that angiogenesis is not a single trigger step, but occurs in two stages or phases, with the first likely being normoxic. It is not intended that embodiments of the invention be limited to any particular mechanism; however, it is believed that the killing of hypoxic cells does not prevent incipient early angiogenesis. These models confirm the initial phase is normoxic and the angiogenic burst, which interrupts tumor dormancy results from tumor effects on the microenvironment. The most recent models show that the initial release of FGF and VEGF required for incipient angiogenesis occurs from transformation of the microenvironment induced by acidic lactate. It is not intended that embodiments of the invention be limited to any particular mechanism; however, it is believed that the later neoangiogenic phase occurs because of hypoxia but also likely from the diverse effects of acidic lactate both locally and as an induction agent for inflammatory pathways and diverse angiogenic growth factors. Correlation of the many models shows that vasculogenesis sequentially develops lymphangiogenesis, phlebogenesis and finally arteriogenesis.

The role of the ALPHA paradigm has yet to be determined but it seems complementary, synergistic and perhaps dominant to the traditional hypoxic vasculogenesis concept Cancer uses both the aerobic and the glycolytic pathways, which have different teleologic needs (aerobic requires oxygen and glycolysis requires efficient waste drainage). Depending upon the oxygen state, normoxia or hypoxia, either the traditional or the ALPHA vasculogenesis paradigm is more important than the traditional paradigm. ALPHA is well founded in the literature a vigorous vetting in the scientific community is warranted. It is not intended that embodiments of the invention be limited to any particular mechanism; however, it is believed that ALPHA paradigm's role is likely complementary to the hypoxic process but perhaps dominant because it operates at all oxygenation levels. It is not intended that embodiments of the invention be limited to any particular mechanism; however, it is believed that ALPHA can initiate and support angiogenesis in normoxia and supplement hypoxic angiogenic effects with increased production of acidic lactate. Effective anti angiogenic treatment will require treatment of both major vasculogenesis pathways.

ALPHA emphasizes the importance of low pH and elevated lactate for the induction of vasculogenesis (lymphatics, veins, and arteries) and the growth and malignant spread of cancer. Interruption or diminution of the acidic lactate by treatment will reduce or eliminate vasculogenesis caused by this waste product and also reduce or eliminate the many advantages of elevated lactate on the cancerous processes discussed herein, i.e. adaptive selective environment, facilitation of cancer cell mutation and proliferation, induction of hyaluronan which enhances cell migration and metastases, induction of NFkB pathways known to upregulate anti-apoptotic pathways, transform macrophages and fibroblasts to tumor forms, impairment of the local immune system, induction of cytokines and COX2 known to induce and support cancer, and others.

The proposed treatment with CAIX,CAXII, and aquaporin blockage will: 1) reduce and block the ALPHA vasculogenesis mechanism 2) reduce intracellular pH in cancer cells causing damage or death 3) the induced lower intracellular pH will block glycolysis (there by reduce extracellular and intracellular lactate) due to end product inhibition as well as inhibit phosphofrutose kinase by the decreased pH which is the dominant regulatory step of glycolysis 4) impair the metabolon of CAIX and MCT1/MCT4 which are codependent and spatially correlated (pearson correlation of Grillon, E. et al. (2011)[179])

New Methods of Treating Hypoxic Cancer

Selvakumaran, M. et al. (2008) [180], incorporated herein by reference, discloses that the addition of the anti-vascular endothelial growth factor (anti-VEGF) monoclonal antibody bevacizumab to a chemotherapy regimen resulted in improved response rates and survival in patients with advanced disease. Selvakumaran, M. et al. determined that bevacizumab treatment is an effective inducer of a hypoxic environment, but the resulting cell death and tumor shrinkage is determined by the susceptibility of the tumor to apoptosis. The induction of apoptosis by hypoxia may contribute to the benefits of such treatment in the clinical setting. In many cases, hypoxia induction does not induce apoptosis, such cases present a significant challenge in the treatment of cancer.

It is not intended that embodiments of the invention be limited to any particular mechanism; however, it is believed that cancers prefer glycolytic metabolism, requiring only glucose and not oxygen, which makes ample ATP energy but also creates large amounts of lactate and low pH. Although it is not necessary to understand the mechanism of an invention, it is believed that depending upon the concentration levels these waste products may provide specific benefits to cancer, cause tumor dormancy, and transform the microenvironment. It is not intended that embodiments of the invention be limited to any particular mechanism; however, it is believed that stabilizing the macroenvironment of hypoxic cancer tissues can significantly contribute to the treatment of said cancer. It is not intended that embodiments of the invention be limited to any particular mechanism; however, it is believed that in as much angiogenesis follows transformation and interrupts tumor dormancy, thus promoting cancer growth, complementation of a treatment to stabilize the microenvironment of cancer with an angiogenesis inhibitors could be an effective treatment for various cancers. It is not intended that embodiments of the invention be limited to any particular mechanism; however, it is believed that new evidence suggests that vascular changes occur sequentially in the lymphatics, veins, and lastly, the arteries (not first, as previously believed).

It is not intended that embodiments of the invention be limited to any particular mechanism; however, it is believed that the use of carbonic anhydrase 9 or carbonic anhydrase 12 inhibitors, such as bumetanide, could be used to destabilize the pH homeostasis of the cancer tissues inducing severe or lethal damage selectively to cancer cells which are rich in CAIX and XII, as compared to normal tissue. Further, with inhibition of CAIX and CAXII, the cancer cell internal pH will decrease increasing acidity. Basic biochemistry of glycolysis indicates the main regulatory enzyme/molecule phosphofructokinses is inhibited by low pH reducing or stopping glycolysis. With reduced or cessation of glycolysis, reduce lactate levels will deprive the cancer of the modulated benefits including anti-apoptosis, selective adaptive environment, "stemcell "properties permitting mutation. Butamide blocking of aquaporin will prevent oncotic equilibration and thereby induce additional hyperosmotic damage. With restoration of the normal cellular microenvironment will enable effective treatment of cancer with other chemotherapeutic agents, including, but not limited to angiogenesis inhibitors. In one embodiment, the invention relates to a method of treating cancer comprising targeted delivery of carbonic anhydrase inhibitor, such as bumetanide, to cancerous tissues, lesions, or tumors. In one embodiment, the invention relates to the delivery of a carbonic anhydrase inhibitor, such as bumetanide, to cancerous tissues in an effective amount necessary to prevent hypoxic conditions or reverse hypoxic conditions. In one embodiment, prevention of hypoxic conditions will effectively treat said cancer. In some embodiments, various thiazide diuretics, such as bumetanide, can be considered carbonic anhydrase inhibitor.

In one embodiment, the invention relates to a method of treating cancer comprising administering to a patient in need of therapy an effective amount of low dose, frequently administered combination of a carbonic anhydrase inhibitor and an angiogenesis inhibitor. In one embodiment an angiogenesis inhibitor includes tumor-vascular disrupting agents described by Siemann (2011) [181], incorporated herein by reference. In one embodiment, said angiogenesis inhibitor is selected from the group consisting of ZD6474, ZD 6126, AZD2171, SU6668 and SU5416, bevacizumab, mv833, anti-FLT-1 ribozyme, SU5416, PTK 787, ZD4190, ZD6474, CEP-7055, SU11248, and mixtures thereof. In one embodiment, said angiogenesis inhibitor is bevacizumab. In one embodiment, said carbonic anhydrase inhibitor is bumetanide. In one embodiment, said carbonic anhydrase inhibitor is a carbonic anhydrase 9 and carbonic anhydrase 12 inhibitor. In one embodiment, the treatment results in one or more of clinical benefit remission, an increased quality of life or prolongation of survival of the patient. In one embodiment, said treatment results in the shrinkage of a tumor or prolonged stability of the cancer. In one embodiment, said treatment reduces metastases of said cancer.

In one embodiment, the invention relates to a pharmaceutical composition comprising an effective amount of a combination of a carbonic anhydrase inhibitor and an angiogenesis inhibitor. In one embodiment, said angiogenesis inhibitor is selected from the group consisting of ZD6474, ZD 6126, AZD2171, SU6668 and SU5416, bevacizumab, mv833, anti-FLT-1 ribozyme, SU5416, PTK 787, ZD4190, ZD6474, CEP-7055, SU11248, and mixtures thereof. In one embodiment, said angiogenesis inhibitor is bevacizumab. In one embodiment, said carbonic anhydrase inhibitor is bumetanide. In one embodiment the invention relates to the composition described above adapted for parenteral administration. In one embodiment the invention relates to the composition described above adapted for intravenous administration.

In one embodiment the invention relates to a method for treating a patient with cancer, wherein said cancer is unresponsive to traditional therapy, said method comprising administering to said patient a combination of a carbonic anhydrase inhibitor and an angiogenesis inhibitor in amounts effective to provide a clinical benefit remission, an increased quality of life or prolongation of survival of the patient. In one embodiment, said cancer is hypoxic cancer. In one embodiment, said treatment results in the shrinkage of a tumor or prolonged stability of the cancer. In one embodiment, said method results in a complete remission of said cancer. In one embodiment an angiogenesis inhibitor includes tumor-vascular disrupting agents described by Siemann (2011) [181], incorporated herein by reference. In one embodiment, said angiogenesis inhibitor is bevacizumab. In one embodiment, said carbonic anhydrase inhibitor is bumetanide.

In one embodiment, the invention relates to the treatment of hypoxic cancer. In one embodiment, treatment of hypoxic cancer includes targeted bloodstream injection of a carbonic anhydrase inhibitor, such as bumetanide. In one embodiment, treatment comprises catheterization of the hepatic artery. In one embodiment, treatment comprises occluding arteries with the treatment of bumetanide. In one embodiment, treatment comprises embilization. In one embodiment, treatment comprises embilization with polymers embedded with carbonic anhydrase inhibitors. In one embodiment, said carbonic anhydrase inhibitors includes a carbonic anhydrase 9 or 12 inhibitor, such as bumetanide. In one embodiment, said polymers embedded with carbonic anhydrase inhibitors slowly release bumetanide. Some non-limiting example of such polymers includes: U.S. Pat. No. 5,384,333 [182], U.S. Pat. No. 5,302,397 [183], and U.S. Pat. No. 5,626,877 [184] (all herein incorporated by reference). In one embodiment, said polymers embedded with carbonic anhydrase inhibitors includes a bumetanide-loaded polymeric implant for the treatment of solid tumors, for example using a system described by Wadee et al. (2011) [185]. In one embodiment, said polymers embedded with carbonic anhydrase inhibitors, such as bumetanide, release bumetanide over a long period of time. In one embodiment, slow delivery of bumetanide is from the extended release formulation. In one embodiment, said polymers embedded with carbonic anhydrase inhibitors are introduced in a single step. In one embodiment, said polymers embedded with carbonic anhydrase inhibitors are introduced several times over the course of treatment. In one embodiment, said treatment bumetanide is given intravenously in combination with artery embilization with polymers embedded with carbonic anhydrase inhibitors.

An important permutation will be a slow release form of bumetanide, in one embodiment, over 8-12 hours. This will be important for continuing oral therapy because IV treatment may be necessary One reference that describes various slow release forms of bumetanide is Hamed, E. A. M. (2002) Application and Evaluation of Extended Release Technology to Loop, Diuretics Doctoral Thesis [186], herein incorporated by reference. Other types of carbonic anhydrase inhibitors are know to be used in slow release form, such as those described in U.S. Pat. No. 5,095,026 [187], herein incorporated by reference. A slow release pill form of bumetanide and as well any other CAIX, CAXII inhibitor on the market are considered forms of carbonic anhydrase therapy. The action of such drugs is quite rapid and therefore one embodiment involves slow release formulas of such carbonic anhydrase inhibitors, such as bumetanide. In one embodiment the invention relates to both acute and long term treatment with a slow release carbonic anhydrase inhibitor to chronically suppress CAIX and CAXII.

In one embodiment, the invention contemplates methods and compositions for the treatment of cancer. In one embodiment, the invention relates to the treatment of hypoxic cancer. In one embodiment, said cancer comprises well defined tumors. In one embodiment, said treatment involves thermal ablation of arteries or other blood vessels supplying blood to well defined tumors in combination with treatment with bumetanide. In one embodiment, said treatment of said cancer with thermal ablation is proceeded with bumetanide treatment. In one embodiment, a catheter is introduced to the hepatic artery for the thermal ablation and delivery of a carbonic anhydrase inhibitor, such as bumetanide, for treatment to occlude arteries of interest supplying blood to said cancer. In one embodiment, thermal ablation includes, but is not limited to radiofrequency thermal ablation (RFA), cryoablation, microwave ablation, laser ablation, and ultrasound ablation. In one embodiment, treatment comprises additional treatment with an angiogenesis inhibitor. In one embodiment an angiogenesis inhibitor includes tumor-vascular disrupting agents described by Siemann (2011) [181], incorporated herein by reference. In one embodiment, said angiogenesis inhibitor is selected from the group consisting of ZD6474, ZD 6126, AZD2171, SU6668 and SU5416, bevacizumab, mv833, anti-FLT-1 ribozyme, SU5416, PTK 787, ZD4190, ZD6474, CEP-7055, SU11248, and mixtures thereof.

In one embodiment, said treatment involves electroporation with a nano knife system of arteries or other blood vessels supplying blood to tumors or the cancer cells themselves in combination with treatment with bumetanide. In one embodiment, said treatment of said cancer with electroporation is preceded with bumetanide treatment.

In one embodiment, the invention relates to a composition for the treatment of cancer in a subject. The composition comprises an angiogenesis inhibitor or pharmaceutically acceptable salt or prodrug thereof and a carbonic anhydrase inhibitor or pharmaceutically acceptable salt or prodrug thereof. In one embodiment, said antiogenesis inhibitor is bevacizumab. In one embodiment, said carbonic anhydrase inhibitor is a carbonic anhydrase 9 or carbonic anhydrase 12 inhibitor. In one embodiment, said carbonic anhydrase inhibitor is bumetanide. In another aspect, the method comprises administering to the subject a angiogenesis inhibitor or pharmaceutically acceptable salt or prodrug thereof and a carbonic anhydrase inhibitor or pharmaceutically acceptable salt or prodrug thereof.

Although the invention has been described with reference to these preferred embodiments, other embodiments can achieve the same results. Variations and modifications of the present invention will be obvious to those skilled in the art and it is intended to cover in the appended claims all such modifications and equivalents. The entire disclosures of all applications, patents, and publications cited above, and of the corresponding application are hereby incorporated by reference.

Thus, specific compositions and methods of targeted treatment of anaerobic cancer have been disclosed. It should be apparent, however, to those skilled in the art that many more modifications besides those already described are possible without departing from the inventive concepts herein. The inventive subject matter, therefore, is not to be restricted except in the spirit of the disclosure. Moreover, in interpreting the disclosure, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates, which may need to be independently confirmed.

Detailed Description of Drugs

VEGF inhibitors or anti-VEGF therapy may involve binding of an agent to VEGF to prevent its modulation of a receptor such as VEGFR-1 (flt-1), VEGFR-2 (flk-1 or KDR), or through inhibition of tyrosine kinase in promoting angiogenesis or it may inhibit the binding of VEGF to one or more of its receptors by any one or more mechanisms. Regardless of the mechanism of action, anti-VEGF activity associated with the use of an effective amount of a VEGF inhibitor in the present invention results in a reduction in VEGF activity (angiogenesis/vascularization) in the tumor, and a response which is inhibitory to cancer growth, elaboration and metastases and which helps to promote cancer remission in combination with the other agents. Bevacizumab is a preferred VEGF inhibitor for use in the present invention. Compounds/compositions according to the present invention which represent anti-VEGF therapy (angiogenesis inhibitors) include for example, ZD6474, ZD 6126, AZD2171 (Astra Zeneca), SU6668 and SU5416 (Sugen), bevacizumab (Avastin), mv833, anti-FLT-1 ribozyme (Angiozyme), and the tyrosine kinase inhibitors SU5416 (Semaxanib), PTK 787 (ZK 222584), ZD4190, ZD6474, CEP-7055, SU11248 and mixtures thereof. In one embodiment anti-angiogenic agents include tumor-vascular disrupting agents described by Siemann (2011) [181], incorporated herein by reference.

Vandetanib (rINN, trade name Caprelsa), also known as ZD6474, is an antagonist of the vascular endothelial growth factor receptor (VEGFR) and the epidermal growth factor receptor (EGFR). It is a tyrosine kinase inhibitor, being developed by AstraZeneca.

ZD6126 is a vascular-targeting agent and a prodrug of N-acetylcolchinol, related to colchicine.

Cediranib (tentative trade name Recentin), also known as AZD2171, is a potent inhibitor of vascular endothelial growth factor (VEGF) receptor tyrosine kinases developed by Astra Zeneca.

SU6668, a multitargeted angiogenesis inhibitor described in Klenke, F. et al. (2007) [188], incorporated herein by reference.

Semaxanib (SU5416) is a tyrosine-kinase inhibitor drug designed by SUGEN as a cancer therapeutic. It is an experimental stage drug, not licensed for use on human patients outside of clinical trials. Semaxanib is a potent and selective synthetic inhibitor of the Flk-1/KDR vascular endothelial growth factor (VEGF) receptor tyrosine kinase. It targets the VEGF pathway, and both in vivo and in vitro studies have demonstrated antiangiogenic potential.

Mv833 is anti-human VEGF monoclonal antibody.

Anti-FLT-1 ribozyme or Angiozyme is a substance that is being studied in the treatment of kidney cancer. It may prevent the growth of blood vessels from surrounding tissue to the tumor. It belongs to the families of drugs called VEGF receptor and angiogenesis inhibitors. Angiozyme is also called RPI.4610.

The tyrosine kinase inhibitors include, but are not limited to: SU5416 (Semaxanib), PTK 787 (Vatalanib), ZD4190, ZD6474 (Vandetanib), CEP-7055, and SU11248 (Sunitinib).

Semaxanib (SU5416) is a tyrosine-kinase inhibitor drug designed by SUGEN as a cancer therapeutic. Semaxanib is a potent and selective synthetic inhibitor of the Flk-1/KDR vascular endothelial growth factor (VEGF) receptor tyrosine kinase. It targets the VEGF pathway, and both in vivo and in vitro studies have demonstrated antiangiogenic potential.

Vatalanib (also known as PTK787 or PTK/ZK) is a small molecule protein kinase inhibitor that inhibits angiogenesis. Vatalanib is being developed by Bayer Schering and Novartis. It inhibits all known VEGF receptors, as well as platelet-derived growth factor receptor-beta and c-kit, but is most selective for VEGFR-2.

Vandetanib (trade name Caprelsa), also known as ZD6474, is an antagonist of the vascular endothelial growth factor receptor (VEGFR) and the epidermal growth factor receptor (EGFR). It is a tyrosine kinase inhibitor, being developed by AstraZeneca.

Sunitinib (marketed as Sutent by Pfizer, and previously known as SU11248) is an oral, small-molecule, multi-targeted receptor tyrosine kinase (RTK) inhibitor.

Bevacizumab (Avastin®) (rhuMAb-VEGF) (Anti-VEGF monoclonal antibody) is a recombinant human/murine chimeric monoclonal antibody directed against vascular endothelial growth factor (VEGF).). It is prepared by engineering VEGF-binding residues of a murine anti-VEGF monoclonal antibody into framework regions of human immunoglobulin-1 (IgG1) (Prod Info Avastin, 2004). Only 7% of the amino acid sequence is derived from the murine antibody, with 93% from IgG1, Figg, W. D. et al. (2002) [189] incorporated herein by reference.

Human VEGF mediates neoangiogenesis in normal and malignant vasculature; it is overexpressed in most malignancies and high levels have correlated with a greater risk of metastases and poor prognosis in many. When VEGF interacts with its receptor in in vitro models of angiogenesis, endothelial cell proliferation and new blood vessel formation occur. In animal models, VEGF has been demonstrated to induce vascular endothelial-cell proliferation/migration, sustain survival of newly-formed blood vessels, and enhance vascular permeability. Bevacizumab binds and neutralizes all human VEGF forms via recognition of binding sites for the two human VEGF receptor types (flt-1 and flk-1). In animal models, the antibody has been shown to stabilize established tumors or suppress tumor growth by inhibiting angiogenesis induced by VEGF, Gordon, M. S. et al. (2001) [190] incorporated herein by reference.

Toxicology of Bevacizumab: Minor bleeding or hemorrhage (eg, epistaxis, and hemoptysis), and thromboembolic events (eg, deep vein thrombosis) have accompanied administration of bevacizumab in some cancer patients. Other serious but uncommon events included; gastrointestinal hemorrhage, subarachnoid hemorrhage, fatal pulmonary hemorrhage, and hemorrhagic stroke (Prod Info Avastin™, 2004). Grade ¾ hypertension (12%), deep venous thrombosis (9%), and intra-abdominal thrombosis (3%) occurred in patients receiving bolus irinotecan/5-fluorouracil/leucovorin plus bevacizumab in a trial of patients with untreated metastatic colorectal cancer. Myocardial infarction and hypotension have also been reported. Modest increases in diastolic and systolic blood pressures and clinical hypertension have been reported frequently during bevacizumab therapy (23% to 34% of patients) and may need to be controlled with antihypertensive medications. Mild asthenia and headache have been common during therapy (up to 70% and 50% of patients, respectively), but may be dose-dependent. Dizziness (22%), hypokalemia (14%) and bilirubinemia (4%) vomiting (50%), anorexia (40%), constipation (30%), stomatitis (30%), dyspepsia (20%), weight loss (15%), taste disorder (16%) and flatulence (16%), myalgia (10%), skin ulcer (6%) and confusion (3%) may occur. Grade ¾ diarrhea (30%) and abdominal pain (6%) were also reported. Nausea and vomiting may be more severe with higher doses. Gastrointestinal perforation occurred in 2% of patients receiving bolus irinotecan/5-fluorouracil/leucovorin plus bevacizumab versus 4% of patients receiving 5-fluorouracil/leucovorin plus bevacizumab in a trial of patients with untreated metastatic colorectal cancer, a typical presentation included abdominal pain, constipation, and vomiting, Hurwitz, H. (2003)[191], incorporated herein by reference.

Proteinuria of varying severity or nephrotic syndrome has been described during therapy with bevacizumab, Cobleigh, M. A. et al. (2003) [192] incorporated herein by reference. Life threatening or fatal pulmonary hemorrhage occurred in 3 to 1% of patients with squamous cell non-small cell lung cancer (4% nonsquamous cell histology) receiving bevacizumab in combination with chemotherapy compared to 0% in the chemotherapy alone group; these events presented suddenly as major hemoptysis and occurred in patients with cavitation and/or necrosis of the tumor, either preexisting or developing during therapy, Chen, et al. (2001) [193] incorporated herein by reference. Skin rash (type unspecified) has been described in some patients following infusion. Low-grade fever and infection have occurred with variable frequency during therapy. The incidence of immunogenicity with bevacizumab exists, but has not been determined (prod info Avastin™, 2004). No antibodies to bevacizumab were reported in a phase I study (n=25) where patients received four doses of 0.1 to 10 mg/kg over 42 days, and assays were performed for up to 70 days, Gordon, M. S. et al. (2001) [190] incorporated herein by reference. There is insufficient clinical experience with bevacizumab to confirm its safety in pregnancy.

Black Box Warnings for Bevacizumab: Gastrointestinal Perforations/Wound Healing Complications: Avastin administration can result in the development of gastrointestinal perforation and wound dehiscence, in some instances resulting in fatality. Gastrointestinal perforation, sometimes associated with intra-abdominal abscess, occurred throughout treatment with Avastin (ie, was not correlated to duration of exposure). The incidence of gastrointestinal perforation in patients receiving bolus-IFL with Avastin was 2%. The typical presentation was reported as abdominal pain associated with symptoms such as constipation and vomiting. Gastrointestinal perforation should be included in the differential diagnosis of patients presenting with abdominal pain on Avastin. Avastintherapy should be permanently discontinued in patients with gastrointestinal perforation or wound dehiscence requiring medical intervention. The appropriate interval between termination of Avastin and subsequent elective surgery required to avoid the risks of impaired wound healing/wound dehiscence has not been determined.

Hemorrhage: Serious, and in some cases fatal, hemoptysis has occurred in patients with non-small cell lung cancer treated with chemotherapy and Avastin. In a small study, the incidence of serious or fatal hemoptysis was 31% in patients with squamous histology and 4% in patients with adenocarcinoma receiving Avastin as compared to no cases in patients treated with chemotherapy alone. Patients with recent hemoptysis should not receive Avastin.

Pharmacology of Bevacizumab: The pharmacokinetics of bevacizumab are linear after doses of 0.3 mg/kg or greater. Following 90-minute intravenous infusions of 0.3, 1, 3, and 10 mg/kg in advanced cancer patients (n=25), peak serum concentrations of bevacizumab ranged from 5 to 9 mcg/mL, 21 to 39 mcg/mL, 52 to 92 mcg/mL, and 186 to 294 mcg/mL, respectively; slight accumulation was observed with repeat doses (weekly), but this was not significant and pharmacokinetics remained linear. Steady-state levels of bevacizumab were obtained in 100 days in 491 patients who received 1 to 20 mg/kg weekly, every 2 weeks, or every 3 week Following 90-minute intravenous infusions of 0.3, 1, 3, and 10 mg/kg in advanced cancer patients (n=25), $AUC_{inf}$ values ranged from 31 to 87, 240 to 382, 550 to 1720, and 2480 to 6010 mcg/mL×day, respectively, Gordon, M. S. et al. (2001) [190] incorporated herein by reference. Central volume of distribution of bevacizumab was greater in males than in females (3.25 L vs. 2.66 L) in 491 patients who received 1 to 20 mg/kg weekly, every 2 weeks, or every 3 week. The clearance of bevacizumab was higher (0.262 L/day vs. 0.207 L/day) in males than females; patients with a higher tumor burden (at or above median value of tumor surface area) also had a higher clearance (0.249 L/day vs. 0.199 L/day). The estimated elimination half-life of bevacizumab was 20 days (range 11 to 50 days) in a pharmacokinetic population analysis of 491 patients receiving 1 to 20 mg/kg weekly, every 2 weeks, or every 3 weeks.

VEGF Serum Level Changes: In advanced cancer patients, free VEGF serum levels were reduced significantly following the first dose of bevacizumab 1 to 10 mg/kg, and remained below the limit of detection for the duration of the study (repeat doses at 28, 35, and 42 days). Levels of total VEGF increased with all doses (0.1 to 10 mg/kg), presumably as a result of increased VEGF synthesis/distribution or reduced VEGF clearance secondary to complex formation (between VEGF and bevacizumab), Gordon, M. S. et al. (2001) [190] herein incorporated by reference.

Storage And Stability: Store bevacizumab vials protected from light, under refrigeration at 2 to 8 degrees Celsius/36 to 46 degrees Fahrenheit. Do not freeze or shake. This product contains no preservative (Prod Info Avastin™, 2004).

Diluted solutions of bevacizumab in 100 mL 0.9% Sodium chloride Injection may be stored for up to 8 hours under refrigeration (2 to 8 degrees Celcius/36 to 46 degrees Fahrenheit) (Prod Info Avastin™, 2004). Early phase I trials were conducted with bevacizumab diluted in 5% Dextrose for Injection. However, results indicate that dextrose inactivates bevacizumab.

Dosage and Administration: The recommended dose of bevacizumab is 5 milligrams/kilogram infused intravenously over 30 minutes every 2 weeks until disease progression diminishes. Bevacizumab should follow chemotherapy. Efficacy of single-agent bevacizumab has not been established. The calculated dose of bevacizumab in 100 milliliters of 0.9% Sodium Chloride Injection should initially be infused over 90 minutes; subsequent doses can be administered in shorter periods of time (60 minutes for the second infusion and 30 minutes for the third infusion, if well-tolerated). Do not administer as an intravenous bolus or push (Prod Info Avastin™, 2004).

The term "effective" or "effective amount" means an amount of a compound which is used to effect an intended result. In the present application, the favorable treatment of cancer is the intended effect, manifest in a remission or shrinkage of the cancer/tumor and/or the prevention or a reduction in or the likelihood of the spread (metastases) of the cancer and a substantial increase in the time of survival. The present method will result in an increase in survival of a patient diagnosed with cancer to at least about 1.5 times, at least about 2 times, at least about 2.5 times, at least about 3 times, at least about 3.5 times, at least about 4 times, at least about 5 times, at least about 6 times, at least about 7 times, at least about 8 times, at least about 9 times and at least about 10 times or more the length of time of survival of the untreated patient determined from the time the cancer is diagnosed in the patient. Optimally, the present invention will result in the improvement of the well being of the patient, a shrinkage of the tumor, a prolongation of survival, the remission of cancer and the prevention (as a manifestation of a reduced likelihood or prevention) of metastases of the cancer to other areas of the patient's body. In general, effective amounts of each of the compounds used in the combined therapy according to the present invention include:

Bumetanide—between about 100 mg and 2.5 grams, preferably about 500 mg to about 2000 mg, preferably about 800 mg, about 1000 mg or about 1500 mg/mm². A slow release form of bumetanide is preferably used such that release of the drug would be evenly released over 8 to 12 hours. In another embodiment, the bumetanide is incorporated into polymers for much longer term release.

Bevacizumab (which may be coadministered with bumetanide, or within a week before or after chemotherapy), is administered intravenously, at about 1 mg/kg to about 15 mg/kg, preferably about 5 mg/kg.

The above combination is preferably administered once about every one-two weeks (preferably about every two weeks twice with each course-one course equals 2 dosages—(preferably a total of 6 courses) preferably being administered over a 4-8 week period (preferably over 4 weeks), although the regimen may be administered more frequently depending upon the disease state. Of course, further courses of the combination therapy may be given, as the disease state merits. The dosage of each of the components may be modified to reflect the size and weight of the patient, as well as the severity of the disease state to be treated.

In some aspects of the present invention, the combined therapy described above is administered once every two weeks for a total of 12 dosages. The components are preferably co-administered, although it is sometimes desirable to administer the bevacizumab (anti-VEGF therapy) within one week of the chermotheraputic compounds or compositions and/or a carbonic anhydrase inhibitor, such as bumetanide.

In additional aspects of the present invention, the premedications dexamethasone, at about 5-10 (preferably 8 mg) mg every 12 hours for six doses (three days) and/or zofran (5-10 mg, preferably 8 mg IV) are administered in effective amounts prior to chemotherapy and then intermittently during further therapy pursuant to physician discretion. The dosage schedules according the present invention are referred to herein as low dose, frequent administration.

Formulations

A "pharmaceutically acceptable monosaccharide" is a pharmaceutically acceptable aldose sugar, a pharmaceutically acceptable ketose sugar, or other specified sugar. Among the pharmaceutically acceptable aldose sugars within the contemplation of the present invention are erythrose, threose, ribose, arabinose, xylose, lyxose, allose, altrose, glucose, mannose, gulose, idose, galactose and talose. Among the pharmaceutically acceptable ketose sugars preferred for use in the composition of the present invention are erythrulose, ribulose, xylulose, psicose, fructose, sorbose, tagatose, and sedoheptulose. Among the other specified sugars preferred for use in the composition of the present invention are fucose, fuculose, rhamnose, or any other deoxy sugar. Although either (D) or (L) isomers may be employed, the (D) form is generally preferable.

The pharmaceutical compositions of the present invention may be prepared by formulating them in dosage forms which are suitable for peroral, rectal or nonparenteral administration, the last-mentioned including intravenous injection and administration into the cerebrospinal fluid. For this purpose, common carriers and routine formulation techniques may be employed.

"API" or "active pharmaceutical ingredient" means the substance in a pharmaceutical drug that is biologically active.

"Common carriers" means those which are employed in standard pharmaceutical preparations and includes excipients, binders and disintegrators the choice of which depends on the specific dosage form used. Typical examples of the excipient are starch, lactose, sucrose, glucose, mannitol and cellulose; illustrative binders are polyvinylpyrrolidone, starch, sucrose, hydroxypropyl cellulose and gum arabic; illustrative disintegrators include starch, agar, gelatin powder, cellulose, and CMC. Any other common excipients, binders and disintegrators may also be employed.

In addition, of the carriers described above, the pharmaceutical composition of the present invention preferably contains antioxidants for the purpose of stabilizing the effective ingredient. Appropriate antioxidants may be selected from among those which are commonly incorporated in pharmaceuticals and include ascorbic acid, N-acetylcysteine, acetylcysteine, L-cystein, D, L-α-tocopherol, and natural tocopherol.

Formulations of the pharmaceutical composition of the present invention which are suitable for peroral administration may be provided in the form of tablets, capsules, powders, granules, or suspensions in non-aqueous solutions such as syrups, emulsions or drafts, each containing one or more of the active compounds in predetermined amounts.

The granule may be provided by first preparing an intimate mixture of one or more of the active ingredients with one or more of the auxiliary components shown above, then granulating the mixture, and classifying the granules by screening through a sieve.

The tablet may be prepared by compressing or otherwise forming one or more of the active ingredients, optionally with one or more auxiliary components.

The capsule may be prepared by first making a powder or granules as an intimate mixture of one or more of the active ingredients with one or more auxiliary components, then charging the mixture into an appropriate capsule on a packing machine, etc.

The pharmaceutical composition of the present invention may be formulated as a suppository (for rectal administration) with the aid of a common carrier such a cocoa butter. The pharmaceutical composition of the present invention may also be formulated in a dosage form suitable for non-parenteral administration by packaging one or more active ingredients as dry solids in a sterile nitrogen-purged container. The resulting dry formulation may be administered to patients non-parenterally after being dispersed or dissolved in a given amount of aseptic water.

The dosage forms are preferably prepared from a mixture of the active ingredients, routine auxiliary components and one or more of the antioxidants listed above. If desired, the formulations may further contain one or more auxiliary components selected from among excipients, buffers, flavoring agents, binders, surfactants, thickening agents, and lubricants.

The dose of the various pro-drugs will of course vary with the route of administration, the severity of the disease to be treated, and the patient to be treated, but the exact dose ultimately chosen should be left to the good discretion of the doctor responsible for the treatment. If a desired dose is determined, the active ingredient may be administered once a day or, alternatively, it may be administered in up to as many portions as deemed appropriate at suitable intervals. The active ingredient may be straightforwardly administered without being mixed with any other components. However, for several reasons, typically for the purpose of providing ease in controlling the dose level, the active compound is preferably administered in a pharmaceutical dosage form.

Experimental

Initial laboratory studies will be performed to determine if inhibiting or impairing the cancerous waste enzymes (CAIX,CAXII) can improve two types of treatment for cancer, arterial closure by embolization and Nanoknife (cancer electroporation).

1. Glioblastoma rat model consisting of tumor implants in rat brain. Protocol will likely include four groups: 1. control, 2. GBM Rx'd with anti-VEGF, 3. GBM Rx'd with anti-VEGF and Bumex, 4. GBM Rx'd with anti-VEGF, Bumex and monocarboxylic transport inhibitor, such as pleuronic polymer 85 (other MCT)
2. Hepatoma rat model: implanted rat tumor in liver will be Rx'd with 4 groups: 1. control, 2. occlusion of arterial flow, 3. occlusion of arterial flow and Bumex, 4. anti-VEGF and Bumex (anti-VEGF to include Avastin and other agents with multiple targets, i.e. Sorafenib)

REFERENCES

1. Stahl, P. H. and Wermuth, C. G., (Eds.) (2002) *Handbook of Pharmaceutical Salts: Properties Selection and Use*, Verlag Helvetica Chimica Acta/Wiley-VCH, Zurich.
2. Elger, G. A. et al. "Controlled release pharmaceutical composition," U.S. Pat. No. 4,828,836 application Ser. No. 07/052,580, filed May 19, 1987. (Published May 9, 1989).
3. Van Lengerich, B. H. "Embedding and encapsulation of controlled release particles," U.S. Pat. No. 6,190,591 application Ser. No. 09/269,763, filed May 17, 1999. (Published Feb. 20, 2001).
4. Gimbrone, M. A. et al. (1972) Tumor Dormancy in Vivo by Prevention of Neovascularization, *The Journal of Experimental Medicine* 136(2), 261-276.
5. Folkman, J. (1990) What Is the Evidence That Tumors Are Angiogenesis Dependent?, *J. Natl. Cancer Inst.* 82(1), 4-7.
6. Sheikh, A. Y. et al. (2000) Effect of hyperoxia on vascular endothelial growth factor levels in a wound model, *Arch. Surg.* 135(11), 1293-1297.
7. Stein, R. (2011) FDA revokes Avastin's approval for breast cancer treatment, Washington Post, Washington, D.C. (Nov. 18, 2011).
8. Jain, R. K. et al. (2006) Lessons from phase III clinical trials on anti-VEGF therapy for cancer, *Nature Clinical Practice Oncology* 3(1), 24-40.
9. Vaupel, P. (2004) The Role of Hypoxia-Induced Factors in Tumor Progression, *The Oncologist* 9(suppl 5), 10-17.
10. Keunen, O. et al. (2011) Anti-VEGF treatment reduces blood supply and increases tumor cell invasion in glioblastoma, *Proc. Natl. Acad. Sci. U.S.A.* 108(9), 3749-3754.
11. Nalluri, S. R. et al. (2008) Risk of Venous Thromboembolism With the Angiogenesis Inhibitor Bevacizumab in Cancer Patients, *JAMA: The Journal of the American Medical Association* 300(19), 2277-2285.
12. Winkler, F. et al. (2004) Kinetics of vascular normalization by VEGFR2 blockade governs brain tumor response to radiation: Role of oxygenation, angiopoietin-1, and matrix metalloproteinases, *Cancer Cell* 6(6), 553-563.
13. Tong, R. T. et al. (2004) Vascular Normalization by Vascular Endothelial Growth Factor Receptor 2 Blockade Induces a Pressure Gradient Across the Vasculature and Improves Drug Penetration in Tumors, *Cancer Res.* 64(11), 3731-3736.
14. Jain, R. K., Tong, R. T., and Munn, L. L. (2007) Effect of Vascular Normalization by Antiangiogenic Therapy on Interstitial Hypertension, Peritumor Edema, and Lymphatic Metastasis: Insights from a Mathematical Model, *Cancer Res.* 67(6), 2729-2735.
15. Jain, R. K. (2001) Normalizing tumor vasculature with anti-angiogenic therapy: Anew paradigm for combination therapy, *Nat. Med.* 7(9), 987-989.
16. Workman, P. et al. (2006) Minimally invasive pharmacokinetic and pharmacodynamic technologies in hypothesis-testing clinical trials of innovative therapies, *J. Natl. Cancer Inst.* 98(9), 580-598.
17. Miller, J. et al. (2005) Imaging angiogenesis: applications and potential for drug development, *J. Natl. Cancer Inst.* 97(3), 172-187.
18. Hu, L. S. et al. (2009) Relative Cerebral Blood Volume Values to Differentiate High-Grade Glioma Recurrence from Posttreatment Radiation Effect: Direct Correlation between Image-Guided Tissue Histopathology and Localized Dynamic Susceptibility-Weighted Contrast-Enhanced Perfusion MR Imaging Measurements, *American Journal of Neuroradiology* 30(3), 552-558.
19. Duong, T. Q. and Kim, S. G. (2000) In vivo MR measurements of regional arterial and venous blood volume fractions in intact rat brain, *Magn. Reson. Med* 43(3), 393-402.
20. Dvorak, H. et al. (2009) Distribution of Vascular Permeability Factor (Vascular Endothelial Growth Factor) in Tumors: Concentration in Tumor Blood Vessels, *The Journal of Experimental Medicine* 174, 1275-1278.
21. Dvorak, H. et al. (1988) Identification and characterization of the blood vessels of solid tumors that are leaky to circulating macromolecules, *Am. J. Pathol.* 133, 95-109.
22. Nagy, J. A. et al. (2006) Permeability properties of tumor surrogate blood vessels induced by VEGF-A, *Lab. Invest.* 86(8), 767-780.
23. Nagy, J. A. et al. (2002) Vascular Permeability Factor/Vascular Endothelial Growth Factor Induces Lymphangiogenesis as well as Angiogenesis, *The Journal of Experimental Medicine* 196(11), 1497-1506.
24. Kohn, S. et al. (1992) Pathways of macromolecular tracer transport across venules and small veins. Structural basis for the hyperpermeability of tumor blood vessels, *Lab. Invest.* 67(5), 596-607.
25. Kuhl, C. K. et al. (1999) Dynamic Breast MR Imaging: Are Signal Intensity Time Course Data Useful for Differential Diagnosis of Enhancing Lesions?, *Radiology* 211(1), 101-110.
26. Kuhl, C. (2007) The Current Status of Breast MR Imaging Part I. Choice of Technique, Image Interpretation, Diagnostic Accuracy, and Transfer to Clinical Practice1, *Radiology* 244(2), 356-378.
27. Kuhl, C. K. (2007) Current Status of Breast MR Imaging Part 2. Clinical Applications1, *Radiology* 244(3), 672-691.
28. Bisdas, S. et al. (2007) Differentiation of benign and malignant parotid tumors using deconvolution-based perfusion CT imaging: Feasibility of the method and initial results, *Eur. J. Radiol.* 64(2), 258-265.
29. Caseiras, G. B. et al. (2008) Inclusion or Exclusion of Intratumoral Vessels in Relative Cerebral Blood Volume Characterization in Low-Grade Gliomas: Does It Make a Difference?, *American Journal of Neuroradiology* 29(6), 1140-1141.
30. Jain, R. et al. (2008) Quantitative estimation of permeability surface-area product in astroglial brain tumors using perfusion CT and correlation with histopathologic grade, *AJNR, American journal of neuroradiology* 29(4), 694-700.
31. Provenzale, J. M. et al, (2006) Correlation of Relative Permeability and Relative Cerebral Blood Volume in High-Grade Cerebral Neoplasms, *Am. J. Roentgenol.* 187 (4), 1036-1042.
32. Spampinato, M. V. et al. (2007) Cerebral blood volume measurements and proton MR spectroscopy in grading of oligodendroglial tumors, *AJR, American journal of roentgenology* 188(1), 204-212.
33. Hu, L. S. et al. (2009) Relative cerebral blood volume values to differentiate high-grade glioma recurrence from posttreatment radiation effect: direct correlation between image-guided tissue histopathology and localized dynamic susceptibility-weighted contrast-enhanced perfusion MR imaging measurements, *AJNR, American journal of neuroradiology* 30(3), 552-558.
34. Weidner, N. et al. (1991) Tumor Angiogenesis and Metastasis—Correlation in Invasive Breast Carcinoma, *N. Engl. J. Med.* 324(1), 1-8.
35. Buckley, D. et al. (2005) Microvessel density in invasive breast cancer assessed by dynamic gd-dtpa enhanced MRI, *J. Magn. Reson. Imaging* 7(3), 461-464.
36. Buadu, L. D. et al. (1996) Breast lesions: correlation of contrast medium enhancement patterns on MR images with histopathologic findings and tumor angiogenesis, *Radiology* 200(3), 639-649.
37. Kriege, M. et al. (2004) Efficacy of MRI and Mammography for Breast-Cancer Screening in Women with a Familial or Genetic Predisposition, *N. Engl. J. Med.* 351(5), 427-437.
38. El Khoury, C. et al (2005) MR Quantification of the Washout Changes in Breast Tumors Under Preoperative Chemotherapy: Feasibility and Preliminary Results, *Am. J. Roentgenol.* 184(5), 1499-1504.
39. Radjenovic, A. et al. (2008) Measurement of pharmacokinetic parameters in histologically graded invasive breast tumours using dynamic contrast-enhanced MRI, *Br. J. Radiol.* 81(962), 120-128.
40. Raatschen, H.-J. et al. (2008) Vascular Permeability during Antiangiogenesis Treatment: MR Imaging Assay Results as Biomarker for Subsequent Tumor Growth in Rats1, *Radiology* 247(2), 391-399.
41. Pham, C. et al. (1998) Magnetic resonance imaging detects suppression of tumor vascular permeability after administration of antibody to vascular endothelial growth factor, *Cancer Investig.* 16(4), 225-230.
42. Thukral, A. et al. (2007) Inflammatory Breast Cancer. Dynamic Contrast-enhanced MR in Patients Receiving Bevacizumab—Initial Experience1, *Radiology* 244(3), 727-735.
43. Boucher, Y., Lee, I., and Jain, R. K. (1995) Lack of General Correlation between Interstitial Fluid Pressure and Oxygen Partial Pressure in Solid Tumors, *Microvasc. Res.* 50(2), 175-182.
44. Boucher, Y. and Jain, I. K. (1992) Microvascular Pressure Is the Principal Driving Force for Interstitial Hypertension in Solid Tumors: Implications for Vascular Collapse, *Cancer Res.* 52(18), 5110-5114.

45. Engelbrecht, M. R. et al. (2003) Discrimination of Prostate Cancer from Normal Peripheral Zone and Central Gland Tissue by Using Dynamic Contrast-enhanced MR Imaging *Radiology* 229(1), 248-254.

46. Kim, J. K. et al. (2005) Wash-in rate on the basis of dynamic contrast-enhanced MRI: Usefulness for prostate cancer detection and localization, *J. Magn. Reson. Imaging* 22(5) 639-646.

47. Jackson, a. S. N. et al. (2009) Dynamic contrast-enhanced MRI for prostate cancer localization, *Br. J. Radiol.* 82(974), 148-156.

48. Franiel, T. et al. (2010) Differentiation of Prostate Cancer From Normal Prostate Tissue: Role of Hotspots in Pharmacokinetic MRI and Histologic Evaluation, *Am. J. Roentgenol.* 194(3), 675-681.

49. Ito, H. et al. (2003) Visualization of prostate cancer using dynamic contrast-enhanced MRI: comparison with transrectal power Doppler ultrasound, *Br. J. Radiol.* 76(909), 617-624.

50. Ocak, I. et al. (2007) Dynamic Contrast-Enhanced MRI of Prostate Cancer at 3 T: A Study of Pharmacokinetic Parameters, *Am. J. Roentgenol.* 189, W192-W201.

51. Schlemmer, H.-P. et al. (2004) Can pre-operative contrast-enhanced dynamic MR imaging for prostate cancer predict microvessel density in prostatectomy specimens?, *Eur Radiol.* 14(2), 309-317.

52. Padhani, A. R. et al. (2000) Dynamic Contrast Enhanced MRI of Prostate Cancer: Correlation with Morphology and Tumour Stage, Histological Grade and PSA, *Clin. Radiol.* 55(2), 99-109.

53. Jang, H.-J. et al. (2007) Enhancement Patterns of Hepatocellular Carcinoma at Contrast-enhanced US: Comparison with Histologic Differentiation, *Radiology* 244(3), 898-906.

54. Jang, H.-J., Kim, T. K., and Wilson, S. R. (2006) Imaging of Malignant Liver Masses: Characterization and Detection, *Ultrasound Quarterly* 22(1), 19-29.

55. Fan, Z.-H. et al. (2006) Evaluation of Primary Malignancies of the Liver Using Contrast-Enhanced Sonography: Correlation With Pathology, *Am. J. Roentgenol.* 186(6), 1512-1519.

56. Liu, L. P. et al. (2009) Focal Hypoechoic Tumors of Fatty Liver. Characterization of Conventional and Contrast-Enhanced Ultrasonography, *J. Ultrasound Med.* 28, 1133-1142.

57. Quaia, E. et al. (2007) Diagnostic Value of Hepatocellular Nodule Vascularity After Microbubble Injection for Characterizing Malignancy in Patients with Cirrhosis, *Am. J. Roentgenol.* 189(6), 1474-1483.

58. Frericks, B. et al. (2009) Qualitative and quantitative evaluation of hepatocellular carcinoma and cirrhotic liver enhancement using Gd-EOB-DTPA, *AJR, American journal of roentgenology* 193(4), 1053-1060.

59. Cheung, O. and Sanyal, A. J. (2010) Recent advances in nonalcoholic fatty liver disease, *Current Opinion in Gastroenterology* 26(3), 202-208.

60. Goshima, S. et al. (2009) Optimal Acquisition Delay for Dynamic Contrast-Enhanced MRI of Hypervascular Hepatocellular Carcinoma, *Am. J. Roentgenol.* 192(3), 686-692.

61. Ito, K. et al. (2004) Multiarterial Phase Dynamic MRI of Small Early Enhancing Hepatic Lesions in Cirrhosis or Chronic Hepatitis: Differentiating Between Hypervascular Hepatocellular Carcinomas and Pseudolesions, *Am. J. Roentgenol.* 183(3), 699-705.

62. Yoon, S. et al. (2009) Multiphasic MDCT enhancement pattern of hepatocellular carcinoma smaller than 3 cm in diameter tumor size and cellular differentiation, *AJR, American journal of roentgenology* 193(6), W482-489.

63. Lee, K. H. Y. et al. (2004) Triple-Phase MDCT of Hepatocellular Carcinoma, *Am. J. Roentgenol.* 182(3), 643-649.

64. Fantin, V. R., St-Pierre, J., and Leder, P. (2006) Attenuation of LDH-A expression uncovers a link between glycolysis, mitochondrial physiology, and tumor maintenance, *Cancer Cell* 9(6), 425-434.

65. Li, Y. M. et al. (2005) A Hypoxia-Independent Hypoxia-Inducible Factor-1 Activation Pathway Induced by Phosphatidylinositol-3 Kinase/Akt in HER2 Overexpressing Cells, *Cancer Res.* 65(8), 3257-3263.

66. Kim, J.-w. and Dang, C. V. (2006) Cancer's Molecular Sweet Tooth and the Warburg Effect, *Cancer Res.* 66(18), 8927-8930.

67. Pedersen, P. (2007) Warburg, me and Hexokinase 2: Multiple discoveries of key molecular events underlying one of cancers' most common phenotypes, the "Warburg Effect", i.e., elevated glycolysis in the presence of oxygen, *J. Bioenerg. Biomembr.* 39(3), 211-222.

68. Baumann, F. et al. (2009) Lactate promotes glioma migration by TGF-beta2-dependent regulation of matrix metalloproteinase-2, *Neuro-oncol.* 11(4), 368-380.

69. Tang, W. and Hemler, M. E. (2004) Caveolin-1 Regulates Matrix Metalloproteinases-1 Induction and CD147/EMMPRIN Cell Surface Clustering, *J. Biol. Chem.* 279 (12), 11112-11118.

70. Le Floch, R. et al. (2011) CD147 subunit of lactate/H+ symporters MCT1 and hypoxia-inducible MCT4 is critical for energetics and growth of glycolytic tumors, *Proc. Natl. Acad. Sci. U.S.A.* 108(40), 16663-16668.

71. Brown, M. et al. (2008) NF-κB in carcinoma therapy and prevention, *Expert Opin. Ther Targets* 12(9), 1109-1122.

72. Shime, H. et al. (2008) Tumor-Secreted Lactic Acid Promotes IL-23/IL-17 Proinflammatory Pathway, *The Journal of Immunology* 180(11), 7175-7183.

73. Eskey, C. J. et al. (1993) Role of oxygen vs. glucose in energy metabolism in a mammary carcinoma perfused ex vivo: direct measurement by 31P NMR, *Proc. Natl. Acad. Sci. U.S.A.* 90(7), 2646-2650.

74. Liu, Y. and Matsui, 0. (2007) Changes of Intratumoral Microvessels and Blood Perfusion during Establishment of Hepatic Metastases in Mice1, *Radiology* 243(2), 386-395.

75. Mankoff D. A. et al. (2002) Blood Flow and Metabolism in Locally Advanced Breast Cancer: Relationship to Response to Therapy, *J. Nucl. Med* 43(4), 500-509.

76. Picchio, M. et al. (2008) Intratumoral Spatial Distribution of Hypoxia and Angiogenesis Assessed by 18F-FAZA and 125I-Gluco-RGD Autoradiography, *J. Nucl. Med* 49(4) 597-605.

77. Eby, P. R. et al. (2008) Metabolic and Vascular Features of Dynamic Contrast-enhanced Breast Magnetic Resonance Imaging and 150-Water Positron Emission Tomography Blood Flow in Breast Cancer, *Acad. Radiol.* 15(10), 1246-1254.

78. Mayer, A. et al. (2005) Microregional Expression of Glucose Transporter-1 and Oxygenation Status: Lack of Correlation in Locally Advanced Cervical Cancers, *Clinical Cancer Research* 11(7), 2768-2773.

79. Vaupel, P. and Thews, G. (1976) Pathophysiological aspects of glucose uptake by the tumor tissue under various conditions of oxygen and glucose supply, *Adv. Exp. Med. Biol.* 75, 547-553.

80. Gillies, R. and Gatenby, R. (2007) Adaptive landscapes and emergent phenotypes: why do cancers have high glycolysis?, *J. Bioenerg. Biomembr.* 39(3), 251-257.
81. Gatenby, R. et al. (2006) Acid-mediated tumor invasion: a multidisciplinary study, *Cancer Res.* 66(10), 5216-5223.
82. Graeber, T. G. et al. (1996) Hypoxia-mediated selection of cells with diminished apoptotic potential in solid tumours, *Nature* 379(6560), 88-91.
83. Semenza, G. L. et al. (1996) Hypoxia Response Elements in the AldolaseA, Enolase 1, and Lactate Dehydrogenase A Gene Promoters Contain Essential Binding Sites for Hypoxia-inducible Factor 1, *J. Biol. Chem.* 271(51), 32529-32537.
84. Walenta, S., Schroeder, T., and Mueller-Kliesser, W. (2004) Lactate in solid malignant tumors: Potential basis of a metabolic classification in clinical oncology, *Curr Med. Chem.* 11(16), 2195-2204.
85. Hunt, T. et al. (2007) Aerobically derived lactate stimulates revascularization and tissue repair via redox mechanisms, *Antioxid. Redox. Signal.* 9(8), 1115-1124.
86. Assmann, V. et al. (1999) The intracellular hyaluronan receptor RHAMM/IHABP interacts with microtubules and actin filaments, *J. Cell Sci.* 112(22), 3943-3954.
87. Hamilton, S. R. et al. (2007) The Hyaluronan Receptors CD44 and Rhamm (CD168) Form Complexes with ERK1,2 That Sustain High Basal Motility in Breast Cancer Cells, *J. Biol. Chem.* 282(22), 16667-16680.
88. Gullino, P. M., Clark, S. H., and Grantham, F. H. (1964) The Interstitial Fluid of Solid Tumors, *Cancer Res.* 24(5), 780-797.
89. Lao, M.-S. and Toth, D. (1997) Effects of Ammonium and Lactate on Growth and Metabolism of a Recombinant Chinese Hamster Ovary Cell Culture, *Biotechnol. Prog.* 13(5), 688-691.
90. Patel, S. D. et al. (2000) The Lactate Issue Revisited: Novel Feeding Protocols To Examine Inhibition of Cell Proliferation and Glucose Metabolism in Hematopoietic Cell Cultures, *Biotechnol. Prog.* 16(5), 885-892.
91. Cruz, H. et al. (2000) Effects of ammonia and lactate on growth, metabolism, and productivity of BHK cells, *Enzyme Microb. Technol.* 27(1-2), 43-52.
92. Ozturk, S. S., Riley, M. R., and Palsson, B. O. (1992) Effects of ammonia and lactate on hybridoma growth, metabolism, and antibody production, *Biotechnol. Bioeng.* 39(4), 418-431.
93. Marx, E., Mueller-Klieser, W., and Vaupel, P. (1988) Lactate-induced inhibition of tumor cell proliferation, *Int. J. Radiat. Oncol. Biol. Phys.* 14(5), 947-955.
94. Edkkilä, K. et al. (2002) Lactate inhibits germ cell apoptosis in the human testis, *Mol. Hum. Reprod.* 8(2), 109-117.
95. Thangaraju, M. et al. (2006) SLC5A8 Triggers Tumor Cell Apoptosis through Pyruvate-Dependent Inhibition of Histone Deacetylases, *Cancer Res.* 66(24), 11560-11564.
96. Samuvel, D. J. et al. (2009) Lactate Boosts TLR4 Signaling and NF-κB Pathway-Mediated Gene Transcription in Macrophages via Monocarboxylate Transporters and MD-2 Up-Regulation, *The Journal of Immunology* 182(4), 2476-2484.
97. Choi, E.-M. et al. (2005) COX-2 regulates p53 activity and inhibits DNA damage-induced apoptosis, *Biochem. Biophys. Res. Commun.* 328(4), 1107-1112.
98. Brackstone, M., Townson, J. L., and Chambers, A. (2007) Tumour dormancy in breast cancer an update, *Breast Cancer Res.* 9(3), 208.
99. Rutz, H. P. and Little, J. B. (1995) Exogenous lactate interferes with cell-cycle control in Balb 3T3 mouse fibroblasts, *Int. J. Radiat. Oncol. Biol. Phys.* 31(3), 525-528.
100. Hunt, T. K. et al. (2008) Lactate, with Oxygen, Incites Angiogenesis, in *Oxygen Transport to Tissue XXIX* (Kang, K. A., Harrison, D. K., and Bruley, D. F., Eds.), pp 73-80, Springer US.
101. Dietl, K. et al. (2010) Lactic Acid and Acidification Inhibit TNF Secretion and Glycolysis of Human Monocytes, *The Journal of Immunology* 184(3), 1200-1209.
102. Majewski, N. et al. (2004) Akt Inhibits Apoptosis Downstream of BID Cleavage via a Glucose-Dependent Mechanism Involving Mitochondrial Hexokinases, *Mol. Cell. Biol.* 24(2), 730-740.
103. Kondoh, H. et al. (2005) Glycolytic Enzymes Can Modulate Cellular Life Span, *Cancer Res.* 65(1), 177-185.
104. Quennet, V. et al. (2006) Tumor lactate content predicts for response to fractionated irradiation of human squamous cell carcinomas in nude mice, *Radiotherapy and oncology: Journal of the European Society for Therapeutic Radiology and Oncology* 81(2), 130-135.
105. Sattler, U. G. A. et al. (2010) Glycolytic metabolism and tumour response to fractionated irradiation, *Radiotherapy and oncology: Journal of the European Society for Therapeutic Radiology and Oncology* 94(1), 102-109.
106. Feldmeier, J. et al. (2003) Hyperbaric oxygen: does it promote growth or recurrence of malignancy?, *Undersea Hyper Med.* 30(1), 1-18.
107. Schönmeyr, B. et al. (2008) The effect of hyperbaric oxygen treatment on squamous cell cancer growth and tumor hypoxia, *Ann. Plast. Surg.* 60(1), 81-88.
108. Rutz, H. P. (1999) A biophysical basis of enhanced interstitial fluid pressure in tumors, *Med. Hypotheses* 53(6), 526-529.
109. Eichten, A., Hyun, W. C., and Coussens, L. M. (2007) Distinctive Features of Angiogenesis and Lymphangiogenesis Determine Their Functionality during De novo Tumor Development, *Cancer Res.* 67(11), 5211-5220.
110. Hoshida, T. et al. (2006) Imaging Steps of Lymphatic Metastasis Reveals That Vascular Endothelial Growth Factor-C Increases Metastasis by Increasing Delivery of Cancer Cells to Lymph Nodes: Therapeutic Implications, *Cancer Res.* 66(16), 8065-8075.
111. Karpanen, T. et al. (2001) Vascular Endothelial Growth Factor C Promotes Tumor Lymphangiogenesis and Intralymphatic Tumor Growth, *Cancer Res.* 61(5), 1786-1790.
112. Sonveaux, P. et al. (2008) Targeting lactate-fueled respiration selectively kills hypoxic tumor cells in mice, *J. Clin. Invest.* 118(12), 3930-3942.
113. Koukourakis, M.-I. et al (2006) Comparison of Metabolic Pathways between Cancer Cells and Stromal Cells in Colorectal Carcinomas: a Metabolic Survival Role for Tumor-Associated Stroma, *Cancer Res.* 66(2), 632-637.
114. Semenza, G. L. (2008) Tumor metabolism: cancer cells give and take lactate, *J. Clin. Invest.* 118(12), 3835-3837.
115. Heinzman, J. M., Brower, S. L., and Bush, J. E. (2008) Comparison of angiogenesis-related factor expression in primary tumor cultures under normal and hypoxic growth conditions, *Cancer Cell International* 8, 11.
116. Mukherjee, A. et al. (2005) Cytotoxic and antiangiogenic activity of AW464 (NSC 706704), a novel thioredoxin inhibitor: an in vitro study, *Br. J. Cancer* 92(2), 350-358.

117. Mizukami, Y. et al. (2004) Hypoxia-Inducible Factor-1-Independent Regulation of Vascular Endothelial Growth Factor by Hypoxia in Colon Cancer, *Cancer Res.* 64(5), 1765-1772.
118. Xiong, B. et al. (2002) TGF beta1 expression and angiogenesis in colorectal cancer tissue, *World J. Gastroenterol.* 8(3), 496-498.
119. Swift, M. R. and Weinstein, B. M. (2009) Arterial-Venous Specification During Development, *Circ. Res.* 104(5), 576-588.
120. Srinivasan, R. S. et al. (2007) Lineage tracing demonstrates the venous origin of the mammalian lymphatic vasculature, *Genes Dev.* 21, 2422-2432.
121. Höpfl, G, Ogunshola, O., and Gassmann, M. (2004) HIFs and tumors—causes and consequences, *American Journal of Physiology—Regulatory, Integrative and Comparative Physiology* 286(4), R608-R623.
122. Lu, H. et al. (2005) Reversible Inactivation of HIF-1 Prolyl Hydroxylases Allows Cell Metabolism to Control Basal HIF-1, *J. Biol. Chem.* 280(51), 41928-41939.
123. McFate, T.-et al. (2008) Pyruvate Dehydrogenase Complex Activity Controls Metabolic and Malignant Phenotype in Cancer Cells, *J. Biol. Chem.* 283(33), 22700-22708.
124. Hägg M. and Wennström, S. (2005) Activation of hypoxia-induced transcription in normoxia, *Exp. Cell Res.* 306(1), 180-191.
125. Mekhail, K. et al. (2004) Oxygen Sensing by H+: Implications for HIF and Hypoxic Cell Memory, *Cell Cycle* 3(8), 1025-1027.
126. Chang, L. K. et al (2004) Dose-dependent response of FGF-2 for lymphangiogenesis, *Proc. Natl. Acad. Sci. U.S.A.* 101(32), 11658-11663.
127. Pore, N. et al. (2004) Sp1 Is Involved in Akt-mediated Induction of VEGF Expression through an HIF-1-independent Mechanism, *Mol. Biol. Cell* 15(11), 4841-4853.
128. Pore, N. et al. (2006) Akt1 Activation Can Augment Hypoxia-Inducible Factor-1α Expression by Increasing Protein Translation through a Mammalian Target of Rapamycin-Independent Pathway, *Mol. Cancer Res.* 4(7), 471-479.
129. Mizukami, Y. et al. (2006) Hypoxic Regulation of Vascular Endothelial Growth Factor through the Induction of Phosphatidylinositol 3-Kinase/Rho/ROCK and c-Myc, *J. Biol. Chem.* 281(20), 13957-13963.
130. Stein, I. et al. (1995) Stabilization of vascular endothelial growth factor mRNA by hypoxia and hypoglycemia and coregulation with other ischemia-induced genes, *Mol. Cell. Biol.* 15(10), 5363-5368.
131. Zhong, H. et al. (2000) Modulation of Hypoxia-inducible Factor 1α Expression by the Epidermal Growth Factor/Phosphatidylinositol 3-Kinase/PTEN/AKT/FRAP Pathway in Human Prostate Cancer Cells: Implications for Tumor Angiogenesis and Therapeutics, *Cancer Res.* 60(6), 1541-1545.
132. Song, Y. et al. (2009) Sp-1 and c-Myc Mediate Lysophosphatidic Acid-Induced Expression of Vascular Endothelial Growth Factor in Ovarian Cancer Cells via a Hypoxia-Inducible Factor-1-Independent Mechanism, *Clinical Cancer Research* 15(2), 492-501.
133. D'Arcangelo, D. et al. (2000) Acidosis Inhibits Endothelial Cell Apoptosis and Function and Induces Basic Fibroblast Growth Factor and Vascular Endothelial Growth Factor Expression, *Circ. Res.* 86(3), 312-318.
134. Fukumura, D. et al. (2001) Hypoxia and Acidosis Independently Up-Regulate Vascular Endothelial Growth Factor Transcription in Brain Tumors in Vivo, *Cancer Res.* 61(16), 6020-6024.
135. Goerges, A. L. and Nugent, M. A. (2004) pH Regulates Vascular Endothelial Growth Factor Binding to Fibronectin, *J. Biol. Chem.* 279(3), 2307-2315.
136. Saksela, O. and Rifkin, D. B. (1990) Release of basic fibroblast growth factor-heparan sulfate complexes from endothelial cells by plasminogen activator-mediated proteolytic activity, *The Journal of Cell Biology* 110(3), 767-775.
137. Kato, Y. et al. (2005) Acidic Extracellular pH Induces Matrix Metalloproteinase-9 Expression in Mouse Metastatic Melanoma Cells through the Phospholipase D-Mitogen-activated Protein Kinase Signaling, *J. Biol. Chem.* 280(12), 10938-10944.
138. Shi, Q. et al. (2001) Regulation of vascular endothelial growth factor expression by acidosis in human cancer cells, *Oncogene* 20(28), 3751-3756.
139. Constant, J. S. et al. (2000) Lactate elicits vascular endothelial growth factor from macrophages: a possible alternative to hypoxia, *Wound Repair. Regen.* 8(5), 353-360.
140. Beckert, S. et al. (2006) Lactate stimulates endothelial cell migration, *Wound Repair Regen.* 14(3), 321-324.
141. Jensen, J. A. et al. (1986) Effect of lactate, pyruvate, and pH on secretion of angiogenesis and mitogenesis factors by macrophages, *Lab. Invest.* 54(5), 574-578.
142. Kumar, V. B. S. et al. (2007) Endothelial cell response to lactate: Implication of PAR modification of VEGF, *J. Cell. Physiol.* 211(2), 477-485.
143. Xu, L., Fukumura, D., and Jain, R. K. (2002) Acidic Extracellular pH Induces Vascular Endothelial Growth Factor (VEGF) in Human Glioblastoma Cells via ERK1/2 MAPK Signaling Pathway, *J. Biol. Chem.* 277(13), 11368-11374.
144. Colotta, F. et al. (2009) Cancer-related inflammation, the seventh hallmark of cancer: links to genetic instability, *Carcinogenesis* 30(7), 1073-1081.
145. Hong, Y.-K., Shin, J. W., and Detmar, M. (2004) Development of the lymphatic vascular system: A mystery unravels, *Dev. Dyn.* 231(3), 462-473.
146. Holash, J., Wiegand, S. J., and Yancopoulos, G. D. (1999) New model of tumor angiogenesis: dynamic balance between vessel regression and growth mediated by angiopoietins and VEGF, *Oncogene* 18(38), 5356-5362.
147. Moyon, D. et al. (2001) Plasticity of endothelial cells during arterial-venous differentiation in the avian embryo, *Development* 128(17), 3359-3370.
148. Hong, C. C. et al. (2006) Artery/Vein Specification Is Governed by Opposing Phosphatidylinositol-3 Kinase and MAP Kinase/ERK Signaling, *Current biology: CB* 16(13), 1366-1372.
149. Indraccolo, S. et al. (2006) Interruption of tumor dormancy by a transient angiogenic burst within the tumor microenvironment, *Proc. Natl. Acad. Sci. U.S.A.* 103(11), 4216-4221.
150. Cao, Y. et al. (2005) Observation of Incipient Tumor Angiogenesis That Is Independent of Hypoxia and Hypoxia Inducible Factor-1 Activation, *Cancer Res.* 65(13), 5498-5505.
151. Schmidt, D. et al. (2007) Critical role for NF-KB-induced JunB in VEGF regulation and tumor angiogenesis, *EMBO J.* 26(3), 710-719.

152. Hong, Y.-K. et al. (2004) VEGF-A promotes tissue repair-associated lymphatic vessel formation via VEGFR-2 and the α1β1 and α2β1 integrins, *The FASEB Journal*.

153. Sato, Y. (2008) VEGFR1 for Lymphangiogenesis. An Alternative Signaling Pathway?, *Arterioscler. Thromb. Vasc. Biol.* 28, 604.

154. Kyzas, P. A., Stefanou, D., and Agnantis, N. J. (2004) COX-2 expression correlates with VEGF-C and lymph node metastases in patients with head and neck squamous cell carcinoma, *Mod. Pathol.* 18(1), 153-160.

155. Timoshenko, A. V. et al. (2006) COX-2-mediated stimulation of the lymphangiogenic factor VEGF-C in human breast cancer, *Br. J. Cancer* 94(8), 1154-1163.

156. Enholm, B. et al. (2001) Adenoviral Expression of Vascular Endothelial Growth Factor-C Induces Lymphangiogenesis in the Skin, *Circ. Res.* 88(6), 623-629.

157. Nagy, J. A. et al. (2002) VEGF-A induces angiogenesis, arteriogenesis, lymphangiogenesis, and vascular malformations, *Cold Spring Harbor Symp. Quant. Biol.* 67, 227-237.

158. Pettersson, A. et al. (2000) Heterogeneity of the Angiogenic Response Induced in Different Normal Adult Tissues by Vascular Permeability Factor/Vascular Endothelial Growth Factor, *Lab. Invest.* 80(1), 99-115.

159. Vihanto, M. M. et al. (2005) Hypoxia up-regulates expression of Eph receptors and ephrins in mouse skin, *The FASEB Journal*.

160. Huang, X. et al. (2007) EphB4 Overexpression in B16 Melanoma Cells Affects Arterial-Venous Patterning in Tumor Angiogenesis, *Cancer Res.* 67(20), 9800-9808.

161. Hayashi, S.-i. et al. (2005) Functional Ephrin-B2 Expression for Promotive Interaction Between Arterial and Venous Vessels in Postnatal Neovascularization, *Circulation* 111(17), 2210-2218.

162. Yancopoulos, G. D. et al. (2000) Vascular-specific growth factors and blood vessel formation, *Nature* 407 (6801), 242-248.

163. Patan, S. et al. (2001) Vascular Morphogenesis and Remodeling in a Human Tumor Xenograft, *Circ. Res.* 89(8), 732-739.

164. Li, C.-Y. et al. (2000) Initial Stages of Tumor Cell-Induced Angiogenesis: Evaluation Via Skin Window Chambers in Rodent Models, *J. Natl. Cancer Inst.* 92(2), 143-147.

165. Koyama, H. et al. (2008) Significance of Tumor-Associated Stroma in Promotion of Intratumoral Lymphangiogenesis: Pivotal Role of a Hyaluronan-Rich Tumor Microenvironment, *The American journal of pathology* 172(1), 179-193.

166. Pasqui, D. et al. (2005) Hyaluronan and sulphated hyaluronan micropatterns: effect of chemical topographic cues on lymphatic endothelial cell alignment and proliferation, *Lymphology* 38(2), 50-65.

167. Hendriksen, E. M. et al. (2009) Angiogenesis, hypoxia and VEGF expression during tumour growth in a human xenograft tumour model, *Microvasc. Res.* 77(2), 96-103.

168. Itano, N. et al. (2002) Abnormal accumulation of hyaluronan matrix diminishes contact inhibition of cell growth and promotes cell migration, *Proc. Natl. Acad. Sci. U.S.A.* 110. 99(6), 3609-3614.

169. Koyama, H. et al. (2007) Hyperproduction of Hyaluronan in Neu-Induced Mammary Tumor Accelerates Angiogenesis through Stromal Cell Recruitment: Possible Involvement of Versican/PG-M, *The American journal of pathology* 170(3), 1086-1099.

170. Hall, C. L. and Turley, E. A. (1995) Hyaluronan: RHAMM mediated cell locomotion and signaling in tumorigenesis, *J. Neurooncol.* 26(3), 221-229.

171. Fischer, K. et al. (2007) Inhibitory effect of tumor cell-derived lactic acid on human T cells, *Blood* 109(9), 3812-3819.

172. Kuang, D.-M. et al. (2007) Tumor-derived hyaluronan induces formation of immunosuppressive macrophages through transient early activation of monocytes, *Blood* 110(2), 587-595.

173. Lin, E. Y. et al. (2006) Macrophages Regulate the Angiogenic Switch in a Mouse Model of Breast Cancer, *Cancer Res.* 66(23), 11238-11246.

174. Alphonso, A. and Alahari, S. K. (2009) Stromal cells and integrins: Conforming to the needs of the tumor microenvironment, *Neoplasia* 11(12), 1264-1271.

175. Nissen, N. N. et al. (1999) Heparin and heparan sulphate protect basic fibroblast growth factor from non-enzymic glycosylation, *Biochem. J.* 338(3), 637-642.

176. Arbiser, J. L. (2007) Why targeted therapy hasn't worked in advanced cancer, *J. Clin. Invest.* 117(10), 2762-2765.

177. Yoshiji, H., Harris, S. R., and Thorgeirsson, U. P. (1997) Vascular Endothelial Growth Factor Is Essential for Initial but not Continued in Vivo Growth of Human Breast Carcinoma Cells, *Cancer Res.* 57(18), 3924-3928.

178. Giavazzi, R. et al. (2001) Modulation of Tumor Angiogenesis by Conditional Expression of Fibroblast Growth Factor-2 Affects Early but not Established Tumors, *Cancer Res.* 61(2), 309-317.

179. Grillon, E. et al. (2011) The spatial organization of proton and lactate transport in a rat brain tumor, *PLoS One* 6(2), e17416.

180. Selvakumaran, M. et al. (2008) Antitumor effect of the angiogenesis inhibitor bevacizumab is dependent on susceptibility of tumors to hypoxia-induced apoptosis, *Biochem. Pharmacol.* 75(3), 627-638.

181. Siemann, D. W. (2011) The unique characteristics of tumor vasculature and preclinical evidence for its selective disruption by Tumor-Vascular Disrupting Agents, *Cancer Treat. Rev.* 37(1), 63-74.

182. Davis, P. A. and Cousins, S. "Biodegradable injectable drug delivery polymer," U.S. Pat. No. 5,384,333, filed Mar. 17, 1992. (Published Jan. 24, 1995).

183. Amsden, B. G. and Cheng, Y.-I. "Polymer-based drug delivery system," U.S. Pat. No. 5,302,397, filed Nov. 19, 1991. (Published Apr. 12, 1994).

184. Amsden, B. G. and Cheng, Y.-I. "Polymer-based drug delivery system," U.S. Pat. No. 5,626,877, filed Feb. 9, 1994. (Published May 6, 1997).

185. Wadee, A. et al. (2011) Recent advances in the design of drug-loaded polymeric implants for the treatment of solid tumors, *Expert Opin. Drug Deliv.* 8(10), 1323-1340.

186. Hamed, E. A. M. (2002) Application and Evaluation of Extended Release Technology to Loop Diuretics, in *Department of Pharmaceutical Sciences of the College of Pharmacy*, p 208, University of Cincinnati.

187. Schoenwald, R. D. and Barfknecht, C. F. "Prodrugs of carbonic anhydrase inhibitors," U.S. Pat. No. 5,095,026 application Ser. No. 07/410,982, filed Sep. 22, 1989. (Published Mar. 10, 1992).

188. Klenke, F. et al. (2007) Tyrosine kinase inhibitor SU6668 represses chondrosarcoma growth via antiangiogenesis in vivo, *BMC Cancer* 7(1), 49.

189. Figg, W. D. et al. (2002) Inhibition of Angiogenesis: Treatment Options for Patients with Metastatic Prostate Cancer, *Invest. New Drugs* 20(2), 183-194.

190. Gordon, M. S. et al. (2001) Phase I Safety and Pharmnacokinetic Study of Recombinant Human Anti-Vascular Endothelial Growth Factor in Patients With Advanced Cancer, *Journal of Clinical Oncology* 19(3), 843-850.
191. Hurwitz, H. (2003) Bevacizumab (Avastin, a monoclonal antibody to vascular endothelial growth factor) prolongs survival in first-line colorectal cancer (CRC): results of a phase III trial of bevacizumab in combination with bolus IFL (irinotecan, 5-fluorouracil, leucovorin), in *Presented at the 39th Annual American Society of Clinical Oncology Meeting*, Chicago, Ill.
192. Cobleigh, M. A. et al. (2003) A phase I/II dose-escalation trial of bevacizumab in previously treated metastatic breast cancer, *Semin. Oncol.* 30, 117-124.
193. Chen, H. X., Gore-Langton, R. E., and Cheson, B. D. (2001) Clinical trials referral resource: Current clinical trials of the anti-VEGF monoclonal antibody bevacizumab, *Oncology (Williston Park)* 15(8), 1017, 1020, 1023-1016.

We claim:

1. A method for treating a patient with cancer, said method comprising:
   a) providing:
      i) a patient exhibiting a neoplasm, wherein said neoplasm comprises a plurality of blood vessels; and
      ii) a composition comprising at least one polymer and bumetanide;
   b) administering said composition to said patient under conditions such that said blood vessels are occluded, wherein said blood vessel occlusions comprises emboli.
2. The method according to claim 1, wherein said neoplasm is hypoxic.
3. The method according to claim 1, wherein said administering results in the shrinkage of said neoplasm.
4. The method according to claim 1, wherein said administering further comprises an angiogenesis inhibitor.
5. The method according to claim 4, wherein said angiogenesis inhibitor is selected from the group consisting of ZD6474, ZD 6126, AZD2171, SU6668, SU5416, bevacizumab, mv833, anti-FLT-1 ribozyme, SU5416, PTK 787, ZD4190, ZD6474, CEP-7055, SU11248, and mixtures thereof.
6. The method according to claim 1, wherein said emboli comprises said composition.
7. The method according to claim 6, wherein said administering of said composition is repeated.
8. The method according to claim 6, wherein said composition comprises a slow-release polymer formulation.
9. The method according to claim 1, wherein said administering further comprises a thermal ablation of said neoplasm.
10. The method according to claim 9, wherein said thermal ablation is preceded by said bumetanide composition administration.
11. The method according to claim 9, wherein said thermal ablation comprises radiofrequency thermal ablation.
12. The method according to claim 9, wherein said thermal ablation comprises cryoablation.
13. The method according to claim 9, wherein said thermal ablation comprises microwave ablation.
14. The method according to claim 9, wherein said thermal ablation comprises laser ablation.
15. The method according to claim 9, wherein said thermal ablation comprises ultrasound ablation.

* * * * *